(12) United States Patent
Ataman-Onal et al.

(10) Patent No.: US 11,225,518 B2
(45) Date of Patent: Jan. 18, 2022

(54) METHOD FOR PREPARING ANTI-AMH ANTIBODIES AND USES OF SAME

(71) Applicant: BIOMÉRIEUX, Marcy l'Etoile (FR)

(72) Inventors: Yasemin Ataman-Onal, Reyrieux (FR); Sylvie Cheucle, La Tour de Salvagny (FR); Maxime Combe, Lyons (FR); Soizic Daniel, Trevoux (FR); Sophie Ottone, Sain-Bel (FR)

(73) Assignee: BIOMÉRIEUX, Marcy l'Etoile (FR)

( * ) Notice: Subject to any disclaimer, the term of this patent is extended or adjusted under 35 U.S.C. 154(b) by 0 days.

(21) Appl. No.: 16/310,802

(22) PCT Filed: Jun. 16, 2017

(86) PCT No.: PCT/EP2017/064759
§ 371 (c)(1),
(2) Date: Dec. 17, 2018

(87) PCT Pub. No.: WO2017/216334
PCT Pub. Date: Dec. 21, 2017

(65) Prior Publication Data
US 2019/0211096 A1    Jul. 11, 2019

(30) Foreign Application Priority Data

Jun. 17, 2016 (EP) .................... 16175041

(51) Int. Cl.
*C07K 16/26* (2006.01)
*G01N 33/74* (2006.01)
*G01N 33/68* (2006.01)

(52) U.S. Cl.
CPC ........... *C07K 16/26* (2013.01); *G01N 33/689* (2013.01); *G01N 33/74* (2013.01); *C07K 2317/10* (2013.01); *C07K 2317/34* (2013.01); *G01N 2333/575* (2013.01); *G01N 2800/367* (2013.01)

(58) Field of Classification Search
None
See application file for complete search history.

(56) References Cited

U.S. PATENT DOCUMENTS

| | | | |
|---|---|---|---|
| 4,196,265 A * | 4/1980 | Koprowski | C07K 16/08 435/339 |
| 7,429,487 B2 | 9/2008 | Pytela et al. | |
| 7,897,350 B2 | 3/2011 | Groome et al. | |

FOREIGN PATENT DOCUMENTS

| | | |
|---|---|---|
| WO | 92/15699 A1 | 9/1992 |
| WO | 2006/127850 A1 | 11/2006 |
| WO | 2008/153433 A1 | 12/2008 |
| WO | 2014/074835 A2 | 5/2014 |
| WO | 2014/204327 A1 | 12/2014 |

OTHER PUBLICATIONS

Marc H.V. Van Regenmortel, Methods Mol Biol. 2009; 524: 3-20. doi: 10.1007/978-1-59745-450-6_1 (Year: 2009).*
Piche-Nicholas et al., MAbs. 2018; 10: 81-94. doi: 10.1080/19420862.2017.1389355 (Year: 2018).*
Ghoshal et al., Journal of Neurochemistry, 2001, 77, 1372-1385 (Year: 2001).*
Mumey et al., Journal of Computational Biology, 2003; 10: 555-567 (Year: 2003).*
Arce, Joan-Carles et al. "Ovarian response to recombinant human follicle-stimulating hormone: a randomized, antimüllerian hormone-stratified, dose-response trial in women undergoing in vitro fertilization/intracytoplasmic sperm injection". Fertility and Sterility, vol. 102, 1633-1640.e5, 2014.

(Continued)

*Primary Examiner* — Christina M Borgeest
(74) *Attorney, Agent, or Firm* — Oliff PLC

(57) ABSTRACT

The present invention relates to a method for preparing anti-mammalian AMH antibodies comprising the steps of:
(i) immunizing an animal with an AMH polypeptide or a polynucleotide encoding this AMH polypeptide, said AMH polypeptide comprising at least the 99 amino acids of sequence SEQ ID No. 1 or of a sequence having at least 75% identity with the sequence SEQ ID No. 1, and at most the 560 amino acids of sequence SEQ ID No. 2 or of a sequence having at least 75% identity with the sequence SEQ ID No. 2,
(ii) preparing hybridomas from cells of a lymphoid organ of the animal having received the immunogen,
(iii) selecting hybridomas secreting antibodies recognizing an AMH polypeptide comprising at least the 99 amino acids of sequence SEQ ID No. 1 or of a sequence having at least 75% identity with the sequence SEQ ID No. 1, and at most the 255 amino acids of sequence SEQ ID No. 8 or of a sequence having at least 75% identity with the sequence SEQ ID No. 8, but recognizing neither (a) an AMH polypeptide comprising at least the 131 amino acids of sequence SEQ ID No. 13 or of a sequence having at least 75% identity with the sequence SEQ ID No. 13 and at most the 156 amino acids of sequence SEQ ID No. 11 or of a sequence having at least 75% identity with the sequence SEQ ID No. 11, nor (b) any linear epitope located in the sequence SEQ ID No. 1 or a sequence having at least 75% identity with the sequence SEQ ID No. 1, and
(iv) producing the antibodies.

Figure 1:
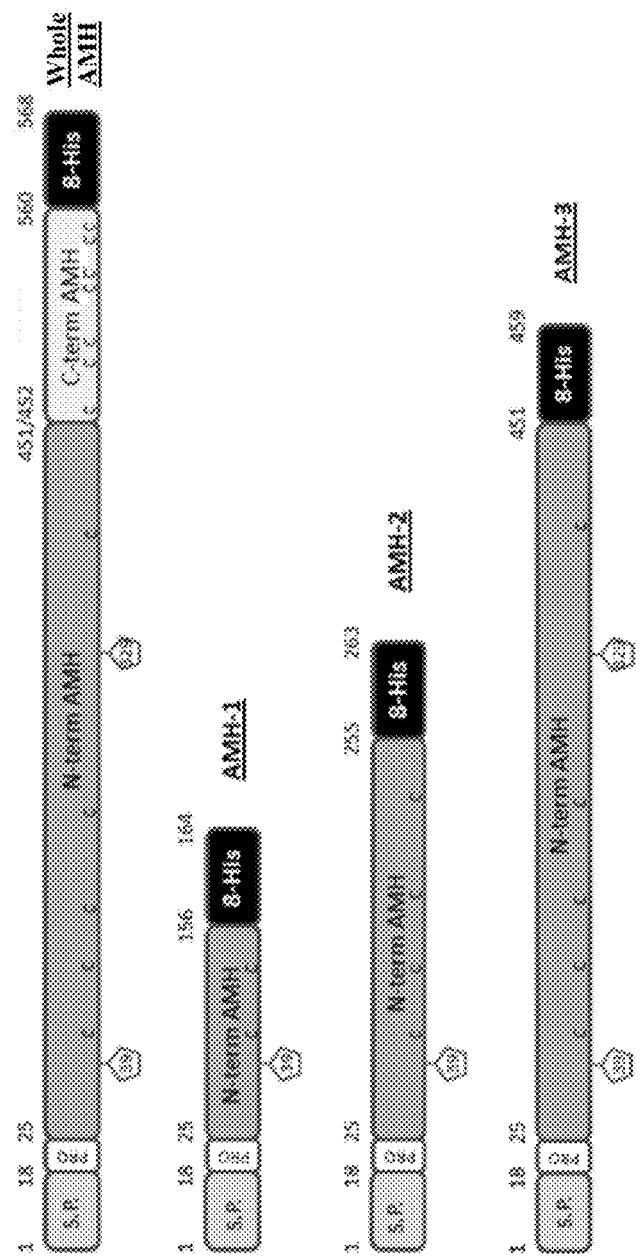

The invention also relates to the antibodies and antibody fragments and the use of same for assaying AMH, in particular in fertility.

11 Claims, 4 Drawing Sheets

Specification includes a Sequence Listing.

(56) References Cited

OTHER PUBLICATIONS

Boersma, Ykelien et al. "DARPins and other repeat protein scaffolds: advances in engineering and applications". Pharmaceutical Biotechnology, vol. 22, 849-857, 2011.

Chai, Joyce et al. "A highly-sensitive anti-Müllerian hormone assay improves analysis of ovarian function following chemotherapy for early breast cancer". European Journal of Cancer, vol. 50, 2367-2374, 2014.

Dewailly, Didier et al. "The physiology and clinical utility of anti-Müllerian hormone in women". Human Reproduction Update, vol. 20, 370-385, 2014.

Ellington, Andrew et al. "In vitro selection of RNA molecules that bind specific ligands". Nature, vol. 346, 818-822, 1990.

Falkenberg, F.W. "Production of monoclonal antibodies in the miniPERM bioreactor: comparison with other hybridoma culture methods". 74th Forum in Immunology, vol. 149, 560-570, 1998.

Fong, Sharon et al. "The role of anti-Müllerian hormone in the classification of anovulatory infertility". European Journal of Obstetrics & Gynecology and Reproductive Biology, vol. 186, 75-79, 2015.

Han, Xuguang et al. "Pre-mixing serum samples with assay buffer is a prerequisite for reproducible anti-Müllerian hormone measurement using the Beckman Coulter Gen II assay". Human Reproduction, vol. 29, 1042-1048, 2014.

Hudson, Peter et al. "An Immunoassay to Detect Human Mullerian Inhibiting Substance in Males and Females during Normal Development". Journal of Clinical Endocrinology and Metabolism, vol. 70, 16-22, 1990.

Kelsey, Thomas. "A Validated Model of Serum Anti-Müllerian Hormone from Conception to Menopause". PLoS One, vol. 6, e22024, 2011.

Köhler, G et al. "Continuous cultures of fused cells secreting antibody of predefined specificity". Nature, vol. 256, 495-497, 1975.

Köhler, G et al. "Fusion between immunoglobulin-secreting and nonsecreting myeloma cell lines". European Journal of Immunology, vol. 6, 292-295, 1976.

Kumar, Ajay et al. "Development of a second generation anti-Müllerian hormone (AMH) ELISA". Journal of Immunological Methods, vol. 362, 51-59, 2010.

Lee, Mary et al. "Mullerian Inhibiting Substance in Humans: Normal Levels from Infancy to Adulthood". Journal of Clinical Endocrinology and Metabolism, vol. 81, 571-576, 1996.

Long, Wen-Qing et al. "Detection of Minimal Levels of Serum Anti-Müllerian Hormone during Follow-Up of Patients with Ovarian Granulosa Cell Tumor by Means of a Highly Sensitive Enzyme-Linked Immunosorbent Assay". The Journal of Clinical Endocrinology & Metabolism, vol. 85, 540-544, 2000.

Lukaszuk, Krzysztof et al. "Decreasing Quality of the New Generations of Anti-Müllerian Hormone Assays". BioMed Research International, vol. 2014, 1-7, 2014.

Rustamov, Oybek et al. "Anti-Müllerian hormone: poor assay reproducibility in a large cohort of subjects suggests sample instability". Human Reproduction, vol. 27, 3085-3091, 2012.

Pankhurst, Michael et al. "Relative levels of the proprotein and cleavage-activated form of circulating human anti-Müllerian hormone are sexually dimorphic and variable during the life cycle". Physiological Reports, vol. 4, 1-10, 2016.

Zec, Ivana et al. "Anti-Müllerian hormone: A unique biochemical marker of gonadal development and fertility in humans". Biochemia Medica, vol. 21, 219-230, 2011.

Sep. 13, 2017 Written Opinion of International Searching Authority issued in International Patent Application No. PCT/EP2017/064759.

Sep. 13, 2017 Search Report issued in International Patent Application No. PCT/EP2017/064759.

\* cited by examiner

FIGURE 2
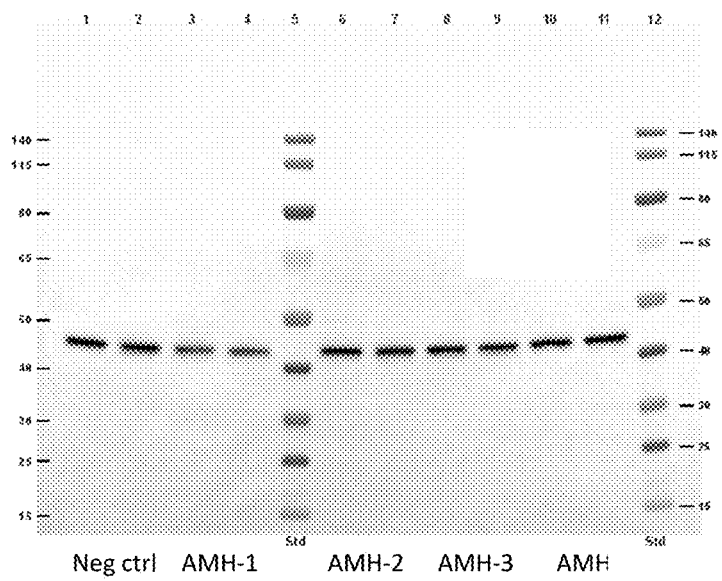
Figure 2A
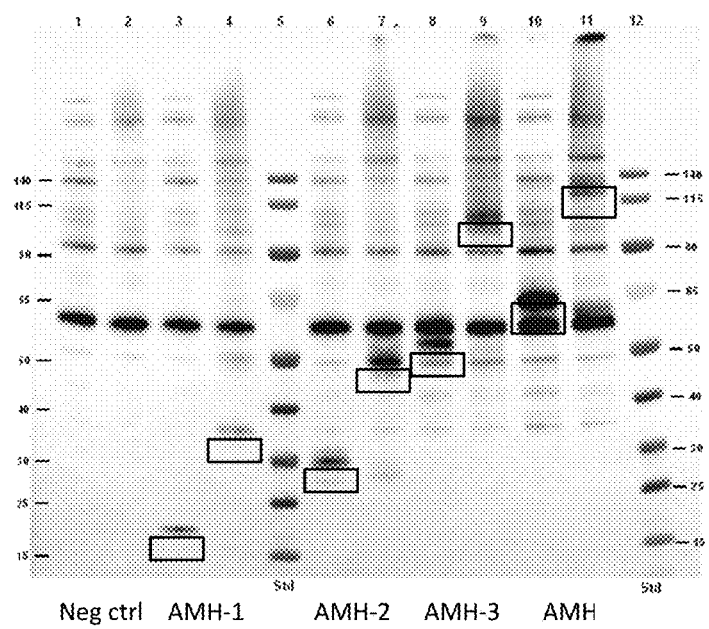
Figure 2B

FIGURE 3
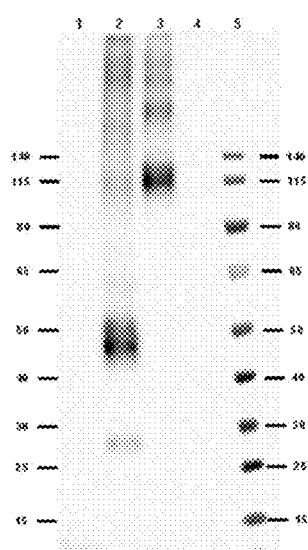
Fig 3A
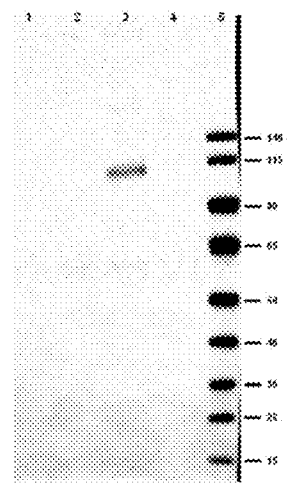
Fig 3B
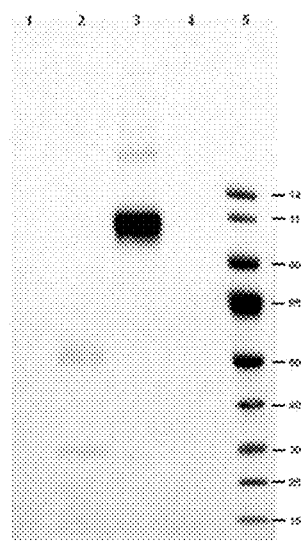
Fig 3C
1- Negative control
2- AMH 2
3- AMH 3
5- Molecular weight standard
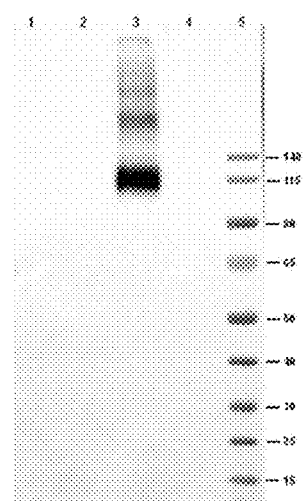
Fig 3D
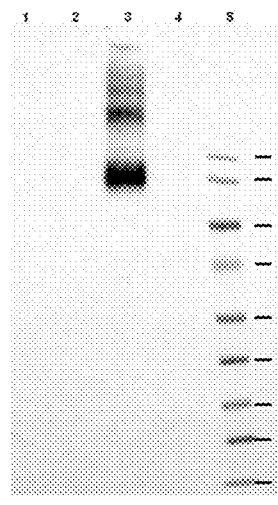
Fig 3E

METHOD FOR PREPARING ANTI-AMH ANTIBODIES AND USES OF SAME

The present invention relates to the field of the in vitro detection of the anti-Müllerian hormone, also known as AMH. In particular, the invention relates to the preparation of anti-AMH antibodies, to the anti-AMH antibodies and to the uses thereof for determining the AMH concentration, in particular in the context of examinations associated with fertility in women or female animals of child-bearing age.

The anti-Müllerian hormone (also known as AMH) is a dimeric glycoprotein of 144 kDa of the Transforming Growth Factor (TGF-β) family, which family comprises numerous factors that act on growth and differentiation. AMH is a dimeric prohormone: it consists of two identical subunits which are linked by disulfide bridges. This prohormone undergoes proteolytic cleavage close to the C-terminal end in order to acquire a biological activity and to be converted into mature hormone. After cleavage, the molecular complex remains linked and can be assayed in the blood by immunoassay allowing sensitivity performance levels suitable for monitoring the change in ovarian reserve from birth to menopause (Kelsey T W, et al., 2011). This protein is also known as MIF (Müllerian-inhibiting factor), MIH (Müllerian-inhibiting hormone) and MIS (Müllerian-inhibiting substance).

AMH is present in all mammals. Its amino acid length and sequence are dependent on the species. Thus, human AMH has 560 amino acids and is made up as follows: a short signal peptide (amino acids 1-18), a precursor portion (amino acids 19-25), an N-terminal portion (amino acids 26-451) and a C-terminal portion (amino acids 452-560). Equine AMH has 573 amino acids and is made up as follows: a short signal peptide (amino acids 1-22), no precursor portion, an N-terminal portion (amino acids 23-464) and a C-terminal portion (amino acids 465-573). Canine AMH has 572 amino acids and is made up as follows: a short signal peptide (amino acids 1-21), no precursor portion, an N-terminal portion (amino acids 22-463) and a C-terminal portion (amino acids 464-572). Bovine AMH, for its part, has 575 amino acids and is made up as follows: a short signal peptide (amino acids 1-17), a precursor portion (amino acids 18-24), an N-terminal portion (amino acids 25-466) and a C-terminal portion (amino acids 467-575). Regardless of the species, the N-terminal portion of AMH is called the "pro region" and the C-terminal portion is called the "mature region".

AMH is synthesized in the form of a polypeptide precursor comprising the signal peptide, followed by the preprohormone (in human beings and bovines) or by the prohormone (in horses or dogs). The signal peptide, which allows trafficking to the endoplasmic reticulum, is cleaved following translocation. In the endoplasmic reticulum, the polypeptide precursor undergoes post-translational modifications, namely (i) homodimerization and (ii) glycosylation, in order to achieve its native conformation. In human beings, it is a dimeric glycoprotein of 144 kDa corresponding to amino acids 26-560. Each monomer, of 72 kDa in human beings, contains the pro region (58 kDa in human beings) followed by the mature region (12 kDa in human beings). Before secretion to the extracellular medium and the blood stream, the AMH glycoprotein undergoes an ultimate post-translation maturation by cleavage. Thus, in human beings and bovines, the preprohormone is converted into prohormone by cleavage of the precursor portion. The prohormone is also cleaved between the N-terminal portion and the C-terminal portion in order to obtain the mature hormone (having a biological activity). However, these two portions remain non-covalently bonded (Zec I., et al., 2011). In human beings, variable degrees of cleavage have been reported depending on studies: between 5% and 20% by Zec et al. and 67% in boys or alternatively 81% in women by Pankhurst et al. (2016). Thus, cleaved AMH and non-cleaved AMH are found in the blood stream.

AMH is produced in males by the Sertoli cells and is involved at the beginning of its life in differentiation of the male tract. In females, AMH is produced by the granulosa cells of the growing small follicles and therefore instead intervenes starting from puberty. Thus, in women, AMH has shown itself to be of use in various fields, in particular associated with fertility (Dewailly D, et al. 2014). For example, the assaying of AMH in the circulation makes it possible to estimate the number of antral and preantral follicles present in the ovaries, independently of cycles (Dewailly D, et al., 2014). Furthermore, as an indicator of the natural reduction in the ovarian reserve and therefore of the inherent risks of hypofertility, the assaying of AMH is indicated for helping women in managing their pregnancy planning. In an assisted reproductive technology context, the assaying of AMH contributes to selecting the best strategy for the patient, by optimizing in particular the step of controlled stimulation of the ovaries while at the same time avoiding the risk of hyperstimulation (Arce J C, et al., 2014). The assaying of AMH also makes it possible to monitor the change in the ovarian reserve in young girls or women having received a gonadotropic treatment in the case of cancer for example (Chai J and Howie A F., 2014). For women who have ovulation disorders, determining the serum AMH levels makes it possible to better characterize the type of ovarian dysfunction, particularly hypergonadotropic anovulation associated with ovarian insufficiency, such as polycystic ovary syndrome (Fong S L, et al., 2015). In young boys, AMH is produced in very significant amount by the testicles of the fetus of the newborn and thus is involved early in differentiation of the male tract. Thus, assaying AMH has been found to be of use in boys before puberty, in the context of disorders associated with sexual differentiation.

The assaying of AMH is carried out by sandwich immunoassay and requires the use of a test which is at the same time sensitive, specific and reproducible. However, despite the various methods proposed in the literature (Hudson, 1990; Long, 2000) or alternatively the various kits available on the market, an assay which allies all of these characteristics is still not available. One of the major difficulties to be solved was identified as early as 1996: it is the lack of apparent stability of AMH in the biological sample. Thus, the storage conditions (time, duration, freezing cycles, etc.) can cause variations in the concentrations measured (Lee, 1996). These variations are of course an artefact and can result in an incorrect interpretation of the biological results.

Various kits have been placed on the market. The antibodies used in these kits recognize different regions of AMH. The first generation of AMH assays corresponds to the EIA/MIS/AMH kits (Immunotech) and the Active MIS/ AMH ELISA kit (DSL). The antibodies used in these kits are not identical, but each one uses a first antibody which recognizes the pro region of AMH, the other antibody recognizing the mature region. In 2010, the company Beckman Coulter, which sold them, replaced them with a second-generation kit (AMH Gen II Assay) with, according to them, improved performance levels. Indeed, according to the authors, this kit is highly specific and the AMH measured is supposedly not affected by proteolysis since the two monoclonal antibodies used each recognize the mature region (Kumar, 2015; U.S. Pat. No. 7,897,350). The authors think that the mature region, which contains several cysteine residues, is supposedly more stable than the pro region in the event of proteolysis. Once deployed in the field, in routine clinical use, it quickly turned out to be the case that the AMH Gen II kit did not live up to its promises. A broad retrospective study confirmed the lack of stability of the AMH assay from the viewpoint of the conditions for storing the sample tubes (Rustamov O, 2012) and showed that the AMH Gen II kit was extremely sensitive to these variations. Several hypotheses were put forward to explain the fluctuations observed. One of the possible interpretations could be linked to the fact that the AMH molecule undergoes conformational changes, after a blood sample has been taken, which are variable from one individual to the other.

These results were rapidly repeated and confirmed by an independent team (Han et al., 2014). Furthermore, this team described a solution for promoting AMH stability during sample storage: they performed a predilution before assaying, which makes it possible to improve the general reproducibility of the AMH assays by Gen II. However, this solution, which is admittedly easy to implement, has some drawbacks:

(i) the AMH concentrations measured after predilution are increased. This increase varies from one individual to the other (from 1.35 times to 3.06 times for the available data). It is therefore necessary to redefine the reference values experimentally, over a wide cohort, and also the clinical interpretation rules.

(ii) The dilution performed is not insignificant (⅕, i.e. 60 µl of sample in 300 µl of buffer). It admittedly makes it possible to dispense with the interferences observed, but as a result leads to a decrease in the sensitivity of the assay, which is significant for many clinical uses.

(iii) The cause of the instability of AMH has still not been identified. Consequently, it is not possible to confirm that the dilution will be able to solve the problem of a lack of stability for all samples.

Moreover, Rustamov 0 (2012) has described a decrease in the average AMH concentration measured by the AMH Gen II Assay kit and a decrease in sensitivity. Their conclusion is that it is "very dangerous to implement a stimulation protocol based on the results of the Gen II kit".

It is therefore essential to provide a robust kit, for which the AMH concentration measured is accurate and reproducible, regardless of the time between the taking of the sample and the performance of the assay, and regardless of the storage conditions (dose independent of the pre-analytical conditions).

Patent application WO 2014/074835 proposes various methods for assaying various AMH isoforms (dimeric AMH only, non-cleaved AMH, AMH cleaved then reassociated, etc.) in order to determine whether a particular isoform or the change from one isoform to another can make clinical sense. Thus, the application describes numerous antibodies directed against a large number of linear epitopes located either in the pro region or in the mature region of AMH. The authors assert that the compositions and methods disclosed correspond to the requirement of an accurate, reproducible and standardized assay. This application discloses 18 epitopes, i.e. in total 324 (18×18) ways to construct sandwich immunoassays by combining the antibodies which recognize these epitopes. Given the numerous pre-analytical problems encountered with the various AMH assays, it is difficult to believe, without experimental demonstration, that each of these epitope combinations, consequently antibody combinations, makes it possible to obtain a robust test. Moreover, no piece of data in this patent application shows that the use of the antibodies described allows an assay which can be used in common medical practice, which is robust, accurate, reproducible and standardized, and especially the result of which is independent of the pre-analytical conditions. The only data present in the application relate to stability data based on assays of "single epitope sandwich or SES" type, namely assays using the same monoclonal antibody for capture and detection. Furthermore, these tests detect exclusively the dimeric form of AMH, the clinical interest of which is at the moment unknown (since the concentrations measured are very different than the concentrations obtained with the total-AMH assays which are those used in common medical practice).

The applicant has found, unexpectedly, that it is possible to overcome the drawbacks of the prior art by preparing new antibodies which recognize only non-linear epitopes, in a particular zone of AMH located in the median portion of the pro region of AMH (between amino acids 157-255 in human beings), which antibodies make it possible to carry out a stable and reliable AMH assay which can be used in common medical practice, and which is robust, accurate and reproducible, independently of the pre-analytical or storage conditions of the sample. In choosing this particular zone of AMH, described as having a cleavage zone (WO 2014/074835), the assaying of AMH with these antibodies which recognize a non-linear epitope from the defined zone detects, surprisingly and against all expectations, all the AMH of biological interest present in a biological sample.

Thus, a first subject of the invention relates to a method for preparing anti-mammalian AMH (anti-Müllerian hormone) antibodies, characterized in that it comprises the steps of:

(i) immunizing an animal with an AMH polypeptide or a polynucleotide encoding this AMH polypeptide, said AMH polypeptide comprising at least the 99 amino acids of sequence SEQ ID No. 1 or of a sequence having at least 75% identity with the sequence SEQ ID No. 1, and at most the 560 amino acids of sequence SEQ ID No. 2 or of a sequence having at least 75% identity with the sequence SEQ ID No. 2, (ii) preparing hybridomas from the cells of a lymphoid organ of the animal having received the immunogen, (iii) selecting the hybridomas secreting antibodies recognizing an AMH polypeptide comprising at least 99 amino acids of sequence SEQ ID No. 1 or of a sequence having at least 75% identity with the sequence SEQ ID No. 1, and at most the 255 amino acids of sequence SEQ ID No. 8 or of a sequence having at least 75% identity with the sequence SEQ ID No. 8, but recognizing neither (a) an AMH polypeptide comprising at least the 131 amino acids of sequence SEQ ID No. 13 or of a sequence having at least 75% identity with the sequence SEQ ID No. 13 and at most the 156 amino acids of sequence SEQ ID No. 11 or of a sequence having at least 75% identity with the sequence SEQ ID No. 1, nor (b) any linear epitope located in the sequence SEQ ID No. 1 or a sequence having at least 75% identity with the sequence SEQ ID No. 1, and (iv) producing the antibodies.

A second subject of the invention relates to the anti-mammalian AMH monoclonal antibodies or monoclonal antibody fragments recognizing an AMH polypeptide comprising at least the 99 amino acids of sequence SEQ ID No. 1 or of a sequence having at least 75% identity with the sequence SEQ ID NO. 1, and at most the 255 amino acids of sequence SEQ ID No. 8 or of a sequence having at least 75% identity with the sequence SEQ ID No. 8, but recognizing neither (a) an AMH polypeptide comprising at least the 131 amino acids of sequence SEQ ID No. 13 or of a sequence having at least 75% identity with the sequence SEQ ID No. 13 and at most the 156 amino acids of sequence SEQ ID No. 11 or of a sequence having at least 75% identity with the sequence SEQ ID No. 11, nor any linear epitope located in the sequence SEQ ID No. 1 or a sequence having at least 75% identity with the sequence SEQ ID No. 1.

A third subject of the invention relates to conjugates comprising (i) an anti-AMH monoclonal antibody or monoclonal antibody fragment as defined above or prepared according to the method as defined above and (ii) a label capable of generating the emission of a detectable signal for the visualization of an immunological reaction between this conjugate and the AMH of a biological sample.

A fourth subject of the invention relates to a method for quantifying mammalian AMH by sandwich immunoassay, in a biological sample which may contain AMH, which comprises the following steps:

bringing said biological sample into contact with two AMH-binding partners, at least one of said partners of which is an antibody or antibody fragment as defined above or as prepared according to the method as defined above, or else a conjugate as defined above, detecting a signal emitted by the binding between said binding partners and the AMH, if it is present, using a label capable of emitting a detectable signal, and converting the signal detected into an AMH concentration.

A fifth subject of the invention relates to the use of a method for quantifying AMH as defined above, as an aid for the diagnosis of disorders associated with an ovarian dysfunction in women of child-bearing age or as an aid for the evaluation of the ovarian follicular reserve in young girls over the age of 12 and women, or else as an aid for the evaluation of disorders associated with sexual differentiation in boys before puberty.

Finally, a last subject of the invention relates to a kit comprising an antibody or antibody fragment as defined above or as prepared according to the method as defined above, or else a conjugate as defined above.

The applicant has found, unexpectedly, that the use of the median portion of the pro region of AMH for selecting anti-AMH monoclonal antibodies during their preparation process, while at the same time discarding the antibodies which recognize linear epitopes on this portion, makes it possible, when these antibodies thus selected are used for assaying AMH, to have a reliable and reproducible assay.

An epitope, also known as antigenic determinant, is the smallest portion of an antigen that can be recognized by a paratope, which is the variable portion of an antibody. The structure of the epitope is complementary with the paratope of the antibody. The structure involved may be the primary structure, in the case of a linear epitope, also known as sequential epitope or continuous epitope since it comprises consecutive amino acids, or the tertiary structure in the case of a discontinuous epitope, also known as non-linear epitope. When the antigen is of protein nature, as in the present case, the linear epitopes correspond to a peptide sequence of variable length.

The sequence of a linear epitope can comprise "conservative" modifications which do not significantly change the binding between the epitope and the antibody from a specificity point of view.

The antibodies prepared according to the method of the invention do not therefore recognize linear epitopes on the median portion of the pro region of AMH, but do recognize this median portion.

The expression "monoclonal antibodies recognizing the median portion of the pro region of AMH" is intended to mean that the antibodies are capable of binding to AMH when this portion is present, for instance to whole AMH, but are not capable of binding to an AMH polypeptide when this portion is absent.

Without wishing to be bound by a theory, one hypothesis aposteriori would consist in thinking that the median portion of the pro region of AMH against which the antibodies are directed might correspond to a zone in which AMH would undergo proteolysis in the biological sample in which it is assayed, for example plasma, such that this zone would remain clearly presented in its conformation of origin, or else that its conformation would not be affected by modifications which might affect surrounding zones of the molecule.

The mammals for which it is desired to produce antibodies directed against their median portion of the pro region of their AMH are any mammal for which the assaying of AMH constitutes an aid. By way of example, mention may be made of human beings (women and men, including boys), horses (in particular mares), dogs (in particular bitches), bovines, members of the ovine race, and the cat family.

The AMH secreted by mammals are not identical, but are close. At least 75% sequence identity is observed between human AMH and the AMHs of the other mammals for which the assaying of AMH constitutes an aid. The AMH taken as a reference in the invention will be human AMH.

The terms "identity" or "percentage identity" in the context of two or more polypeptide sequences signify that the two sequences compared have a specified percentage of amino acid residues which are the same over the maximum length that could be aligned, when they are aligned for maximum correspondence. Such alignments and calculations of the percentage identity can be carried out using sequence comparison algorithms and/or software (Emboss Needle, LAlign, Blast, Clustal, etc.) or by visual inspection in simple cases.

As previously indicated, AMH consists of a pro region and a mature region. In human beings, the pro region ends in position 451 and the mature region begins in position 452. The median portion of the pro region of AMH recognized by the antibodies prepared according to the invention begins, in human beings, in position 157 and ends in position 255. It consists of the 99 amino acids of the sequence SEQ ID No. 1. In horses, the median portion of the pro region of AMH recognized by the antibodies prepared according to the invention begins in position 167, ends in position 265 and corresponds to the 99 amino acids of sequence SEQ ID No. 14. The median portion of the pro region of canine AMH recognized by the antibodies prepared according to the invention begins, for its part, in position 166, ends in position 264 and corresponds to the 99 amino acids of sequence SEQ ID No. 23. As regards bovines, the median portion of the pro region of AMH recognized by the antibodies prepared according to the invention begins in position 171, ends in position 270 and corresponds to the 100 amino acids of sequence SEQ ID No. 32.

In order to produce these particular and advantageous anti-AMH antibodies, the method of the invention comprises, as first step, immunizing an animal with an immunogen. This immunogen is an AMH polypeptide or a polynucleotide encoding this AMH polypeptide, which must comprise at least the zone that the antibodies must recognize, namely at least the median portion of the pro region of AMH. Thus, the immunogen used comprises at least the 99 amino acids of sequence SEQ ID No. 1 or of a sequence having at least 75% identity with the sequence SEQ ID No. 1.

The immunogen also comprises at most the whole AMH of the species in question or the polynucleotide encoding the whole AMH of the species in question, namely, in the case of human AMH, the 560 amino acids of sequence SEQ ID No. 2 (Uniprot accession No. KB F2YMM5), the other AMHs comprising at least 75% identity with the sequence SEQ ID No. 2. For example, the equine total-AMH polypeptide comprises the 573 amino acids of sequence SEQ ID No. 15 (Uniprot accession No. KB F2YMM5), the canine total-AMH polypeptide comprises the 572 amino acids of sequence SEQ ID No. 24 (Uniprot accession No. KB A0A0E3N0I3) and the bovine total-AMH polypeptide (Uniprot accession No. KB P03972) comprises the 575 amino acids of sequence SEQ ID No. 33.

According to one particular embodiment, the immunogen used is an AMH polypeptide, or a polynucleotide encoding this polypeptide, devoid, relative to the whole AMH sequence, of all the amino acids located after the median portion of the pro region of AMH, namely an AMH polypeptide, or a polynucleotide encoding said AMH polypeptide, comprising at least the 230 amino acids of sequence SEQ ID No. 10 or of a sequence having at least 75% identity with the sequence SEQ ID No. 10 and at most the 255 amino acids of sequence SEQ ID No. 8 or of a sequence having at least 75% identity with the sequence SEQ ID No. 8, preferably chosen from the AMH polypeptides of sequences SEQ ID No. 8, SEQ ID No. 9 and SEQ ID No. 10 or of sequences having at least 75% identity with these sequences. The sequence SEQ ID No. 8 corresponds to amino acids 1-255 of human AMH (called AMH-2), the sequence SEQ ID No. 9 corresponds to amino acids 19-255 of human AMH, namely the sequence SEQ ID No. 8 without the signal peptide (called AMH-2 without signal peptide) and the sequence SEQ ID No. 10 corresponds to amino acids 26-255 of human AMH, namely the sequence SEQ ID No. 8 without the signal peptide or the precursor portion (called AMH-2 without signal peptide or precursor portion).

According to another embodiment, the immunogen used is an AMH polypeptide, or a polynucleotide encoding this polypeptide, which corresponds to total AMH, with all or part of the signal peptide and optionally all or part of the precursor portion. Thus, the AMH polypeptide comprises at least the 535 amino acids of sequence SEQ ID No. 4 or of a sequence having at least 75% identity with the sequence SEQ ID No. 4, preferably chosen from the AMH polypeptides of sequences SEQ ID No. 2, SEQ ID No. 3 and SEQ ID No. 4 or of sequences having at least 75% identity with these sequences. The sequence SEQ ID No. 2 corresponds to amino acids 1-560 of human AMH, the sequence SEQ ID No. 3 corresponds to amino acids 19-560 of human AMH, namely the sequence SEQ ID No. 2 without the signal peptide, and the sequence SEQ ID No. 3 corresponds to amino acids 26-560 of human AMH, namely the sequence SEQ ID No. 2 without the signal peptide or the precursor portion.

According to another embodiment, the immunogen used is an AMH polypeptide, or a polynucleotide encoding this polypeptide, which corresponds to the total AMH, with all or part of the signal peptide and optionally all or part of the precursor portion, but without the mature region. Thus, the AMH polypeptide comprises at least the 426 amino acids of sequence SEQ ID No. 7 or of a sequence having at least 75% identity with the sequence SEQ ID No. 7 and at most the 451 amino acids of sequence SEQ ID No. 5 or of a sequence having at least 75% identity with the sequence SEQ ID No. 5, preferably chosen from the AMH polypeptides of sequences SEQ ID No. 5, SEQ ID No. 6 and SEQ ID No. 7 or of sequences having at least 75% identity with these sequences. The sequence SEQ ID No. 5 corresponds to amino acids 1-451 of human AMH (called AMH-3), the sequence SEQ ID No. 6 corresponds to amino acids 19-451 of human AMH, namely the sequence SEQ ID No. 5 without the signal peptide (called AMH-3 without signal peptide) and the sequence SEQ ID No. 7 corresponds to amino acids 26-451 of human AMH, namely the sequence SEQ ID No. 5 without the signal peptide or the precursor portion (called AMH-3 without signal peptide or precursor portion).

The table below (table 1) presents various AMH polypeptides that are of use in the context of the invention, in particular as immunogen for some, giving the position of the amino acids and the corresponding SEQ IDs (between parentheses) according to the species of mammal.

TABLE 1

|  | Human | Equine | Canine | Bovine |
|---|---|---|---|---|
| Median portion of the pro region of AMH | 157-255 (SEQ ID No. 1) | 167-265 (SEQ ID No. 14) | 166-264 (SEQ ID No. 23) | 171-270 (SEQ ID No. 32) |
| Total AMH | 1-560 (SEQ ID No. 2) | 1-573 (SEQ ID No. 15) | 1-572 (SEQ ID No. 24) | 1-575 (SEQ ID No. 33) |
| Total AMH without signal peptide | 19-560 (SEQ ID No. 3) | 23-573 (SEQ ID No. 16) | 22-572 (SEQ ID No. 25) | 18-575 (SEQ ID No. 34) |
| Total AMH without signal peptide or precursor portion | 26-560 (SEQ ID No. 4) | NA | NA | 25-575 (SEQ ID No. 35) |
| Total AMH-3 | 1-451 (SEQ ID No. 5) | 1-464 (SEQ ID No. 17) | 1-463 (SEQ ID No. 26) | 1-466 (SEQ ID No. 36) |
| Total AMH-3 without signal peptide | 19-451 (SEQ ID No. 6) | 23-464 (SEQ ID No. 18) | 22-463 (SEQ ID No. 27) | 18-466 (SEQ ID No. 37) |
| Total AMH-3 without signal peptide or precursor portion | 26-451 (SEQ ID No. 7) | NA | NA | 25-466 (SEQ ID No. 38) |
| Total AMH-2 | 1-255 (SEQ ID ) No. 8 | 1-265 (SEQ ID No. 19) | 1-264 (SEQ ID No. 28) | 1-270 (SEQ ID No. 39) |
| Total AMH-2 without signal peptide | 19-255 (SEQ ID No. 9) | 23-265 (SEQ ID No. 20 | 22-264 (SEQ ID No. 29) | 18-270 (SEQ ID No. 40) |
| Total AMH-2 without signal peptide or precursor portion | 26-255 (SEQ ID No. 10) | NA | NA | 25-270 (SEQ ID No. 41) |

NA = Not Applicable since no precursor portion in the AMR in question

Of course, in addition to the amino acids described in these sequences, the immunogen, when it is in polypeptide form, can also comprise other amino acids used for the production of the polypeptide and the purification thereof, for instance a polyhistidine tail.

The methods for producing polypeptides are widely known to those skilled in the art. For example, the AMH polypeptides can be obtained by genetic engineering using steps, conventionally known to those skilled in the art, consisting in:

having available the DNA encoding the AMH polypeptides, said DNA being obtained according to conventional methods, inserting this DNA, by cloning, into an expression vector such as a plasmid, a cosmid, a λ phage or a viral vector (baculovirus (Autographa californica Nuclear Polyhedrosis Virus), vaccinia virus, Semliki forest virus, adenovirus virus, lentivirus virus, etc.), which vector also comprises an origin of replication (for plasmids or cosmids) or a replication system allowing its amplification in the host cell and one or more promoters allowing the transcription of messenger RNAs which will be translated into proteins, introducing the vector with the gene of interest for expression into a host cell, such as a prokaryotic cell (for example a bacterium, for instance *Escherichia coli, Bacillus subtilis*) by transformation or infection, or a eukaryotic cell (for example yeasts (*Saccharomyces cerevisiae, Pichia pastoris*), insect cells (Sf9, Sf21, High5 cells), mammalian cells (CHO, 293, Per.C6, BHK-21, Vero, etc.) by transient or permanent transfection, or else viral infection, culturing and optionally multiplying the host cell containing the expression vector with optionally amplification of the vector in the host cell, as required, inducing transcription and protein synthesis for the production of the recombinant AMH polypeptides, and purifying so as to extract said polypeptides, for example by means of a polyhistidine tail. The polypeptides are then termed recombinant.

When the immunogen is a polynucleotide, the same DNA as that which would be used to prepare the AMH polypeptide by genetic engineering will for example be used.

The animal used for the immunization is any animal normally used for obtaining monoclonal antibodies, such as for example a mouse, a rat, a rabbit, a goat or sheep.

The conditions and parameters for the immunization, such as immunogen concentration, immunization mode, etc., are widely known to those skilled in the art who will be able to refer to the procedures described by Köhler and Milstein, as early as 1975, and in particular in the manual Current protocols in Cell Biology (Yokoyama W M, 2001).

The second step of the method of the invention is a conventional step and consists in preparing the hybridomas from the cells of a lymphoid organ of the animal having received the immunogen, such as for example the spline, the lymph nodes and the tonsils. Such a step is described in any monoclonal antibody production manual. However, it is necessary to use the fusion partner suitable for each species. Thus, for example, for mice, the cGPS CHO-Sa line can be used, for rabbits the 240E-W line can be used (U.S. Pat. No. 7,429,487) and for sheep the SFP1 line can be used (WO 92/15699).

The third step of the method consists of the particular selection of the hybridomas obtained. To do this, hybridomas are first of all cultured in an appropriate medium, as well known to those skilled in the art, comprising in particular nutrients for their multiplication, and growth stimulators. The clones secreting the antibodies of interest are then selected using the antigen recognized by the antibodies, according to techniques known to those skilled in the art such as direct detection without label (spontaneous precipitation after antigen-antibody reaction), indirect detection (for example ELISA or other type of immunoassay), surface plasmon resonance (BIAcore®) and interferometry (Octet). The originality of this step consists of the particular selection of the hybridomas which can be carried out in 2 successive screenings, in any order, with particular polypeptides and peptides.

The first screening, called screening 1, consists in retaining only the hybridomas which produce antibodies recognizing the median portion of the pro region, as previously described, said zone being known to nevertheless have a cleavage site, which should be excluded. To do this, two methods are possible:

Method 1:

The hybridomas secreting antibodies recognizing AMH-2, namely, for human AMH-2, amino acids 1-255 (SEQ ID No. 8), where appropriate without all or part of the signal peptide and all or part of the precursor portion, or any sequence having at least 75% identity with this sequence, are first of all selected. According to one embodiment, the AMH-2 polypeptide recognized by the antibodies is a polypeptide of sequences chosen from SEQ ID No. 8, SEQ ID No. 9 and SEQ ID No. 10 and of sequences having at least 75% identity with these sequences.

The hybridomas which produce antibodies recognizing the portion of AMH located before the median portion of the pro region of AMH, namely, for human AMH, amino acids 1-156 (SEQ ID No. 11), where appropriate without all or part of the signal peptide and all or part of the precursor portion, and any sequence having at least 75% identity with this sequence, is then discarded. This AMH polypeptide is called AMH polypeptide (a) not recognized by the antibodies prepared according to the invention. According to one embodiment, the AMH polypeptide (a) not recognized by the antibodies is a polypeptide of sequences chosen from: SEQ ID No. 11, SEQ ID No. 12 and SEQ ID No. 13 and of sequences having at least 75% identity with these sequences. The sequence SEQ ID No. 11 corresponds to amino acids 1-156 of human AMH (called AMH-1), the sequence SEQ ID No. 12 corresponds to amino acids 19-156 of human AMH, namely the sequence SEQ ID No. 11 without the signal peptide (called AMH-1 without signal peptide) and the sequence SEQ ID No. 13 corresponds to amino acids 26-156 of human AMH, namely the sequence SEQ ID No. 11 without the signal peptide or the precursor portion (called AMH-1 without signal peptide or precursor portion).

Method 2:

The hybridomas secreting antibodies recognizing the median portion of the pro region of AMH, namely, for human AMH, amino acids 157-255 (SEQ ID No. 1) and any sequence having at least 75% identity with this sequence, are selected.

The table below (table 2) presents various AMH polypeptides (a), which are not recognized, and which are of use in the context of the invention, giving the position of the amino acids and the corresponding SEQ IDs (between parentheses) according to the species of mammal.

TABLE 2

|  | Human | Equine | Canine | Bovine |
| --- | --- | --- | --- | --- |
| Total AMH-1 | 1-156 (SEQ ID No. 11) | 1-166 (SEQ ID No. 21) | 1-165 (SEQ ID No. 30) | 1-170 (SEQ ID No. 42) |
| Total AMH-1 without signal peptide | 19-156 (SEQ ID No. 12) | 23-166 (SEQ ID No. 22) | 22-165 (SEQ ID No. 31) | 18-170 (SEQ ID No. 43) |

TABLE 2-continued

| | Human | Equine | Canine | Bovine |
|---|---|---|---|---|
| Total AMH-1 without signal peptide or precursor portion | 26-156 (SEQ ID No. 13) | NA | NA | 25-170 (SEQ ID No. 44) |

NA = Not Applicable since no precursor portion in the AMH in question

Thus, according to one particular embodiment, the sequences having at least 75% identity with the sequences SEQ ID No. 11, SEQ ID No. 12, and SEQ ID No. 13 are chosen from the sequences: SEQ ID NO. 21, SEQ ID NO. 22, SEQ ID No. 30, SEQ ID No. 31, SEQ ID No. 42, SEQ ID No. 43 and SEQ ID No. 44.

The AMH polypeptides (a) can be prepared as previously described and can comprise other amino acids not belonging to The second screening, called screening 2, consists in discarding the hybridomas which produce antibodies which recognize linear epitopes in the median portion of the pro region of AMH, namely in the sequence SEQ ID No. 1 or any sequence having 75% identity with the sequence SEQ ID No. 1. These epitopes are called linear epitopes (b).

The determination of linear epitopes on an amino acid sequence is well known to those skilled in the art. It consists in cutting the sequence of interest into overlapping peptides of given length, for example of 10, 12 or 15 amino acids, then identifying, among these peptides, those which are recognized by monoclonal or polyclonal antibodies. Of course, by virtue of their definition, the linear epitopes have consecutive amino acids of the sequence of interest.

The table below (table 3) presents various linear epitopes (b) determined in the median portion of the pro region of AMH, that are of use in the context of the invention, giving the SEQ IDs according to the species of mammal.

TABLE 3

| | Human | Equine | Canine | Bovine |
|---|---|---|---|---|
| Linear epitopes on the median portion of the pro region | SEQ ID No. 45 SEQ ID No. 46 SEQ ID No. 47 | SEQ ID No. 48 SEQ ID No. 49 SEQ ID No. 50 | SEQ ID No. 51 SEQ ID No. 52 SEQ ID No. 53 | SEQ ID No. 54 SEQ ID No. 55 SEQ ID No. 56 |

Thus, according to one embodiment, the linear epitopes (b) not recognized by the antibodies have the sequences SEQ ID No. 45 to SEQ ID No. 56.

As previously, the epitopes are produced according to conventional methods, as previously described. They can also be produced by peptide synthesis, which is often preferred.

One particular embodiment comprises at least characteristics as follow for the selection step (iii):
screening 1 uses method 1;
screening 1 is carried out before screening 2.

Between each screening step, if required, the antibodies contained in the hybridoma supernatants are purified according to conventional techniques, for instance affinity chromatography on protein A. Once the selection has been carried out and/or if required, between each screening step, the hybridomas are cloned in order to guarantee a stabilized and homogeneous line. This is widely known to those skilled in the art.

The last step of the method of the invention consists of the production of the antibodies of interest, a step which is also well known to those skilled in the art and described in all the monoclonal antibody production manuals, for example the manual Current Protocols in Cell Biology.

In addition to the above steps, the general procedure of which has been widely described, the method of the invention can also comprise other steps, such as steps for washing, storage and conversion of the antibodies into fragments.

In the method for preparing anti-AMH antibodies of the invention, the immunogen (AMH polypeptide or polynucleotide encoding this polypeptide comprising at least the 99 amino acids of sequence SEQ ID No. 1 or of a sequence having at least 75% identity with the sequence SEQ ID No. 1, and at most the 560 amino acids of sequence SEQ ID No. 2 or of a sequence having at least 75% identity with the sequence SEQ ID No. 2), the median portion of the pro region of AMH (AMH polypeptide comprising at least the 99 amino acids of sequence SEQ ID No. 1, or of a sequence having at least 75% identity with the sequence SEQ ID No. 1, and at most the 255 amino acids of sequence SEQ ID No. 8 or of a sequence having at least 75% identity with the sequence SEQ ID No. 8), the polypeptide (a) not recognized by the antibodies of interest (AMH polypeptide comprising at least the 131 amino acids of sequence SEQ ID No. 13 or of a sequence having at least 75% identity with the sequence SEQ ID No. 13, and at most the 156 amino acids of sequence SEQ ID No. 11 or of a sequence having at least 75% identity with the sequence SEQ ID No. 11) and the linear epitopes (located in sequence SEQ ID No. 1 or a sequence having at least 75% identity with the sequence SEQ ID No. 1) preferably belong to the same species.

According to one embodiment:
the mammal is a human being, the immunogen is an AMH peptide, or a polynucleotide encoding this AMH polypeptide, which comprises at least the 99 amino acids of sequence SEQ ID No. 1 and at most the 560 amino acids of sequence SEQ ID No. 2, the AMH polypeptide recognized by the antibodies secreted by the hybridomas is an AMH polypeptide comprising at least the 99 amino acids of sequence SEQ ID No. 1 and at most the 255 amino acids of sequence SEQ ID No. 8, and the AMH polypeptide (a) not recognized by the antibodies secreted by the hybridomas is an AMH polypeptide comprising at least the 131 amino acids of sequence SEQ ID No. 13 and at most the 156 amino acids of sequence SEQ ID No. 11, or the mammal is the horse, the immunogen is an AMH polypeptide, or a polynucleotide encoding this AMH polypeptide, which comprises at least the 99 amino acids of sequence SEQ ID No. 14 and at most the 573 amino acids of sequence SEQ ID No. 15, the AMH polypeptide recognized by the antibodies secreted by the hybridomas is an AMH polypeptide comprising at least the 99 amino acids of sequence SEQ ID No. 14 and at most the 265 amino acids of sequence SEQ ID No. 19, and the AMH polypeptide (a) not recognized by the antibodies secreted by the hybridomas is an AMH polypeptide comprising at least the 144 amino acids of sequence SEQ ID No. 22 and at most the 166 amino acids of sequence SEQ ID No. 21, or the mammal is the dog, the immunogen is an AMH polypeptide, or a polynucleotide encoding this AMH polypeptide, which comprises at least the 99 amino acids of sequence SEQ ID No. 23 and at most the 572 amino acids of sequence SEQ ID No. 24, the AMH polypeptide recognized by the antibodies secreted by the hybridomas is an AMH polypeptide comprising at least the 99 amino acids of sequence SEQ ID No. 23 and at most the 264 amino acids of sequence SEQ ID No. 28, and the AMH polypeptide (a) not recognized by the antibodies secreted by the hybridomas is an AMH polypeptide comprising at least the 144 amino acids of sequence SEQ ID No. 31 and at most the 165 amino acids of sequence SEQ ID No. 30, or the mammal is a bovine, the immunogen is an AMH polypeptide, or a polynucleotide encoding this AMH polypeptide, which comprises at least the 100 amino acids of sequence SEQ ID No. 32 and at most the 575 amino acids of sequence SEQ ID No. 33, the AMH polypeptide recognized by the antibodies secreted by the hybridomas is an AMH polypeptide comprising at least the 100 amino acids of sequence SEQ ID No. 32 and at most the 270 amino acids of sequence SEQ ID No. 39, and the AMH polypeptide (a) not recognized by the antibodies secreted by the hybridomas is an AMH polypeptide comprising at least the 146 amino acids of sequence SEQ ID No. 44 and at most the 270 amino acids of sequence SEQ ID No. 42.

In particular:

the mammal is a human being, the immunogen is an AMH polypeptide, or a polynucleotide encoding this AMH polypeptide, chosen from the polypeptides of sequence SEQ ID Nos 2 to 10, the AMH polypeptide recognized by the antibodies secreted by the hybridomas is an AMH polypeptide chosen from the polypeptides of sequence SEQ ID No. 1 and SEQ ID Nos 8 to 10, and the AMH polypeptide (a) not recognized by the antibodies secreted by the hybridomas is an AMH polypeptide chosen from the polypeptides of sequence SEQ ID Nos 11 to 13, or the mammal is the horse, the immunogen is an AMH polypeptide, or a polynucleotide encoding this AMH polypeptide, chosen from the polypeptides of sequence SEQ ID Nos 15 to 20, the AMH polypeptide recognized by the antibodies secreted by the hybridomas is an AMH polypeptide chosen from the polypeptides of sequence SEQ ID No. 14 and SEQ ID Nos 19 and 20, and the AMH polypeptide (a) not recognized by the antibodies secreted by the hybridomas is an AMH polypeptide chosen from the polypeptides of sequence SEQ ID Nos 21 and 22, or the mammal is the dog, the immunogen is an AMH polypeptide, or a polynucleotide encoding this AMH polypeptide, chosen from the polypeptides of sequence SEQ ID Nos 24 to 29, the AMH polypeptide recognized by the antibodies secreted by the hybridomas is an AMH polypeptide chosen from the polypeptides of sequence SEQ ID No. 23 and SEQ ID Nos 28 and 29, and the AMH polypeptide (a) not recognized by the antibodies secreted by the hybridomas is an AMH polypeptide chosen from the polypeptides of sequence SEQ ID Nos 30 and 31, or the mammal is a bovine, the immunogen is an AMH polypeptide, or a polynucleotide encoding this AMH polypeptide, chosen from the polypeptides of sequence SEQ ID Nos 33 to 41, the AMH polypeptide recognized by the antibodies secreted by the hybridomas is an AMH polypeptide chosen from the polypeptides of sequence SEQ ID No. 32 and SEQ ID Nos 39 to 41, and the AMH polypeptide (a) not recognized by the antibodies secreted by the hybridomas is an AMH polypeptide chosen from the polypeptides of sequence SEQ ID Nos 42 to 44.

The antibodies, produced by means of the method of the invention, are novel and can be produced by another method, as long as they keep the same characteristics. Thus, another subject of the invention relates to the anti-mammalian AMH monoclonal antibodies or antibody fragments recognizing an AMH polypeptide comprising at least the 99 amino acids of sequence SEQ ID No. 1 or of a sequence having at least 75% identity with the sequence SEQ ID No. 1, and at most the 255 amino acids of sequence SEQ ID No. 8 or of a sequence having at least 75% identity with the sequence SEQ ID No. 8, but recognizing neither (a) an AMH polypeptide comprising at least the 131 amino acids of sequence SEQ ID No. 13 or of a sequence having at least 75% identity with the sequence SEQ ID No. 13, and at most the 156 amino acids of sequence SEQ ID No. 11 or of a sequence having at least 75% identity with the sequence SEQ ID No. 11, nor any linear epitope located in the sequence SEQ ID No. 1 or a sequence having at least 75% identity with the sequence SEQ ID No. 1.

The term "monoclonal antibody fragment" is intended to mean any portion of the antibody which has the same immunological recognition characteristics as the antibody from which it is derived; in the present case, it is capable of recognizing the median portion of the pro region of AMH and also the whole AMH. By way of examples of fragments, mention may be made of the Fab, Fab' and F(ab')2 fragments and also the scFv (single chain variable fragment) and dsFv (double-stranded variable fragment) fragments. These functional fragments can in particular be obtained by genetic engineering or else by specific proteolytic digestion and then purification.

The characteristics and definitions previously described for the method of the invention also apply to the antibodies of the invention.

Thus, the antibodies of the invention can meet one or more of the following conditions:

the AMH polypeptide (a) not recognized is a polypeptide of sequences chosen from: SEQ ID No. 11, SEQ ID No. 12 and SEQ ID No. 13 or of sequences having at least 75% identity with these sequences, the sequences having at least 75% identity with the sequences SEQ ID No. 11, SEQ ID No. 12 and SEQ ID No. 13 are chosen from the sequences: SEQ ID No. 21, SEQ ID No. 22, SEQ ID No. 30, SEQ ID No. 31, SEQ ID No. 42, SEQ ID No. 43 and SEQ ID No. 44, the linear epitopes (b) not recognized by the antibodies have the sequences SEQ ID No. 45 to SEQ ID No. 56.

In particular, the mammal is a human being, the AMH polypeptide recognized is an AMH polypeptide comprising at least the 99 amino acids of sequence SEQ ID No. 1 and at most the 255 amino acids of sequence SEQ ID No. 8, and the AMH polypeptide (a) not recognized is an AMH polypeptide comprising at least the 131 amino acids of sequence SEQ ID No. 13 and at most the 156 amino acids of sequence SEQ ID No. 11, or the mammal is the horse, the AMH polypeptide recognized is an AMH polypeptide comprising at least the 99 amino acids of sequence SEQ ID No. 14 and at most the 265 amino acids of sequence SEQ ID No. 19, and the AMH polypeptide (a) not recognized is an AMH polypeptide comprising at least the 144 amino acids of sequence SEQ ID No. 22 and at most the 166 amino acids of sequence SEQ ID No. 21, or the mammal is the dog, the AMH polypeptide recognized is an AMH polypeptide comprising at least the 99 amino acids of sequence SEQ ID No. 23 and at most the 264 amino acids of sequence SEQ ID No. 28, and the AMH polypeptide (a) not recognized is an AMH polypeptide comprising at least the 144 amino acids of sequence SEQ ID No. 31 and at most the 165 amino acids of sequence SEQ ID No. 30, or the mammal is a bovine, the AMH polypeptide recognized is an AMH polypeptide comprising at least the 100 amino acids of sequence SEQ ID No. 32 and at most the 270 amino acids of sequence SEQ ID No. 39, and the AMH polypeptide (a) not recognized is an AMH polypeptide comprising at least the 146 amino acids of sequence SEQ ID No. 44 and at most the 270 amino acids of sequence SEQ ID No. 42.

The anti-AMH antibodies of the invention are particularly of use for the assaying of AMH in a biological sample which may contain AMH. They can be used as they are, in whole or fragment form, and/or in a form conjugated with a label capable of generating the emission of a detectable signal for the visualization of an immunological reaction after binding with the AMH of the sample, thereby constituting another subject of the invention.

The expression label capable of generating the emission of a detectable signal for the visualization of an immunological reaction is intended to mean any molecule containing a group that reacts with a group of the antibody or of the antibody fragment, directly without chemical modification, or after chemical modification to include such a group, which molecule is capable of directly or indirectly generating a detectable signal that will be used to give the amount sought.

The binding between the label and the antibody or antibody fragment of the invention can be carried out by any method known to those skilled in the art, and in particular by coupling.

Examples of labels comprise in particular:
enzymes which produce a signal that can be detected for example by colorimetry, fluorescence or luminescence, such as horseradish peroxidase, alkaline phosphatase, β-galactosidase or glucose-6-phosphate dehydrogenase, chromophores, such as fluorescent, luminescent or dye compounds, radioactive molecules, such as P32, S35 or 1125, fluorescent molecules, such as Alexas or phycocyanines, and electrochemiluminescent salts, such as acridinium-based or ruthenium-based organometallic derivatives.

Examples of indirect detection systems comprise for example ligands capable of reacting with an anti-ligand. The ligand then corresponds to the label so as to constitute, with the antibody or antibody fragment, the conjugate.

The ligand/anti-ligand pairs are well known to those skilled in the art, and comprise for example the following pairs: biotin/streptavidin, hapten/antibody, antigen/antibody, peptide/antibody, sugar/lectin, polynucleotide/sequence complementary to the polynucleotide.

The anti-ligand can then be directly detectable by the direct detection labels previously described or can itself be detectable by another ligand/anti-ligand pair, and so on.

The assaying of the AMH is carried out by sandwich immunoassay, which is an assay widely known to those skilled in the art. Briefly, it consists in determining an analyte, in the present case the mammalian AMH, using two analyte-binding partners, in the present case at least one antibody or antibody fragment of the invention.

Of course, the prefix "immuno" in the term "immunoassay", for example, should not be taken in the present application as strictly indicating that the binding partner, other than the antibody or antibody fragment of the invention, is necessarily a partner of immunological origin, such as an antibody or antibody fragment. Indeed, as is well known to those skilled in the art, this term is more widely used to also denote tests and methods in which the binding partner is not a partner of immunological origin/nature, but consists, for example, of a receptor of the analyte that it is desired to detect and/or quantify. The essential condition is that the binding partner in question is capable of binding to the analyte sought, in the present case the AMH, preferably specifically. Thus, it is known practice to use the term ELISA assay for assays which use binding partners that are not immunological in the strict sense, more widely referred to as "ligand binding assay", although the term "immuno" is included in the name in extenso corresponding to the acronym ELISA. In the interests of clarity and uniformity, the term "immuno" is employed in the present application to denote any biological analysis using at least one binding partner suitable for binding to the analyte sought and for quantifying the latter, preferably specifically, even when the binding partner other than the antibody or antibody fragment of the invention is not immunological in nature or origin in the strict sense.

Another subject of the invention thus relates to a method for quantifying mammalian AMH by sandwich immunoassay, in a biological sample which may contain AMH, which comprises or consists of the following steps:

bringing said biological sample into contact with two AMH-binding partners, at least one of said partners of which is an antibody, an antibody fragment or a conjugate of the invention, detecting a signal emitted by the binding between said binding partners and the AMH, if it is present, using a label capable of generating the emission of a detectable signal, and converting the signal detected into an AMH concentration.

The first step of this quantification method comprises or consists of bringing a biological sample into contact with two AMH-binding partners, at least one of said partners of which is an antibody, an antibody fragment or a conjugate of the invention.

The biological samples which may contain mammalian AMH are blood, serum, plasma, follicular fluid and sperm samples. According to one embodiment, the biological sample is a blood, serum or plasma sample.

The binding partner other than the antibody or antibody fragment of the invention, optionally in the form of a conjugate, comprises any molecule capable of binding to the AMH. By way of example of such a binding partner, mention may be made of anti-AMH polyclonal antibodies, anti-AMH monoclonal antibodies, anti-AMH monoclonal antibody fragments, antibody analogs (molecules capable of mimicking antibodies) such as nanofitins, aptamers or else "DARPins", or any other molecule which is known to have an interaction with AMH.

The nanofitin antibody analogs are small proteins which, like antibodies, are capable of binding to a biological target, thus making it possible to detect it, to capture it or quite simply to target it within an organism.

The aptamer antibody analogs are oligonucleotides, generally RNA or DNA, identified in libraries containing up to 1015 different sequences, by a combinatory method of in vitro selection known as SELEX for "Systematic Evolution of Ligands by Exponential Enrichment" (Ellington A D and Szostak J W., 1990). Most aptamers are composed of RNA, because of the capacity of RNA to adopt varied and complex structures, which makes it possible to create, at its surface, cavities of varied geometries, making it possible to bind various ligands. They are biochemical tools of interest which can be used in biotechnological, diagnostic or therapeutic applications. Their selectivity and their ligand-binding properties are comparable to those of antibodies.

The "DARPins" antibody analogs, DARPins referring to Designed Ankyrin Repeat ProteINS (Boersma Y L and Plütckthun A, 2011), are another class of proteins making it possible to mimic antibodies and to be able to bind with high affinity and high selectivity to target proteins. They derive from the family of ankyrin proteins which are adapter proteins making it possible to bind integral membrane proteins to the spectrin/actin network which constitutes the "vertebral column" of the cell plasma membrane. The structure of ankyrins is based on the repetition of a motif of around 33 amino acids and the same is true for DARPins. Each motif has a secondary structure of helix-turn-helix type. DARPins contain at least three, preferably four to five, repeat units and are obtained by screening combinatorial libraries.

The anti-AMH polyclonal antibodies, monoclonal antibodies and antibody fragments can be prepared in a conventional manner widely known to those skilled in the art. Some antibodies are available on the market, for instance from AnshLabs (US).

The applicant has also prepared other monoclonal antibodies that are particularly of use in the context of the assaying of AMH using the same method for preparing monoclonal antibodies as that described previously for the invention, with the sole difference being that the antibody recognition zone is the C-terminal portion of the pro region of AMH, namely, for human AMH, amino acids 256 to 451 (196 amino acids SEQ ID No. 57); for equine AMH, amino acids 266 to 464 (199 amino acids SEQ ID No. 58), for canine AMH, amino acids 265 to 463 (199 amino acids SEQ ID No. 59) and for bovine AMH, amino acids 271 to 466 (199 amino acids SEQ ID No. 60). The C-terminal portion of the pro region of interest is thus an AMH polypeptide comprising at least the 196 amino acids of sequence SEQ ID No. 57 or of a sequence having at least 75% identity with the sequence SEQ ID No. 57. Unexpectedly, the antibodies recognizing the C-terminal portion of the pro region of AMH do not need to be used in large amount in the assay in which they are employed, unlike the prior art antibodies.

In order to prepare these antibodies recognizing the C-terminal portion of AMH, the immunogen used is an AMH polypeptide, or a polynucleotide encoding this AMH polypeptide, which must comprise at least the portion that the antibodies must recognize, namely at least the C-terminal portion of the pro region of AMH, namely at least the 196 amino acids of sequence SEQ ID No. 57 or of a sequence having at least 75% identity with the sequence SEQ ID No. 57. The immunogen also comprises at most the whole AMH of the species in question or the polynucleotide encoding the whole AMH of the species in question, namely, in the case of human AMH, the 560 amino acids of sequence SEQ ID No. 2, the other AMHs comprising at least 75% identity with the sequence SEQ ID No. 2. A particular immunogen can be chosen from the following:

an AMH polypeptide, or a polynucleotide encoding this polypeptide, devoid, relative to the whole sequence of AMH, of all the amino acids located after the C-terminal portion of the pro region of AMH, namely an AMH polypeptide, or a polynucleotide encoding said AMH polypeptide, comprising at least the 426 amino acids of sequence SEQ ID No. 7 or of a sequence having at least 75% identity with the sequence SEQ ID No. 7, and at most the 451 amino acids of sequence SEQ ID No. 5 or of a sequence having at least 75% identity with the sequence SEQ ID No. 5, preferably chosen from the AMH polypeptides of sequences SEQ ID No. 5, SEQ ID No. 6 and SEQ ID No. 7 or of sequences having at least 75% identity with these sequences, for example of sequences SEQ ID No. 17, 18, 26, 27, 36, 37 or 38. This corresponds to AMH-3, where appropriate without signal peptide and optionally without precursor portion;

an AMH polypeptide, or a polynucleotide encoding this polypeptide, which corresponds to the total AMH, with all or part of the signal peptide and optionally all or part of the precursor portion, namely which comprises at least the 535 amino acids of sequence SEQ ID No. 4 or of a sequence having at least 75% identity with the sequence SEQ ID No. 4, preferably chosen from the AMH polypeptides of sequences SEQ ID No. 2, SEQ ID No. 3 and SEQ ID No. 4 or of sequences having at least 75% identity with these sequences, for example of sequences SEQ ID No. 15, 16, 24, 25, 33, 34 or 35.

The selection of the hybridomas is also carried out using 2 screening steps, in any order, with particular polypeptides and peptides.

The first screening, called screening 1, consists in retaining only the hybridomas which produce antibodies recognizing the C-terminal portion of the pro region, as described previously. To do this, two methods are possible:

Method 1: the hybridomas secreting antibodies recognizing AMH-3, namely, for human AMH-3, amino acids 1-451 (SEQ ID No. 5), where appropriate without all or part of the signal peptide and all or part of the precursor portion, or any sequence having at least 75% identity with this sequence, are first of all selected. According to one embodiment, the AMH-3 polypeptide recognized by the antibodies is a polypeptide of sequences chosen from: SEQ ID No. 5, SEQ ID No. 6 and SEQ ID No. 7 and of sequences having at least 75% identity with these sequences. The hybridomas which produce antibodies recognizing the portion of AMH located before the C-terminal portion of the pro region of AMH, namely, for human AMH, amino acids 1-255 (SEQ ID No. 8-AMH-2), where appropriate without all or part of the signal peptide and all or part of the precursor portion, and any sequence having at least 75% identity with this sequence, are then discarded. This AMH polypeptide is referred to as AMH polypeptide (a) not recognized by the antibodies prepared according to the invention. According to one embodiment, the AMH polypeptide (a) not recognized by the antibodies is a polypeptide of sequences chosen from: SEQ ID No. 8, SEQ ID No. 9 and SEQ ID No. 10 and of sequences having at least 75% identity with these sequences.

Method 2: the hybridomas secreting antibodies recognizing the C-terminal portion of the pro region of AMH, namely, for human AMH, amino acids 256-451 (SEQ ID No. 57), or any sequence having at least 75% identity with this sequence, are selected.

The second screening, called screening 2, consists in discarding the hybridomas which produce antibodies which recognize linear epitopes (b) in the C-terminal portion of the pro region of AMH, namely in the sequence SEQ ID No. 57 or any sequence having 75% with the sequence SEQ ID No. 57.

The table below (table 4) presents various linear epitopes (b) determined in the C-terminal portion of the pro region of AMH, that are of use for preparing these antibodies, giving the SEQ IDs according to the species of mammal.

TABLE 4

|  | Human | Equine | Canine | Bovine |
| --- | --- | --- | --- | --- |
| Linear epitopes on the C-terminal portion of the pro region | SEQ ID No. 61 to 68 | SEQ ID No. 69 to 74 | SEQ ID No. 75 to 81 | SEQ ID No. 82 to 85 |
|  |  | SEQ ID No. 62 and 63 | SEQ ID No. 73 | SEQ ID No. 62, 63, 70 and 73 |

The anti-AMH antibodies thus prepared have the following characteristics: they recognize an AMH polypeptide comprising at least the 196 amino acids of sequence SEQ ID No. 57 or of a sequence having at least 75% identity with the sequence SEQ ID No. 57, they recognize neither (a) an AMH polypeptide comprising at least the 230 amino acids of sequence SEQ ID No. 10, or of a sequence having at least 75% identity with the sequence SEQ ID No. 10, and at most the 255 amino acids of sequence SEQ ID NO. 8, or of a sequence having at least 75% identity with the sequence SEQ ID No. 8, nor (b) a linear epitope located in the sequence SEQ ID No. 57 or a sequence having at least 75% identity with the sequence SEQ ID No. 57, for example the sequences SEQ ID No. 61 to 85.

All the characteristics and definitions previously described for the method for preparing antibodies of the invention and for the antibodies of the invention also apply here.

One of the two binding partners may be coupled to a label so as to form a conjugate or a tracer. The other binding partner may be captured on a solid support, this being directly or indirectly. Reference is then made to a capture partner for the latter and a detection partner for the former.

The pairs of AMH-binding partners used in the method for quantifying AMH of the invention can recognize either the pro region and the mature region of AMH, or only the pro region, in particular when use is made, with the antibodies of the invention, of an anti-AMH antibody recognizing the C-terminal portion of the pro region. Thus, according to one particular embodiment, the second AMH-binding partner used in the quantification method is an antibody recognizing an AMH polypeptide comprising at least the 196 amino acids of sequence SEQ ID No. 57 or of a sequence having at least 75% identity with the sequence SEQ ID No. 57, but recognizing neither (a) an AMH polypeptide comprising at least the 230 amino acids of sequence SEQ ID No. 10, or of a sequence having at least 75% identity with the sequence SEQ ID No. 10, and at most the 255 amino acids of sequence SEQ ID No. 8, or of a sequence having at least 75% identity with the sequence SEQ ID No. 8, nor (b) a linear epitope located in the sequence SEQ ID No. 57 or a sequence having at least 75% identity with the sequence SEQ ID No. 57, the latter possibly being in the form of a fragment and/or of a conjugate with a label capable of generating the emission of a detectable signal for the visualization of an immunological reaction between this conjugate and the AMH of a biological sample.

The bringing of the biological sample into contact with the two AMH-binding partners can be in one step or in two steps, as is widely known to those skilled in the art. Briefly, a one-step immunoassay comprises bringing the test sample simultaneously into contact with the two binding partners, including the antibodies, antibody fragments or conjugates of the invention as previously defined, whereas a two-step immunoassay comprises bringing the test sample into contact firstly with the first binding partner, and then the analyte-first binding partner complex thus formed is brought into contact with the second binding partner, one of the two binding partners being of course an antibody, antibody fragment or conjugate of the invention as previously defined.

The method can also comprise other steps known to those skilled in the art, such as washing steps and incubation steps.

The second step of the quantification method of the invention comprises or consists in detecting a signal emitted by the binding between said binding partners and the AMH, if it is present, using a label capable of generating the emission of a detectable signal as previously defined. This label can be conjugated to one of said AMH-binding partners.

Depending on the type of labeling used, those skilled in the art will add reagents which allow the visualization of the labeling, or the emission of the detectable signal, by means of any type of suitable measurement device, for instance a spectrophotometer, a spectrofluorimeter, a densitometer, a luminometer or else a high-definition camera.

The final step of the method for quantifying AMH comprises or consists in converting the detected signal into AMH concentration. Reference is also made to levels or amounts of AMH. The general principle is that the measured signal emitted during the immunoassay is proportional to the amount of AMH of the biological sample.

This step of converting the signal detected into AMH concentration is widely known to those skilled in the art. It consists in using a preestablished mathematical model on the basis of a standard range. This standard range will be obtained beforehand in a known manner. Briefly, the obtaining of the standard range consists in measuring the signal generated by increasing and known amounts or concentrations of the target analyte (AMH), in plotting the curve giving the signal as a function of the level of AMH and in finding a mathematical model which represents this relationship as faithfully as possible. The mathematical model will be used to determine the unknown amounts, titers or concentrations of AMH contained in the biological sample to be tested.

The determination of the AMH concentration can be used in several respects, and in particular in the context of fertility in women, for estimating the ovarian reserve in women, for example in women who should receive extensive treatment that would risk destroying follicles, but also in boys before puberty, for example in the event of disorders associated with sexual differentiation.

Thus, another subject of the invention relates to the use of the antibodies, antibody fragments or conjugates of the invention, whether or not they are prepared using the method of the invention, alternatively the quantification method of the invention as an aid:

for the diagnosis of disorders associated with an ovarian dysfunction in women of child-bearing age, or in evaluating the ovarian follicular reserve in young girls over the age of 12 and women, or in evaluating disorders associated with sexual differentiation in boys before puberty.

For implementing the methods of the invention, used in particular according to the uses described above, the antibodies, fragments or conjugates of the invention can be contained in kits.

Thus, another subject of the invention relates to the kits comprising an antibody or antibody fragment as previously defined or prepared and/or a conjugate as previously defined.

Here again, the characteristics and definitions previously described in the context of the antibodies and methods of the invention apply to the kits of the invention.

According to one particular embodiment, the kits also comprise or contain at least one positive control. This positive control comprises a compound capable of binding to the binding partners employed during the use of the kit, the compound being present in a predetermined amount.

By way of nonlimiting examples of such compounds, mention may be made of the total AMH of sequence SEQ ID No. 2 or of a sequence having at least 75% identity with the sequence SEQ ID No. 2, where appropriate with all or part of the signal peptide and optionally all or part of the precursor portion.

The kits can also contain all the compounds required for demonstrating the reaction between the binding partners and the AMH, such as washing buffers or reagents allowing the visualization of a labeling or the emission of a detectable signal.

The invention will be understood more clearly by means of the following examples which are given by way of nonlimiting illustration, and also by means of FIGS. 1 to 4, in which:

FIG. 1 is a diagrammatic representation of the structure of the human AMH protein and of the human AMH-1, AMH-2 and AMH-3 protein constructs which derive therefrom.

FIG. 2 is a Western blot analysis of the cell lysates obtained by transfections of the AMH-1, AMH-2, AMH-3 and whole AMH gene constructs in HEK293T cells, after separation by electrophoresis on a Bis-Tris 4-12% gel. Wells 1, 2: negative control lysate (cells transfected with an empty plasmid); wells 3, 4: AMH-1 lysate; wells 5, 12: molecular weight standard; wells 6, 7: AMH-2 lysate; wells 8, 9: AMH-3 lysate; wells 10, 11: whole AMH lysate. Wells 1, 3, 6, 8 and 10 correspond to condition A: the samples loaded were heated and reduced. Wells 2, 4, 7, 9 and 11 correspond to condition B: the samples loaded were heated but not reduced. FIG. 2A is a photograph of the membrane tested with an anti-β-actin antibody, which serves to verify that equivalent amounts of total proteins were loaded in each well. FIG. 2B is a photograph of the membrane tested with an anti-histidine antibody (Qiagen). The bands which correspond to the AMH constructed expression products have been boxed in.

FIG. 3 is a Western blot analysis of the AMH-2 and AMH-3 proteins purified from the supernatants of gene construct transfections in HEK293T cells, after separation by electrophoresis on a Bis-Tris 4-12% gel. Well 1: negative control (cells transfected with an empty plasmid); well 2: AMH-2; well 3: AMH-3; well 5: molecular weight standard. The samples loaded were heated but not reduced. Five identical membranes (FIGS. 3A to 3E) were prepared and each was tested either with an anti-AMH antibody or with an anti-histidine antibody (Qiagen).

Figure 4:
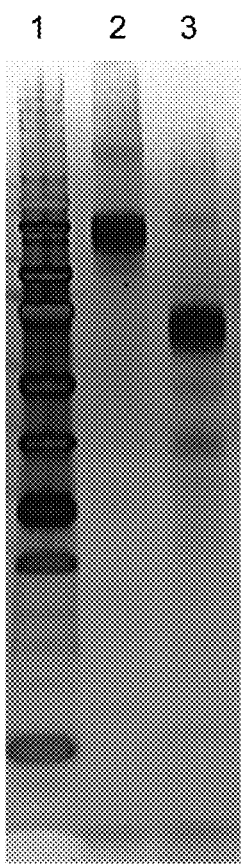

FIG. 4 is an SDS-PAGE analysis of the recombinant AMH protein CHO-AMH5 3F1 purified by affinity chromatography. The SDS-PAGE gel was stained with silver nitrate in order to visualize the total proteins. Well 1: molecular weight standard; well 2: recombinant AMH heated but not reduced; well 3: recombinant AMH heated and reduced.

EXAMPLES

Example 1: Cloning of DNA Fragments Corresponding to the Whole Sequence of Human AMH or to Truncated Sequences, and Transient Transfection in HEK 293T Cells 1.1. Gene Constructs The whole AMH sequence expressed is that of human AMH which comprises 560 amino acids (SEQ ID No. 2 corresponding to accession No. P03971 of the Uniprot KB database); this construct is called AMH-560. It comprises the signal peptide (amino acids 1-18) and a precursor portion (amino acids 19-25) which are cleaved during the post-translational maturation of the protein.

Three other protein constructs, called AMH-1, AMH-2 and AMH-3, corresponding respectively to the sequences of amino acids 1-156 (SEQ ID No. 11), 1-255 (SEQ ID No. 8) and 1-451 (SEQ ID No. 5) of AMH were prepared. A polyhistidine (8-His) tag was added on the C-terminal side for these 4 constructs in order to facilitate purification (Tag not added in the sequence listing).

The DNA fragments corresponding to the AMH-1, AMH-2, AMH-3 and whole AMH constructs, the sequences of which are given in table 5 below, were obtained in the form of synthetic genes from the company GeneArt® (Life Technologies). Each DNA fragment (AMH-1, AMH-2, AMH-3 and whole AMH) was cloned between the Eco RI and Not I sites in the pCMV6-XL5 vector under the control of the CMV promoter. The plasmids obtained were verified by sequencing at the level of the inserts in order to be sure that they did not contain errors.

TABLE 5

| Name | AMH Polynucleotide | Corresponding DNA fragment SEQ ID No. X-8HIS-stop codon |
|---|---|---|
| AMH-1 | SEQ ID No. 86 | SEQ ID NO. 86-CACCACCATCATCACCATCACCAC-TGA |
| AMH-2 | SEQ ID No. 87 | SEQ ID NO. 87-CACCACCATCATCACCATCACCAC-TGA |
| AMH-3 | SEQ ID No. 88 | SEQ ID NO. 88-CACCACCATCATCACCATCACCAC-TGA |
| Whole AMH | SEQ ID No. 89 | SEQ ID NO. 89-CACCACCATCATCACCATCACCAC-TGA |

1.2. Transient Transfection in HEK293T Cells

Culture. The HEK-293T/17 SF cells (ATCC ACS-4500™) were cultured serum-free in HEK Plus SFM medium (ATCC #8006386597) enriched with glutamine (Gibco #250030.24), according to the supplier's instructions. The cells were cultured in F75 culture flasks and maintained in an incubator at 37° C. with 5% $CO_2$ before transfection.

Transfection. The HEK293T SF cells ($10^6$ cells) were transfected by nucleofection using the Amaxa nucleofector device (Lonza), by applying the protocol supplied with the Amaxa cell line nucleofector kit V (#VCA-1003) and using 5 μg of DNA for 1 million cells per transfection. Briefly, 1 million cells are centrifuged at 200 g for 10 minutes in order to harvest them. The cell pellet is then resuspended in 100 μl of solution V (supplied in the kit). 5 μg of plasmid is added to the cell suspension. The whole mixture is gently mixed and transferred into an Amaxa cuvette (also supplied in the kit). The cuvette is inserted into the nucleofector device set to the Amaxa Q-001 program and the nucleofection is then activated. The sample is then immediately transferred to a warm medium in a 6-well cell culture plate that will be incubated at 37° C., 5% $CO_2$. The HEK293T SF cells are cultured for 48 hours.

Lysis and harvest. 48 Hours post-transfection, the supernatants are collected and then frozen at −80° C. after protease inhibitors (cOmplete™, EDTA-free protease inhibitor cocktail tablets from Roche) have been added. The transfected cell pellets ($6 \times 10^6$ cells/pellet) are taken up with 1.8 ml of 5.5 mM phosphate lysis buffer containing 130 mM NaCl, 0.5% Triton X-100, 5 U/ml benzonase nuclease (Novagen), 0.48 G/L $MgCl_2$ and protease inhibitors (cOmplete™, EDTA-free protease inhibitor cocktail tablets, Roche Cat. No. 045-6642, 1 tablet/50 ml, pH 7.4). The cell lysate is then placed in ice for 30 minutes, then centrifuged for 15 minutes at 13 000 g, 4° C. The supernatants obtained contain the AMH-1, AMH-2, AMH-3 and whole AMH proteins, and are stored at −80° C.

1.3. Western-Blot Analysis of the Protein Expression

A first characterization of the expression products obtained during step 1.2. was carried out by SDS-PAGE analysis on a NuPAGE® Bis-Tris 4-12% gel in NuPAGE® MES SDS buffer (Life Technologies). Before being loaded onto the gel (14 µl/well), the transfection supernatants and lysates were diluted in the NuPAGE® LDS 4× Sample Buffer 4× (Life Technologies) (3/1, volume/volume) and underwent various treatments. The reduction is carried out by addition of a final concentration 55 mM of dithiothreitol (DTT). The heating is for 5 min at 75° C.

Condition A: HEATED and REDUCED (with DTT)
Condition B: HEATED and NON-REDUCED (without DTT).

After the migration of the gel, the proteins separated by electrophoresis are transferred onto a 0.45 µm nitrocellulose membrane at 350 mA constant current for 50 minutes in a 1× Tris-glycine buffer containing 20% of methanol. The passivation of the membrane is carried out in the presence of 3% BSA (bovine serum albumin) in 5.5 mM phosphate buffer containing 130 mM NaCl, overnight at $+2/8°$ C. After passivation, a mouse anti-histidine monoclonal antibody (Qiagen, Cat. No. 34660) is diluted to 1/2000 in 5.5 mM phosphate buffer containing 130 mM NaCl and 0.05% of Tween 20, then 10 ml of this dilution are incubated with the membrane for 1 h at $+18/25°$ C. A second membrane, prepared in exactly the same way, is incubated at the same time and under the same conditions with a mouse anti-β-actin monoclonal antibody (clone AC-15, Life Technologies, Cat. No. AM4302) in place of the anti-histidine antibody. This membrane serves to verify that, in each well, comparable amounts of total protein have been subjected to analysis (equivalent mode control).

After rinsing of the membranes in order to remove the unbound antibodies (5 washes for 5 min in 5.5 mM phosphate buffer containing 130 mM NaCl and 0.05% Tween 20), they are incubated for 1 h with a horseradish peroxidase-conjugated anti-mouse secondary antibody (Jackson Immunoresearch, Cat. No. 115-036-003) diluted to 1/20000 in 1× PBS containing 0.2% Tween 20. After 5 washes of 5 minutes in 1× PBS containing 0.2% Tween 20, the visualization is carried out by incubating the membranes in a Clarity Western-blot Substrate solution (Biorad, Cat. No. 170-5061), for 5 minutes with stirring, before acquisition by chemiluminescence (Chemidoc XRS, Biorad).

The results are presented in FIG. 2. On the membrane visualized with the anti-β-actin antibody (FIG. 2A), a single band per well is observed and the intensities of these bands are equivalent, with the exception of the AMH-1 wells (3 and 4), which is slightly less intense. This control is therefore validated. On the membrane visualized with the anti-histidine antibody (FIG. 2B), bands show up in the negative control wells. However, said wells contain a lysate of cells transfected with a plasmid-free blank. This is the case of nonspecific reactivity of the anti-histidine antibody with certain proteins in the lysate which are in all of the wells. In addition to these nonspecific bands, the AMH-1, AMH-2, AMH-3 and whole AMH wells contain specific bands, that is to say bands not present in the negative control wells. These specific bands are boxed-in in FIG. 2B. Their apparent molecular weights, for the heated and reduced condition, are approximately 20, 30, 55 and 65 kDa, respectively, for the AMH-1, AMH-2, AMH-3 and whole AMH constructs (wells 3, 6, 8, 10). The apparent molecular weights for the heated but not reduced condition are approximately 36, 50, 100 and 120 kDa, respectively, for the AMH-1, AMH-2, AMH-3 and whole AMH constructs (wells 4, 7, 9, 11). These molecular weight estimations are compatible with a dimerization of the AMH constructs in the non-reduced condition. It is important to note that the dimerization also takes place in the absence of the mature region and despite the considerable random C-terminal truncations carried out in the AMH-1 and AMH-2 constructs.

In conclusion, this Western blot analysis shows that the AMH-1, AMH-2, AMH-3 and whole AMH plasmid constructs clearly make it possible to express proteins containing a histidine tag, the apparent molecular weights of which correspond to the expected molecular weights, by virtue of the nucleotide sequences.

Example 2: Stable Expression of the AMH Protein in CHO Cells and Purification

A stable clone of recombinant CHO (Chinese Hamster Ovary) cells expressing the whole AMH was obtained using the cGPS CHO-Sa CEMAX kit from Cellectis (Cat. No. CHOSa-0011-05 and CHOSa-0011-10) and according to the associated protocol. This kit allows the targeted intrachromosomal integration of an exogenous gene in CHO cells. It is composed of the cGPS CHO-Sa cell line (adherent cells), an integration vector into which the gene of interest is cloned, a vector constitutively expressing meganuclease I-Sce I and the TransMessenger™ Transfection Reagent kit (Qiagen Cat. No. 301525). The genetically modified cGPS CHO-Sa cell line has the particularity of containing, in its genome, a large and unique particular site recognized by meganuclease I-Sce I which has an endonuclease activity.

2.1. Cloning

A synthetic gene encoding the whole human AMH protein (aa 1-560) linked to a C-terminal 8-histidine tag was ordered from the company Geneart. The gene was optimized for expression in the CHO host. This AMH gene was cloned into the pIM.LP2.Zeo integration vector sold by Cellectis, between the Eco RI and Not I sites under the control of the CMV promoter. The pIM.LP2.Zeo integration vector has the particularity of containing 2 regions which are homologous, respectively, to the region upstream and downstream of the unique site recognized by meganuclease I-Sce I in the CHO genome. These 2 particular regions frame the multiple cloning site into which the gene encoding the AMH was inserted. Furthermore, this integration plasmid provides the transfected CHO cells with 2 selective advantages. The first is the zeocin-resistance gene, controlled by the CMV promoter. The second is the neomycin resistance gene controlled by the SV40 promoter. This gene also enables resistance to geneticin (G418), an antibiotic close to neomycin.

2.2. Transfection

One day before transfection (D-1), $2\times10^5$ cGPS CHO-Sa CEMAX adherent cells are seeded, per 10 cm Petri dish, in an F-12K medium supplemented with 2 mM L-glutamine, penicillin (100 UI/ml), streptomycin (100 µg/ml), amphotericin B (Fongizone) (0.25 µg/ml) and 10% of fetal calf serum.

On the day of transfection (D), 1 µg of the integration vector (pIM.LP2.Zeo) containing the AMH gene and 1 µg of meganuclease mRNA are diluted in EC-R buffer (available in the TransMessenger™ Transfection reagent kit). 4 µl of the Enhancer reagent are then added [nucleic acid (mg)/Enhancer (ml) ratio=½]. The total reaction volume must be 100 µl. The solution is then incubated for 5 minutes at ambient temperature. 16 µl of the TransMessenger™ reagent are subsequently added and then the whole mixture is incubated for 10 minutes at $+^{18}/_{25}°$ C., before being deposited onto the $2\times10^5$ cells, the culture medium of which has been replaced beforehand with 900 µl of serum-free and antibiotic-free F-12k medium.

2.3 Clonal Selection and Characterization of Clones

The AMH recombinant clones were selected according to their resistances to zeocin and to geneticin (G418).

24 h after transfection (D+1), the culture medium is replaced with 10 ml of complete medium supplemented with 0.6 mg/ml of G418, then, starting from the $6^{th}$ day (D+6), the culture medium is regularly replaced with fresh medium supplemented with 0.6 mg/ml of G418 and 0.4 mg/ml of zeocin. 15 days after transfection (D+15), the cells are isolated by limiting dilution in a 96-well plate. After this cell cloning, the clones were amplified by culture and then tested:
- by PCR on the genomic DNA extracted from the CHO cells, using primers specific for the 5' and 3' ends of the AMH gene,
- by Western blotting in order to verify the expression of the AMH protein.

Among the clones that were positive both in PCR and in Western blotting, the AMH5 3F1 clone was selected. For this clone, the PCR product obtained by amplification of the AMH gene was sequenced in its entirety in order to verify the integrity of the gene and to be sure that no mutation had been introduced during the selection.

2.4. Expression of the Recombinant AMH Using the Stable CHO-AMH5 3F1 Clone The AMH5 3F1 clone is cultured in a 225 cm² culture dish in a proportion of $9\times10^6$ cells in 60 ml of Excell 302 culture medium (Sigma Cat. No. 4324C) supplemented with 1% v/v antibiotics and antifungals (Gibco Cat. No. 15240), 12 mM L-glutamine (Gibco Cat. No. 25030), 6 g/l glucose (Sigma Cat. No. G8769), 0.4 mM iron citrate (Sigma Cat. No. F6129), 2% hypoxanthine-thymidine (Gibco Cat. No. 41065), 1% glycerol and 1 mg/l pepstatin A (Sigma Cat. No. P4265). The culture dishes are incubated in an incubator at 37° C. under an atmosphere of 7.5% $CO_2$. After 4 days of culture (amplification), the cell suspension obtained (approximately $66\times10^6$ cells) is re-seeded into 7 F225 culture dishes according to the same protocol. The supernatants of these cultures are harvested, then centrifuged at 5000 g and frozen at -25° C. until purification.

2.5. Purification of the Recombinant AMH Protein CHO-AMH5 3F1

The culture supernatants previously harvested are thawed and pooled. A 5-liter volume of supernatant is then filtered on a 0.8 µm membrane (Nalgene, VWR Cat. No. 7345084) and then a 0.22 µm membrane (Nalgene aPES Rapid Flow). The sample is then concentrated 20-fold on hollow fiber having a cut-off threshold of 30 kDa (GE Cat. No. 564110-18). The retentate of approximately 100 ml is then diafiltered against 5 times its volume with a 50 mM potassium sodium phosphate buffer, pH7.8, containing 100 mM NaCl, 1 mM EDTA, 0.9 g/l azide. Two Complete EDTA free protease inhibitor tablets (Roche Cat. No. 11 873 580 001) are added. This retentate is purified by affinity chromatography on a Hi-trap NHS Sepharose column coupled to an anti-AMH (polyclonal or monoclonal) antibody in a proportion of 10 mg of antibody per ml of gel according to the supplier's protocol (GE Cat. No. 17-0716-01). The affinity column is equilibrated in diafiltration buffer, then 50 ml of retentate are injected onto the column at a speed of 0.5 ml/min. Washing is then carried out in 50 mM Tris HCl buffer pH 7.9, containing 100 mM NaCl, 1 mM EDTA. The elution of the AMH protein is then carried out with a 0.1 M glycine-HCl buffer, pH 2.9, at a speed of 0.5 ml/min. The elution fractions collected are immediately neutralized to pH 7-8, protease inhibitors are added thereto, and the fractions are pooled and stored at -80° C. in a 0.2 M $NaHCO_3$ storage buffer containing 0.5 M NaCl, pH 7.5, and 20% ethanol. FIG. 4 gives the photograph of the membrane following SDS-PAGE analysis of the recombinant AMH protein CHO-AMH5 3F1 according to the protocol of example 1.3. In place of the Western blot, the total proteins were stained with silver nitrate. The purified protein is very pure.

Example 3: Preparation of Anti-AMH Antibodies of the Invention by Immunization of Mice 3.1. Immunogens The whole AMH and AMH-3 plasmids obtained in example 1 were amplified by culture in *E. coli* bacteria, then purified using the EndoFree Plasmid Mega Kit from Qiagen (Cat. No. 12381) or equivalent kit. For the preparation of the Gene Gun cartridges (Bio-Rad), 2 µg of plasmid DNA were precipitated on 0.22 mg of gold beads 1 µm in diameter in the presence of $CaCl_2$ and of spermidine, according to the supplier's instructions. The beads thus prepared can be stored at $+^{2}/_{8}°$ C. in the dark, in the presence of a moisture absorber (desiccant sachet).

The recombinant AMH protein CHO-AMH5 3F1 obtained in example 2 was mixed volume for volume with Freund's adjuvant (Sigma), prepared in the form of a water-in-oil emulsion and which is known to have a good adjuvant capacity. This preparation was carried out extemporaneously before each injection.

3.2. Immunizations

The immunization experiments were carried out in female BALB/c ($H-2^d$) mice from six to eight weeks old at the time of the first immunization. Various protocols are carried out:
- 4 doses of 4 µg per injection of whole AMH DNA at 0, 2, 4 and 6 weeks,
- 4 doses of 4 µg per injection of AMH-2 DNA at 0, 2, 4 and 6 weeks,
- 4 doses of 4 µg per injection of AMH-3 DNA at 0, 2, 4 and 6 weeks,
- 3 doses of 10 µg per injection of AMH protein at 0, 2, and 4 weeks.

For the DNA immunizations, the mice were shaved on their abdomen. The Helios Gene Gun Delivery System (Bio-Rad) was used at a pressure of 2750 kPa to inject the DNA-coated gold beads into the skin of the mice. For the protein immunizations, the injection was carried out subcutaneously.

In order to monitor the appearance of the antibodies, blood samples are regularly taken from the mice. The presence of the anti-AMH antibodies in these sera is tested by carrying out an ELISA on a 96-well microplate. The recombinant AMH protein CHO-AMH5 3F1 is used in capture mode (1 µg/well); after saturation, this antigen is reacted with various dilutions of sera to be tested (incubation at 37° C., for 1 h). The anti-AMH antibodies present in the serum are revealed using an AffiniPure goat anti-mouse IgG antibody conjugated to alkaline phosphate (H+L, Jacskon Immunoresearch, Cat No. 115-055-146), which binds to the antibodies sought (0.1 µg/well). The mice which had developed anti-AMH antibodies are thus identified among the immunized mice.

Between 50 and 70 days after the first injections, the mice that had developed an anti-AMH humoral response were restimulated by means of an intravenous injection of 100 µg of AMH protein.

3.3. Preparation of the Hybridomas

Three days after this final injection, the responding mice were sacrificed: the blood and spline were removed. The splenocytes obtained from the spline were cultured with Sp2/0-Ag14 myeloma cells in order for them to fuse and to become immortalized, according to the protocol described by Kohler and Milstein (Kohler and Milstein 1975, Kohler et al., 1976). After a culture period of 12-14 days, the hybridoma supernatents obtained were screened to determine the presence of anti-AMH antibodies using the ELISA assay described in the preceding section.

3.4. Selection of the Supernatants of Hybridomas Recognizing the 157-255 Region or the 256-451 Region of the Human AMH Protein A rabbit anti-6 histidine antibody (Sigma Aldrich, Cat. No. SAB4301134 or equivalent) was diluted in 1× PBS and adsorbed onto a 96-well microtitration plate in a proportion of 1 µg/well, by incubation overnight at $+^{18}/_{25}°$ C. The plate is then washed 3 times in PBS-0.05% Tween 20 buffer (PBS-T), then passivated by incubation in a PBS-T buffer containing 10 g/l of BSA and again washed 3 times in PBS-T buffer.

The lysates obtained in example 1 and stored at −80° C. are thawed and diluted between ½ and ¹/₁₀ in 1× PBS buffer. 100 µl of each of the lysates (negative control, AMH-1, AMH-2, AMH-3 and whole AMH) are dispensed into several wells of the plate and incubated for 2 h at 37° C. The plate is then emptied and washed 4 times in PBS-T buffer containing 300 mM of NaCl. The hybridoma supernatants to be tested (100 µl) are then added to each of the 5 different lysates and incubated for 1 h at 37° C.

After a further step of 4 washes in PBS-T containing 300 mM NaCl, the secondary antibody, which is an AffiniPure anti-mouse IgG produced in goats, conjugated to peroxidase (H+L, Jacskon Immunoresearch, Cat No. 115-035-166), is added. After a further step of 3 washes in PBS-T containing 300 mM NaCl, the reaction is visualized by incubating the plate for 10 min at $+^{18}/_{25}°$ C. in the presence of the Sure-Blue™ TMB Microwell Peroxidase substrate (KLP, Cat. No. 52-00-01). The plate is read by measuring the OD at 450 and 630 nm.

Selection of the supernatants of hybridomas recognizing the 157-255 region. The hybridomas selected from the results of the ELISA are those of which the supernatants contain antibodies which recognize the AMH-2 lysate and do not recognize the AMH-1 lysate. Of course, the AMH-3 and whole AMH lysates are also recognized by the supernatants of the hybridomas chosen. The 5G5 1B11 hybridomas were thus selected.

Selection of the supernatants of hybridomas recognizing the 256-451 region. The hybridomas selected from the results of the ELISA are those of which the supernatants contain antibodies which recognize the AMH-3 lysate and do not recognize the AMH-2 lysate, or the AMH-1 lysate. Of course, the whole AMH lysate is also recognized by the supernatants of the hybridomas chosen. The 3H8, 4C7 and 4G10 hybridomas were thus selected.

After the selection, the hybridomas chosen were cloned according to the limiting dilution technique, well known to those skilled in the art, in order to be sure of the clonality. It was thus possible to obtain monoclonal hybridomas secreting the following anti-AMH antibodies:

5G5A10 and 1B11B1 which recognize the 157-255 region of human AMH,

3H8E2, 4C7E12 and 4G10E12 which recognize the 256-451 region of human AMH.

The large-scale production of the monoclonal antibodies was carried out by culturing the hybridomas in the miniPERM™ bioreactor, according to a protocol derived from the publication by Falkenberg (1998). The monoclonal antibodies were then purified from the culture supernatant by affinity chromatography on protein A.

Example 4: Selection of the Anti-AMH Monoclonal Antibodies Recognizing the Non-Linear Epitopes Among the monoclonal antibodies obtained in example 3, those which were directed against linear epitopes were determined in order to select those recognizing non-linear epitopes. To do this, 80 synthetic peptides covering the whole of the amino acid sequence of human AMH were synthesized. The binding of the antibodies to each of these peptides were tested by ELISA.

4.1. Peptide Synthesis

80 Peptides of 16 amino acids were synthesized. Among the 16 amino acids, 12 correspond to the AMH sequence and overlap by 5 amino acids, thus covering the whole of the human AMH sequence (amino acids 1-560). A biotin and then an SGSG sequence (spacer arm) were added at the N-terminal end in order to facilitate the analysis of these peptides by ELISA. These peptides are non-purified and in solution (water/acetonitrile). They were verified by LC/MS mass spectrometry. The sequences synthesized are presented in table 6.

TABLE 6

Sequences of the human AMH peptides

| Peptide No. | AMH peptide (SEQ ID No.) | Positions | Total sequence |
|---|---|---|---|
| 1 | MRDLPLTSLALV (SEQ ID No. 90) | 1-12 | Bio-SGSG-MRDLPLTSLALV-amide |

TABLE 6-continued

Sequences of the human AMH peptides

| Peptide No. | AMH peptide (SEQ ID No.) | Positions | Total sequence |
|---|---|---|---|
| 2 | SLALVLSALGAL (SEQ ID No. 91) | 8-19 | Bio-SGSG-SLALVLSALGAL-amide |
| 3 | ALGALLGTEALR (SEQ ID No. 92) | 15-26 | Bio-SGSG-ALGALLGTEALR-amide |
| 4 | TEALRAEEPAVG (SEQ ID No. 93) | 22-33 | Bio-SGSG-TEALRAEEPAVG-amide |
| 5 | EPAVGTSGLIFR (SEQ ID No. 94) | 29-40 | Bio-SGSG-EPAVGTSGLIFR-amide |
| 6 | GLIFREDLDWPP (SEQ ID No. 95) | 36-47 | Bio-SGSG-GLIFREDLDWPP-amide |
| 7 | LDWPPGSPQEPL (SEQ ID No. 96) | 43-54 | Bio-SGSG-LDWPPGSPQEPL-amide |
| 8 | PQEPLCLVALGG (SEQ ID No. 97) | 50-61 | Bio-SGSG-PQEPLCLVALGG-amide |
| 9 | VALGGDSNGSSS (SEQ ID No. 98) | 57-68 | Bio-SGSG-VALGGDSNGSSS-amide |
| 10 | NGSSSPLRVVGA (SEQ ID No. 99) | 64-75 | Bio-SGSG-NGSSSPLRVVGA-amide |
| 11 | RVVGALSAYEQA (SEQ ID No. 100) | 71-82 | Bio-SGSG-RVVGALSAYEQA-amide |
| 12 | AYEQAFLGAVQR (SEQ ID No. 101) | 78-89 | Bio-SGSG-AYEQAFLGAVQR-amide |
| 13 | GAVQRARWGPRD (SEQ ID No. 102) | 85-96 | Bio-SGSG-GAVQRARWGPRD-amide |
| 14 | WGPRDLATFGVC (SEQ ID No. 103) | 92-103 | Bio-SGSG-WGPRDLATFGVC-amide |
| 15 | TFGVCNTGDRQA (SEQ ID No. 104) | 99-110 | Bio-SGSG-TFGVCNTGDRQA-amide |
| 16 | GDRQAALPSLRR (SEQ ID No. 105) | 106-117 | Bio-SGSG-GDRQAALPSLRR-amide |
| 17 | PSLRRLGAWLRD (SEQ ID No. 106) | 113-124 | Bio-SGSG-PSLRRLGAWLRD-amide |
| 18 | AWLRDPGGQRLV (SEQ ID No. 107) | 120-131 | Bio-SGSG-AWLRDPGGQRLV-amide |
| 19 | GQRLVVLHLEEV (SEQ ID No. 108) | 127-138 | Bio-SGSG-GQRLVVLHLEEV-amide |
| 20 | HLEEVTWEPTPS (SEQ ID No. 109) | 134-145 | Bio-SGSG-HLEEVTWEPTPS-amide |
| 21 | EPTPSLRFQEPP (SEQ ID No. 110) | 141-152 | Bio-SGSG-EPTPSLRFQEPP-amide |
| 22 | FQEPPPGGAGPP (SEQ ID No. 111) | 148-159 | Bio-SGSG-FQEPPPGGAGPP-amide |
| 23 | GAGPPELALLVL (SEQ ID No. 112) | 155-166 | Bio-SGSG-GAGPPELALLVL-amide |
| 24 | ALLVLYPGPGPE (SEQ ID No. 113) | 162-173 | Bio-SGSG-ALLVLYPGPGPE-amide |
| 25 | GPGPEVTVTRAG (SEQ ID No. 114) | 169-180 | Bio-SGSG-GPGPEVTVTRAG-amide |
| 26 | VTRAGLPGAQSL (SEQ ID No. 115) | 176-187 | Bio-SGSG-VTRAGLPGAQSL-amide |

TABLE 6-continued

Sequences of the human AMH peptides

| Peptide No. | AMH peptide (SEQ ID No.) | Positions | Total sequence |
|---|---|---|---|
| 27 | GAQSLCPSRDTR (SEQ ID No. 116) | 183-194 | Bio-SGSG-GAQSLCPSRDTR-amide |
| 28 | SRDTRYLVLAVD (SEQ ID No. 117) | 190-201 | Bio-SGSG-SRDTRYLVLAVD-amide |
| 29 | VLAVDRPAGAWR (SEQ ID No. 45) | 197-208 | Bio-SGSG-VLAVDRPAGAWR-amide |
| 30 | AGAWRGSGLALT (SEQ ID No. 118) | 204-215 | Bio-SGSG-AGAWRGSGLALT-amide |
| 31 | GLALTLQPRGED (SEQ ID No. 119) | 211-222 | Bio-SGSG-GLALTLQPRGED-amide |
| 32 | PRGEDSRLSTAR (SEQ ID No. 46) | 218-229 | Bio-SGSG-PRGEDSRLSTAR-amide |
| 33 | LSTARLQALLFG (SEQ ID No. 120) | 225-236 | Bio-SGSG-LSTARLQALLFG-amide |
| 34 | ALLFGDDHRCFT (SEQ ID No. 121) | 232-243 | Bio-SGSG-ALLFGDDHRCFT-amide |
| 35 | HRCFTRMTPALL (SEQ ID No. 47) | 239-250 | Bio-SGSG-HRCFTRMTPALL-amide |
| 36 | TPALLLLPRSEP (SEQ ID No. 122) | 246-257 | Bio-SGSG-TPALLLLPRSEP-amide |
| 37 | PRSEPAPLPAHG (SEQ ID No. 123) | 253-264 | Bio-SGSG-PRSEPAPLPAHG-amide |
| 38 | LPAHGQLDTVPF (SEQ ID No. 61) | 260-271 | Bio-SGSG-LPAHGQLDTVPF-amide |
| 39 | DTVPFPPPRPSA (SEQ ID No. 124) | 267-278 | Bio-SGSG-DTVPFPPPRPSA-amide |
| 40 | PRPSAELEESPP (SEQ ID No. 125) | 274-285 | Bio-SGSG-PRPSAELEESPP-amide |
| 41 | EESPPSADPFLE (SEQ ID No. 126) | 281-292 | Bio-SGSG-EESPPSADPFLE-amide |
| 42 | DPFLETLTRLVR (SEQ ID No. 127) | 288-299 | Bio-SGSG-DPFLETLTRLVR-amide |
| 43 | TRLVRALRVPPA (SEQ ID No. 128) | 295-306 | Bio-SGSG-TRLVRALRVPPA-amide |
| 44 | RVPPARASAPRL (SEQ ID No. 129) | 302-313 | Bio-SGSG-RVPPARASAPRL-amide |
| 45 | SAPRLALDPDAL (SEQ ID No. 130) | 309-320 | Bio-SGSG-SAPRLALDPDAL-amide |
| 46 | DPDALAGFPQGL (SEQ ID No. 131) | 316-327 | Bio-SGSG-DPDALAGFPQGL-amide |
| 47 | FPQGLVNLSDPA (SEQ ID No. 132) | 323-334 | Bio-SGSG-FPQGLVNLSDPA-amide |
| 48 | LSDPAALERLLD (SEQ ID No. 62) | 330-341 | Bio-SGSG-LSDPAALERLLD-amide |
| 49 | ERLLDGEEPLLL (SEQ ID No. 63) | 337-348 | Bio-SGSG-ERLLDGEEPLLL-amide |
| 50 | EPLLLLLRPTAA (SEQ ID No. 64) | 344-355 | Bio-SGSG-EPLLLLLRPTAA-amide |
| 51 | RPTAATTGDPAP (SEQ ID No. 133) | 351-362 | Bio-SGSG-RPTAATTGDPAP-amide |

TABLE 6-continued

Sequences of the human AMH peptides

| Peptide No. | AMH peptide (SEQ ID No.) | Positions | Total sequence |
|---|---|---|---|
| 52 | GDPAPLHDPTSA (SEQ ID No. 65) | 358-369 | Bio-SGSG-GDPAPLHDPTSA-amide |
| 53 | DPTSAPWATALA (SEQ ID No. 66) | 365-376 | Bio-SGSG-DPTSAPWATALA-amide |
| 54 | ATALARRVAAEL (SEQ ID No. 134) | 372-383 | Bio-SGSG-ATALARRVAAEL-amide |
| 55 | VAAELQAAAAEL (SEQ ID No. 135) | 379-390 | Bio-SGSG-VAAELQAAAAEL-amide |
| 56 | AAAELRSLPGLP (SEQ ID No. 136) | 386-397 | Bio-SGSG-AAAELRSLPGLP-amide |
| 57 | LPGLPPATAPLL (SEQ ID No. 137) | 393-404 | Bio-SGSG-LPGLPPATAPLL-amide |
| 58 | TAPLLARLLALC (SEQ ID No. 138) | 400-411 | Bio-SGSG-TAPLLARLLALC-amide |
| 59 | LLALCPGGPGGL (SEQ ID No. 139) | 407-418 | Bio-SGSG-LLALCPGGPGGL-amide |
| 60 | GPGGLGDPLRAL (SEQ ID No. 140) | 414-425 | Bio-SGSG-GPGGLGDPLRAL-amide |
| 61 | PLRALLLLKALQ (SEQ ID No. 141) | 421-432 | Bio-SGSG-PLRALLLLKALQ-amide |
| 62 | LKALQGLRVEWR (SEQ ID No. 67) | 428-439 | Bio-SGSG-LKALQGLRVEWR-amide |
| 63 | RVEWRGRDPRGP (SEQ ID No. 68) | 435-446 | Bio-SGSG-RVEWRGRDPRGP-amide |
| 64 | DPRGPGRAQRSA (SEQ ID No. 142) | 442-453 | Bio-SGSG-DPRGPGRAQRSA-amide |
| 65 | AQRSAGATAADG (SEQ ID No. 143) | 449-460 | Bio-SGSG-AQRSAGATAADG-amide |
| 66 | TAADGPCALREL (SEQ ID No. 144) | 456-467 | Bio-SGSG-TAADGPCALREL-amide |
| 67 | ALRELSVDLRAE (SEQ ID No. 145) | 463-474 | Bio-SGSG-ALRELSVDLRAE-amide |
| 68 | DLRAERSVLIPE (SEQ ID No. 146) | 470-481 | Bio-SGSG-DLRAERSVLIPE-amide |
| 69 | VLIPETYQANNC (SEQ ID No. 147) | 477-488 | Bio-SGSG-VLIPETYQANNC-amide |
| 70 | QANNCQGVCGWP (SEQ ID No. 148) | 484-495 | Bio-SGSG-QANNCQGVCGWP-amide |
| 71 | VCGWPQSDRNPR (SEQ ID No. 149) | 491-502 | Bio-SGSG-VCGWPQSDRNPR-amide |
| 72 | DRNPRYGNHVVL (SEQ ID No. 150) | 498-509 | Bio-SGSG-DRNPRYGNHVVL-amide |
| 73 | NHVVLLLKMQVR (SEQ ID No. 151) | 505-516 | Bio-SGSG-NHVVLLLKMQVR-amide |
| 74 | KMQVRGAALARP (SEQ ID No. 152) | 512-523 | Bio-SGSG-KMQVRGAALARP-amide |
| 75 | ALARPPCCVPTA (SEQ ID No. 153) | 519-530 | Bio-SGSG-ALARPPCCVPTA-amide |
| 76 | CVPTAYAGKLLI (SEQ ID No. 154) | 526-537 | Bio-SGSG-CVPTAYAGKLLI-amide |

TABLE 6-continued

Sequences of the human AMH peptides

| Peptide No. | AMH peptide (SEQ ID No.) | Positions | Total sequence |
|---|---|---|---|
| 77 | GKLLISLSEERI (SEQ ID No. 155) | 533-544 | Bio-SGSG-GKLLISLSEERI-amide |
| 78 | SEERISAHHVPN (SEQ ID No. 156) | 540-551 | Bio-SGSG-SEERISAHHVPN-amide |
| 79 | HHVPNMVATECG (SEQ ID No. 157) | 547-558 | Bio-SGSG-HHVPNMVATECG-amide |
| 80 | VPNMVATECGCR (SEQ ID No. 158) | 549-560 | Bio-SGSG-VPNMVATECGCR-amide |

4.2. ELISA

The 96-well microplates are coated with streptavidin (10 µg/ml, 1 µg/well) in a 1× PBS buffer for 1 h at 37° C., and then passivated in a PBS-0.05% Tween 20 buffer (PBS-T) containing 10 g/l of BSA overnight at ambient temperature. The passivation solution is removed, then the biotinylated peptides are dispensed (10 µg/ml in 1× PBS buffer, 1 µg per well) and incubated for 1 h at 37° C. After 4 washes in PBS-T, the monoclonal antibody to be tested is added at a concentration of 1 µg/ml. After incubation for 1 h 30 at 37° C. and 4 PBS-T washes, a peroxidase-conjugated anti-mouse IgG antibody is added. The visualization is carried out with the TMB substrate with measurement of the optical density (OD) at 450 nm.

In order to validate the ELISA format, a commercial anti-AMH antibody was used as positive control. It is the AA011 clone from the company AnshLabs. This antibody specifically recognizes peptide 52 (SEQ ID No. 137), the OD signal obtained is greater than 1. Among the 5 monoclonal antibodies obtained in example 3, the 4C7E12 clone also recognizes peptide 52. The 4C7E12 clone therefore recognizes the same epitope as the AA011 clone. It is not retained. The monoclonal antibodies 5G5A10, 1B11B1, 3H8E2 and 4G10E12 recognize none of the 80 AMH peptides tested. Their epitopes are not therefore linear. It is these four non-linear antibodies 5G5A10, 1B11B1, 3H8E2 and 4G10E12 which were selected for developing a method for quantifying the AMH protein in the biological samples.

Example 5: Characterization of the Anti-AMH Antibodies 5G5A10, 1B11B1, 3118E2 and 4G10E12

5.1. Comparison of the Capture Capacity of the Anti-AMH Antibodies 5G5A10, 1B11B1, 3H8E2 and 4G10E12 by ELISA The capture antibodies (5G5A10, 1B11B1, 3H8E2 and 4G10E12) diluted to 5 µg/ml in 200 mM Tris, pH 6.2, are dispensed into a 96-well microtitration plate in a proportion of 0.5 µg/well and incubated for 1 h 30 at 37° C. The plate is then washed 3 times in a PBS-0.05% Tween 20 buffer (PBS-T), then passivated for 2 h by incubation in a PBS-T buffer containing 10 g/l of BSA and again washed 3 times in PBS-T buffer.

The lysates obtained in example 1 and stored at −80° C. are thawed, and diluted to 1/20 in 1× PBS. 100 µl of each of the lysates (negative control, AMH-1, AMH-2, AMH-3 and whole AMH) are dispensed and incubated overnight at 37° C. The plate is then emptied and washed 4 times in PBS-T buffer containing 300 mM of NaCl. A biotinylated anti-histidine antibody (Qiagen Cat. No. 34440) diluted to 1/1000 in passivation buffer is dispensed and then incubated for 1 h 30 at 37° C. The plate is again washed 3 times, before incubation with the streptavidin-peroxidase conjugate (Jackson Immunoresearch Cat. No. 016-030-034) diluted to 1/2000 in passivation buffer, for 1 h 30 at 37° C. After a further step of 3 washes in PBS-T, the reaction is visualized by incubating the plate for 10 min at +18/25° C. in the presence of the SureBlue™ TMB Microwell Peroxidase substrate (KLP, Cat. No. 52-00-01). The plate is read by measuring the OD at 450 and 630 nm.

The results obtained are presented in table 7. The OD values measured for the negative controls that are PBS and lysate transfected without plasmid are at most 0.28, which corresponds to the nonspecific signal.

TABLE 7

Capture capacity of the anti-AMH antibodies ($OD_{450\ nm}$ value)

| | Ab 1B11B1 | | Ab 5G5A10 | | Ab 3H8E2 | | Ab 4G10E12 | |
|---|---|---|---|---|---|---|---|---|
| PBS neg control | 0.129 | 0.141 | 0.196 | 0.246 | 0.137 | 0.132 | 0.178 | 0.122 |
| Lysate neg control | 0.199 | 0.189 | 0.21 | 0.223 | 0.165 | 0.159 | 0.168 | 0.281 |
| AMH-1 lysate | 0.221 | 0.236 | 0.257 | 0.266 | 0.244 | 0.198 | 0.218 | 0.203 |
| AMH-2 lysate | 4.244 | 4.246 | 4.316 | 4.191 | 0.176 | 0.197 | 0.184 | 0.168 |
| AMH-3 lysate | 3.683 | 3.774 | 3.186 | 3.365 | 1.859 | 1.815 | 1.801 | 1.622 |
| Whole AMH lysate | 3.184 | 3.351 | 3.296 | 3.36 | 1.667 | 1.711 | 2.132 | 1.812 |

The results in table 7 show that the 1B11B1 and 5G5A10 antibodies capture the AMH-2, AMH-3 and whole AMH lysates (OD >3). The 3H8E2 and 4G10E12 antibodies capture the AMH-3 and whole AMH lysates (OD >1.6). The AMH-1 lysate (amino acids 1-156) is not captured by any of the monoclonal antibodies tested.

Furthermore, the 1B11B1 and 5G5A10 antibodies which recognize the 157-255 region of the human AMH protein have capture capacities greater than those of the 3H8E2 and 4G10E12 antibodies which recognize the 256-451 region. Indeed, in the case of recognition (underlined values in table 2), for a given lysate, the OD values obtained with the 1B11B1 and 5G5A10 antibodies are higher than those obtained by the 3H8E2 and 4G10E12 antibodies. It will therefore be judicious to preferentially use, in capture mode, the 1B11B1 antibody or the 5G5A10 antibody.

5.2. Western-Blot Characterization

In order to better characterize the reactivities of the anti-AMH monoclonal antibodies, Western-blot analyses were carried out.

Protein purification. Transfections were carried out according to the protocol of example 1 with the plasmids encoding the AMH-2 and AMH-3 constructs, and also a negative control (without plasmid). The culture supernatants are recovered and the AMH proteins which are found therein are purified by batchwise metal-chelate affinity chromatography, by virtue of their polyhistidine tags. To do this, the transfection supernatants are incubated overnight at +2/8° C. with stirring with an Ni-NTA resin (Roche, Cat. No. 115-26-70) equilibrated in 11 mM phosphate buffer containing 260 mM NaCl, pH 7.4. The resin is then recovered by centrifugation for 3 min at 3000 g and the supernatant containing the non-absorbed material is removed. After 3 washes with the equilibration buffer, the protein is eluted with a 5.5 mM phosphate buffer containing 130 mM NaCl, pH 7.4, and containing 500 mM of imidazole, and protease inhibitors, and the pH of which is adjusted to 7.6. Elution is carried out by incubation at +2/8° C. with stirring, overnight. The supernatant containing the AMH is then harvested after centrifugation of the resin for 3 minutes at 3000 g. This purification step is necessary in order to concentrate the AMH proteins and especially to remove the large amounts of BSA present in the supernatants, which disrupt the migration of the SDS-PAGE gels.

Western blot. This analysis was carried out according to the protocol described in example 1, section 1.3, either using the anti-histidine antibody, or replacing it with an anti-AMH antibody (1 µg per membrane).

Results. The results of this analysis are presented in FIG. 3. The samples were analyzed after heating but without reduction. The two purified proteins AMH-2 and AMH-3 are revealed on the membrane visualized by means of the anti-histidine antibody (FIG. 3A), and no reactivity is observed in the negative control well, as expected. Among the anti-AMH antibodies tested, all of them recognize the AMH-3 protein, but it is only the 1B11B1 clone which also recognizes the AMH-2 protein, with a much lower reactivity than for AMH-3. For the 4G10E12 and 3H8E2 clones, this result is in agreement with the results obtained by ELISA. Indeed, the binding zone of these antibodies is in the 256-451 region of AMH which is not present in the AMH-2 construct. By ELISA, the 1B11B1 and 5C5A10 clones exhibit similar reactivities and recognize AMH-2 and AMH-3 well. By Western blot, the 1B11B10 antibody gives a strong signal with AMH-3, the signal obtained with AMH-2 is much weaker, although the protein is present at comparable amounts, as can be seen on the membrane visualized with the anti-His antibody. It can be concluded from this that Western blotting, which is a partially denaturing technique, is not suitable for studying the antigenicity of the AMH-2 protein. The 5G5A10 antibody which gives a very good reactivity by ELISA, gives little or no signal by Western blotting. Given its weak binding to AMH-3 under the conditions of the experiment, it is normal not to observe any reactivity with AMH-2. Overall, this experiment shows that Western blotting is not suitable for studying the recognition of non-linear antibodies which are sensitive to heat-denaturation, such as 5G5A10 or, to a certain extent, 1B11B1. The analyses carried out by Western blotting on the anti-AMH antibodies in the literature should therefore be interpreted with great care, and analyses by ELISA rather than by Western blotting should if possible be favored.

Example 6: Detection of AMH by Sandwich Immunoassay

On commercial AMH kits, a significant difference was observed between the concentrations obtained for a sample as a function of the time at which the assay was carried out after the sample had been taken. This type of variability is unacceptable in clinical practice, it is therefore essential to have available a robust kit, for which the AMH concentration measured is accurate and reproducible and which allows the samples to be stored at +2/8° C. or at −19/−31° C. before assaying. Such an assay was carried out by choosing an antibody directed against amino acids 157-255 of human AMH.

6.1. Automated Immunoassay Procedure

The detection of the AMH in the biological samples was carried out by one-step sandwich immunoassay using the VIDAS® automated immunoanalysis device (bioMérieux). The single-use tip acts both as solid phase for the reaction and its pipetting system. The cartridge of the automated device is composed of 10 wells (X0 to X9) covered with a sealed and labeled aluminum foil. The first well (X0) comprises a portion that is precut in order to facilitate the introduction of the sample. The last well (X9) is an optical cuvette in which the fluorescence of the substrate is measured. The various reagents required for the analysis are contained in the intermediate wells. All the steps of the assay are thus carried out automatically by the instrument. They consist of a succession of cycles of suction/discharge of the reaction medium.

Sensitization and passivation of the tips. The tips were sensitized with 270 µl of a solution of 5G5A10 monoclonal antibody for the pair C1 or of 8C5B10H5 monoclonal antibody for the pair C2, each at 7 µg/ml in a Tris buffer, pH 6.2. After approximately 20 h of incubation at +18/25° C. with the sensitizing solution, the tips were emptied. 300 µl of this same solution containing 5 g/l of bovine albumin are then added for the passivation of the tips at +18/25° C. for approximately 20 h. The tips are then emptied, dried, then stored at +4° C. until use, away from moisture.

Preparation of the conjugated antibody solutions. For the pair C1, the conjugate solution contains the 4G10E12 monoclonal antibody, in the form of a Fab' fragment, coupled to alkaline phosphatase. For the pair C2, the conjugate solution contains the 5G5A10 monoclonal antibody, in the form of a Fab' fragment, coupled to alkaline phosphatase. The conjugated antibodies were diluted to approximately 0.1 µg/ml in a Tris/NaCl BSA buffer, pH 6.5.

Immunoassay. As soon as the VIDAS® tip is in contact with the sample, the immunological reaction begins since the capture antibodies are immobilized on this tip. The automated device mixes the sample to be tested (89.6 µl) with 226 µl of the conjugate solution. The incubation lasts approximately 10 minutes at 37° C. and enables the specific binding of the AMH to, on the one hand, the antibody adsorbed onto the cone and to, on the other hand, the conjugated antibody (detection antibody). The unbound components are then removed by means of 3 washes with a 54 mM Tris buffer, pH 7.3, containing 154 mM NaCl and 0.55% Tween 20. During the final step of visualization, the 4-methylumbelliferyl phosphate substrate is suctioned and then discharged in the tip; the enzyme of the conjugated antibodies catalyzes the reaction for hydrolysis of this substrate to 4-methylumbelliferone, the emitted fluorescence of which is measured at 450 nm. The value of the fluorescence signal (RFV=relative fluorescence value) is proportional to the concentration of the antigen present in the sample.

6.2. AMH Assaying of the Samples Having Experienced Various Storage Conditions

Eight pools of natural samples from women between the ages of 19 and 52 were assayed in parallel with the commercial AMH Gen II Assay kit (Beckman Coulter) and with two pairs of antibodies (C1 and C2) on the VIDAS® automated device. Each sample pool consists of 3 sera from women that come from an Etablissement Français du Sang (EFS) [French Blood Bank] of the Rhône Alps region.

These samples were tested less than 4 hours after the taking of the samples corresponding to the time T0, then after 24 hours of storage at +2/8° C., after 7 days of storage at +2/8° C. and after 7 days of storage at −19/−31° C. corresponding to the various storage conditions of these samples.

For the kit in microplate form, the respective doses were calculated as a function of the range recommended by the producer. The ratios of the doses obtained for each storage condition relative to the dose obtained at T0 were then calculated. For the VIDAS® automated device, the fluorescence signals (RFV=Relative fluorescence value) obtained with each of the 2 pairs of antibodies, for each storage condition, were used to calculate the ratios with respect to the fluorescence signals obtained at T0. The results obtained are presented in table 8.

TABLE 8 ratio of the AMH doses or signals obtained after storage under various conditions and at T0 (T/T0 ratio).

| | 24 h at +2/8° C. | | | 7 days at +2/8° C. | | | 7 days at −19/−31° C. | | |
|---|---|---|---|---|---|---|---|---|---|
| | C1 | C2 | REF | C1 | C2 | REF | C1 | C2 | REF |
| Pool 001 | 0.99 | 1.00 | 1.10 | 0.95 | 1.06 | 1.14 | 0.98 | 0.99 | 1.20 |
| Pool 002 | 0.98 | 1.04 | 1.27 | 0.96 | 1.13 | 1.20 | 0.99 | 1.03 | 1.30 |
| Pool 003 | 0.98 | 1.00 | 1.14 | 0.96 | 1.04 | 1.05 | 1.01 | 1.02 | 1.07 |
| Pool 004 | 1.01 | 0.99 | 1.58 | 0.97 | 1.08 | 1.57 | 0.99 | 1.02 | 1.73 |
| Pool 005 | 0.96 | 1.02 | 1.46 | 0.95 | 1.09 | 1.33 | 0.97 | 1.01 | 1.24 |
| Pool 006 | 1.00 | 1.01 | 1.35 | 0.97 | 1.10 | 1.40 | 0.97 | 0.99 | 1.35 |
| Pool 007 | 0.97 | 1.03 | 1.43 | 0.96 | 1.11 | 1.66 | 0.95 | 1.01 | 1.51 |
| Pool 008 | 0.99 | 1.06 | 1.34 | 0.95 | 1.07 | 1.34 | 1.00 | 1.03 | 1.35 |
| Mean | 0.99 | 1.02 | 1.33 | 0.96 | 1.09 | 1.34 | 0.98 | 1.01 | 1.34 |
| Min | 0.96 | 0.99 | 1.10 | 0.95 | 1.04 | 1.05 | 0.95 | 0.99 | 1.07 |
| Max | 1.01 | 1.06 | 1.58 | 0.97 | 1.13 | 1.66 | 1.01 | 1.03 | 1.73 |

C1: VIDAS ® assay with 5G5A10 as capture antibody and 4G10E12 as detection antibody;
C2: VIDAS ® assay with 8C5B10H5 as capture antibody and 5G5A10 as detection antibody;
REF: AMH Gen II microplate assay.

The closer to the T/T0 ratio is to 1, the less variability there is, over time or according to the storage conditions, in the amounts of AMH detected. The AMH assays using the C1 or C2 pair always give the same result, regardless of the prior storage conditions of the sample: the T/T0 ratio is 0.99 (C1) and 1.02 (C2) on average when the sample was stored for 24 h at +2/8° C. These values are very close to 1, whereas the reference kit displays a mean ratio of 1.33 indicating that the dose measured is on average multiplied by 1.33. The same type of observation is made for the other storage conditions tested.

In summary, the 5G5A10 antibody recognizes a non-linear epitope of the 157-255 zone of human AMH, the 4G10E12 antibody recognizes a non-linear epitope of the 256-451 zone of human AMH, the 8C5B10H5 antibody recognizes a linear epitope (aa 508-519 of human AMH) in the mature region of AMH, the antibodies of the AMH Gen II Assay kit are both directed against linear epitopes of the mature region.

The antibody pairs C1 and C2 make it possible to develop AMH immunoassays which are robust and the result of which does not vary as a function of the prior storage conditions of the sample.

Example 7: Analytical Sensitivity of VIDAS® AMH

The analytical sensitivity of the VIDAS® AMH immunoassay (pair C1) described in example 6 was compared to that of assays according to the prior art. In order to be able to compare the antibody pairs under similar conditions, the entire experiment was carried out on the VIDAS® automated device. The tips were coated either with the 5G5A10 antibody (antibody recognizing the C-terminal portion of the pro region of AMH), or with the AA012 antibody (commercial antibody—AnshLabs) according to the procedure explained in example 6. For the detection step, two conjugates were compared: the 4G10E12 antibody and the AA011 antibody (commercial antibody—AnshLabs). Both were conjugated to alkaline phosphatase according to the procedure of example 6. The 4G10E12 conjugate was used at 180 ng/ml, the AA011 conjugate at 500 ng/ml. The 4G10E12 conjugate, which recognizes the C-terminal portion of the pro region of AMH, is thus used in a much lower amount compared with the commercial antibody, which is entirely unexpected.

A standard range ranging from 0.055 to 11 ng/ml of AMH was prepared by diluting sera for which the AMH concentrations were known, in serum from a menopausal woman (negligible AMH concentration), then measured using the following 3 assay formats:

Pair C1: capture 5G5A10+detection 4G10E12
AnshLabs pair: capture AA012+detection AA011
Mixed pair: capture 5G5A10+detection AA011
The results are presented in table 9.

TABLE 9

Comparison of the RFV signals and of the S/N ratios obtained with various antibody pairs by VIDAS ® for the standard range

| | VIDAS RFV Signal | | | VIDAS RFV/RFV0 | | |
|---|---|---|---|---|---|---|
| Capture | 5G5A10 | AA012 | 5G5A10 | 5G5A10 | AA012 | 5G5A10 |
| Detection | 4G10E12 | AA011 | AA011 | 4G10E12 | AA011 | AA011 |
| (conc ng/ml) | (180) | (500) | (500) | (180) | (500) | (500) |
| AMH ng/ml | RFV | RFV | RFV | S/N | S/N | S/N |
| 0 | 1 | 45 | 7 | | | |
| 0.055 | 51 | 81 | 53 | 51 | 2 | 8 |
| 0.11 | 92 | 113 | 91 | 92 | 3 | 13 |
| 0.275 | 224 | 209 | 221 | 224 | 5 | 32 |
| 0.9 | 916 | 735 | 910 | 916 | 16 | 130 |
| 2.1 | 2113 | 1602 | 2097 | 2113 | 36 | 300 |
| 4 | 3817 | 2938 | 3816 | 3817 | 65 | 545 |
| 6.3 | 4839 | 3915 | 4891 | 4839 | 87 | 699 |
| 8.7 | 5672 | 4810 | 5764 | 5672 | 107 | 823 |
| 11 | 6335 | 5392 | 6404 | 6335 | 120 | 915 |

S/N = "signal/noise" ratio.
For a given assay format, ratio of the RFV signal to the RFV signal of point 0 of the range (without AMH).

The pair C1 (5G5A10 & 4G10E12) exhibits excellent signal dynamics and an extremely low background noise (1 RFV at point 0). The pair according to the prior art AA012 & AA011 exhibits poorer signal dynamics (5392 RFV for 11 ng/ml, instead of 6335 RFV for the pair C1) and especially a considerable background noise of 45 RFV. The mixed pair (5G5A10 & AA011) has signal dynamics comparable to the pair C1 (same capture antibody). The background noise (7 RFV) is considerably lower than for the pair AA012 & AA011, but remains higher than for the pair C1. As can be seen, in terms of the signal/noise (S/N) ratios, the assay that is analytically the most sensitive is the one which uses the pair C1, then the one with the mixed pair, and in last place the one with the AnshLabs pair.

Example 8: Analytical Specificity of the VIDAS AMH Assay

The analytical specificity of the VIDAS AMH assay (pair C1) described in example 6 was established by analyzing compounds with cross reactivity. These compounds were added in overload amounts to serum samples containing 1 ng/ml and 4 ng/ml of AMH. The results of this study are summarized in table 10:

TABLE 10

Cross reactivities of the VIDAS ® AMH assay

| Compound tested | Concentration tested | % Cross reactivity |
|---|---|---|
| Activin A | 100 ng/ml | 0.10% |
| Inhibin A | 100 ng/ml | 0.12% |
| LH | 500 IU/l | 0.21% |
| FSH | 500 IU/l | 0.23% |

No significant cross reactivity was detected at the concentrations tested. The VIDAS AMH assay exhibits excellent analytical specificity.

Example 9: Accuracy of the VIDAS AMH Assay

The study of accuracy of the VIDAS AMH assay (pair C1) was carried out using a panel of human samples representative of 5 concentration levels of the measurement range. For each concentration level, the repeatability (intra-series accuracy), the intra-batch accuracy and the intra-laboratory accuracy (intra-instrument inter-batch accuracy) were estimated. The values obtained during this study are reported in table 11:

TABLE 11

Accuracy of the VIDAS AMH assay

| N (number of repetitions) | Concentration level (ng/ml) | % CV Repeatability | % CV Intra-batch | % CV Intra-laboratory |
|---|---|---|---|---|
| 519 | 0.22 | 4.1 | 6.6 | 8.3 |
| 520 | 1.08 | 4.4 | 8.0 | 9.9 |
| 520 | 2.99 | 4.4 | 7.4 | 9.8 |
| 520 | 5.45 | 4.8 | 7.6 | 8.9 |
| 520 | 7.37 | 4.4 | 8.2 | 10.6 |

As this very wide study shows, the VIDAS AMH assay exhibits good reproducibility: the coefficient of variation (CV) between different batches does not exceed 11%.

LITERATURE REFERENCES

Arce J C, et al., 2014, Fertility and Sterility, 102(6): 1633-40

Boersma Y L, Plückthun A, 2011, Curr. Opin. Biotechnol, 22: 849-857

Chai J and Howie A F, 2014, European Journal of Cancer, 50(14): 2367-74

Dewailly D, et al., 2014, The physiology and clinical utility of anti-Müllerian hormone in women, Human Reproduction Update, 20(3): 370-85

Ellington A D and Szostak J W., 1990, Nature, 346: 818-822

Falkenberg F W, 1998, Res Immunol 149(6): 560-570.

Fong S L, et al., 2015, European Journal of Obstetrics & Gynecology and Reproductive Biology, 186: 75-9

Han X et al., 2014, Hum Reprod, 29(5): 1042-1048.

Hudson P L et al., 1990, J Clin Endocrinol Metab, 70: 16-22.

Kelsey T W, et al., 2011, PLoS ONE, 6(7): e22024

Kohler G and Milstein C, 1975, Nature, 256: 495-497.

Kohler G et al., 1976, Eur J Immunol, 6: 292-295.

Kumar A et al., 2010, J Immunol Methods, 362: 51-59.

Lee M et al., 1996, J Clin Endocrinol Metab, 81: 571-576.

Long W Q et al., 2000, J Clin Endocrinol Metab, 85(2): 540-544.

Pankhurst M. W. et al, 2016, Physiological Reports, 4(9): 1-10

Zec I et al., 2011, Biochemia Medica, 21(3):219-30.

The invention claimed is:

1. A method for preparing anti-mammalian anti-Müllerian hormone (AMH) antibodies, comprising:
   (i) immunizing an animal with an immunogen comprising an AMH polypeptide or a polynucleotide encoding the AMH polypeptide, the AMH polypeptide comprising a sequence selected from the group consisting of:
   the human sequence of SEQ ID No. 1,
   the equine sequence of SEQ ID No. 14,
   the canine sequence of SEQ ID No. 23, and
   the bovine sequence of SEQ ID No. 32;
   (ii) preparing hybridomas from cells of a lymphoid organ of the animal immunized with the immunogen;
   (iii) selecting one or more of the hybridomas that each secrete an antibody recognizing a non-linear epitope of a sequence selected from the group consisting of:
   the human sequence of SEQ ID No. 1,
   the equine sequence of SEQ ID No. 14,
   the canine sequence of SEQ ID No. 23, and
   the bovine sequence of SEQ ID No. 32,
   the non-linear epitope being located at a median portion of the pro region of AMH, by contacting the antibody with an AMH polypeptide selected from the group consisting of:
   the sequence of SEQ ID No. 8, or a fragment of SEQ ID No. 8 comprising SEQ ID No. 1,
   the sequence of SEQ ID No. 20, or a fragment of SEQ ID No. 20 comprising SEQ ID No. 14,
   the sequence of SEQ ID No. 29, or a fragment of SEQ ID No. 29 comprising SEQ ID No. 23, and
   the sequence of SEQ ID No. 41, or a fragment of SEQ ID No. 41 comprising SEQ ID No. 32; and
   (iv) producing anti-AMH antibodies by culturing the selected hybridomas.

2. The method as claimed in claim 1, wherein the antibody does not recognize linear epitopes of SEQ ID No. 45 to SEQ ID No. 56.

3. The method as claimed in claim 1, wherein:
   the AMH polypeptide is the SEQ ID No. 8, or a fragment of SEQ ID No. 8 comprising SEQ ID No. 1, and
   the one or more selected hybridomas each secrete an antibody recognizing a non-linear epitope of the human sequence of SEQ ID No. 1.

4. The method as claimed in claim 3, wherein the AMH polypeptide comprises SEQ ID No. 10.

5. The method as claimed in claim 3, wherein the antibody does not recognize any of SEQ ID No. 11, SEQ ID No. 12, and SEQ ID No. 13.

6. The method as claimed in claim 1, wherein:
   the AMH polypeptide is the SEQ ID No. 20, or a fragment of SEQ ID No. 20 comprising SEQ ID No. 14, and
   the one or more selected hybridomas each secrete an antibody recognizing a non-linear epitope of the equine sequence of SEQ ID No. 14.

7. The method as claimed in claim 6, wherein the antibody does not recognize any of SEQ ID No. 21 and SEQ ID No. 22.

8. The method as claimed in claim 1, wherein:
   the AMH polypeptide is the SEQ ID No. 29, or a fragment of SEQ ID No. 29 comprising SEQ ID No. 23, and
   the one or more selected hybridomas each secrete an antibody recognizing a non-linear epitope of the canine sequence of SEQ ID No. 23.

9. The method as claimed in claim 8, wherein the antibody does not recognize any of SEQ ID No. 30 and SEQ ID No. 31.

10. The method as claimed in claim 1, wherein:
the AMH polypeptide is the SEQ ID No. 41, or a fragment of SEQ ID No. 41 comprising SEQ ID No. 32, and
the one or more selected hybridomas each secrete an antibody recognizing a non-linear epitope of the bovine sequence of SEQ ID No. 32.

11. The method as claimed in claim 10, wherein the antibody does not recognize any of SEQ ID No. 42, SEQ ID No. 43, and SEQ ID No. 44.

* * * * *

SEQUENCE LISTING

```
<160> NUMBER OF SEQ ID NOS: 158

<210> SEQ ID NO 1
<211> LENGTH: 99
<212> TYPE: PRT
<213> ORGANISM: artificial sequence
<220> FEATURE:
<223> OTHER INFORMATION: polypeptide

<400> SEQUENCE: 1

Gly Pro Pro Glu Leu Ala Leu Leu Val Leu Tyr Pro Gly Pro Gly Pro
1               5                   10                  15

Glu Val Thr Val Thr Arg Ala Gly Leu Pro Gly Ala Gln Ser Leu Cys
            20                  25                  30

Pro Ser Arg Asp Thr Arg Tyr Leu Val Leu Ala Val Asp Arg Pro Ala
        35                  40                  45

Gly Ala Trp Arg Gly Ser Gly Leu Ala Leu Thr Leu Gln Pro Arg Gly
```

Glu Asp Ser Arg Leu Ser Thr Ala Arg Leu Gln Ala Leu Leu Phe Gly
65                  70                  75                  80

Asp Asp His Arg Cys Phe Thr Arg Met Thr Pro Ala Leu Leu Leu Leu
                85                  90                  95

Pro Arg Ser

<210> SEQ ID NO 2
<211> LENGTH: 560
<212> TYPE: PRT
<213> ORGANISM: human

<400> SEQUENCE: 2

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Pro Ala Val
                20                  25                  30

Gly Thr Ser Gly Leu Ile Phe Arg Glu Asp Leu Asp Trp Pro Pro Gly
            35                  40                  45

Ser Pro Gln Glu Pro Leu Cys Leu Val Ala Leu Gly Gly Asp Ser Asn
50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Leu Pro Arg Ser Glu
                245                 250                 255

Pro Ala Pro Leu Pro Ala His Gly Gln Leu Asp Thr Val Pro Phe Pro
            260                 265                 270

Pro Pro Arg Pro Ser Ala Glu Leu Glu Glu Ser Pro Pro Ser Ala Asp
        275                 280                 285

Pro Phe Leu Glu Thr Leu Thr Arg Leu Val Arg Ala Leu Arg Val Pro
            290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu

```
                    325                 330                 335

Glu Arg Leu Leu Asp Gly Glu Glu Pro Leu Leu Leu Leu Arg Pro
            340                 345                 350

Thr Ala Ala Thr Thr Gly Asp Pro Ala Pro Leu His Asp Pro Thr Ser
                355                 360                 365

Ala Pro Trp Ala Thr Ala Leu Ala Arg Arg Val Ala Ala Glu Leu Gln
            370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
            405                 410                 415

Gly Leu Gly Asp Pro Leu Arg Ala Leu Leu Leu Lys Ala Leu Gln
            420                 425                 430

Gly Leu Arg Val Glu Trp Arg Gly Arg Asp Pro Arg Gly Pro Gly Arg
            435                 440                 445

Ala Gln Arg Ser Ala Gly Ala Thr Ala Ala Asp Gly Pro Cys Ala Leu
            450                 455                 460

Arg Glu Leu Ser Val Asp Leu Arg Ala Glu Arg Ser Val Leu Ile Pro
465                 470                 475                 480

Glu Thr Tyr Gln Ala Asn Asn Cys Gln Gly Val Cys Gly Trp Pro Gln
                485                 490                 495

Ser Asp Arg Asn Pro Arg Tyr Gly Asn His Val Val Leu Leu Leu Lys
            500                 505                 510

Met Gln Val Arg Gly Ala Ala Leu Ala Arg Pro Pro Cys Cys Val Pro
            515                 520                 525

Thr Ala Tyr Ala Gly Lys Leu Leu Ile Ser Leu Ser Glu Glu Arg Ile
            530                 535                 540

Ser Ala His His Val Pro Asn Met Val Ala Thr Glu Cys Gly Cys Arg
545                 550                 555                 560

<210> SEQ ID NO 3
<211> LENGTH: 542
<212> TYPE: PRT
<213> ORGANISM: artificial sequence
<220> FEATURE:
<223> OTHER INFORMATION: poplypeptide

<400> SEQUENCE: 3

Leu Leu Gly Thr Glu Ala Leu Arg Ala Glu Glu Pro Ala Val Gly Thr
1               5                   10                  15

Ser Gly Leu Ile Phe Arg Glu Asp Leu Asp Trp Pro Pro Gly Ser Pro
                20                  25                  30

Gln Glu Pro Leu Cys Leu Val Ala Leu Gly Gly Asp Ser Asn Gly Ser
            35                  40                  45

Ser Ser Pro Leu Arg Val Val Gly Ala Leu Ser Ala Tyr Glu Gln Ala
50                  55                  60

Phe Leu Gly Ala Val Gln Arg Ala Arg Trp Gly Pro Arg Asp Leu Ala
65                  70                  75                  80

Thr Phe Gly Val Cys Asn Thr Gly Asp Arg Gln Ala Ala Leu Pro Ser
                85                  90                  95

Leu Arg Arg Leu Gly Ala Trp Leu Arg Asp Pro Gly Gly Gln Arg Leu
            100                 105                 110

Val Val Leu His Leu Glu Glu Val Thr Trp Glu Pro Thr Pro Ser Leu
            115                 120                 125

Arg Phe Gln Glu Pro Pro Pro Gly Gly Ala Gly Pro Pro Glu Leu Ala
```

```
            130                 135                 140
Leu Leu Val Leu Tyr Pro Gly Pro Gly Pro Glu Val Thr Val Thr Arg
145                 150                 155                 160

Ala Gly Leu Pro Gly Ala Gln Ser Leu Cys Pro Ser Arg Asp Thr Arg
                165                 170                 175

Tyr Leu Val Leu Ala Val Asp Arg Pro Ala Gly Ala Trp Arg Gly Ser
            180                 185                 190

Gly Leu Ala Leu Thr Leu Gln Pro Arg Gly Glu Asp Ser Arg Leu Ser
        195                 200                 205

Thr Ala Arg Leu Gln Ala Leu Leu Phe Gly Asp Asp His Arg Cys Phe
210                 215                 220

Thr Arg Met Thr Pro Ala Leu Leu Leu Leu Pro Arg Ser Glu Pro Ala
225                 230                 235                 240

Pro Leu Pro Ala His Gly Gln Leu Asp Thr Val Pro Phe Pro Pro Pro
                245                 250                 255

Arg Pro Ser Ala Glu Leu Glu Glu Ser Pro Pro Ser Ala Asp Pro Phe
                260                 265                 270

Leu Glu Thr Leu Thr Arg Leu Val Arg Ala Leu Arg Val Pro Pro Ala
            275                 280                 285

Arg Ala Ser Ala Pro Arg Leu Ala Leu Asp Pro Asp Ala Leu Ala Gly
290                 295                 300

Phe Pro Gln Gly Leu Val Asn Leu Ser Asp Pro Ala Ala Leu Glu Arg
305                 310                 315                 320

Leu Leu Asp Gly Glu Glu Pro Leu Leu Leu Leu Arg Pro Thr Ala
                325                 330                 335

Ala Thr Thr Gly Asp Pro Ala Pro Leu His Asp Pro Thr Ser Ala Pro
            340                 345                 350

Trp Ala Thr Ala Leu Ala Arg Arg Val Ala Ala Glu Leu Gln Ala Ala
                355                 360                 365

Ala Ala Glu Leu Arg Ser Leu Pro Gly Leu Pro Pro Ala Thr Ala Pro
        370                 375                 380

Leu Leu Ala Arg Leu Leu Ala Leu Cys Pro Gly Gly Pro Gly Gly Leu
385                 390                 395                 400

Gly Asp Pro Leu Arg Ala Leu Leu Leu Lys Ala Leu Gln Gly Leu
                405                 410                 415

Arg Val Glu Trp Arg Gly Arg Asp Pro Arg Gly Pro Gly Arg Ala Gln
            420                 425                 430

Arg Ser Ala Gly Ala Thr Ala Ala Asp Gly Pro Cys Ala Leu Arg Glu
        435                 440                 445

Leu Ser Val Asp Leu Arg Ala Glu Arg Ser Val Leu Ile Pro Glu Thr
450                 455                 460

Tyr Gln Ala Asn Asn Cys Gln Gly Val Cys Gly Trp Pro Gln Ser Asp
465                 470                 475                 480

Arg Asn Pro Arg Tyr Gly Asn His Val Val Leu Leu Leu Lys Met Gln
                485                 490                 495

Val Arg Gly Ala Ala Leu Ala Arg Pro Pro Cys Cys Val Pro Thr Ala
            500                 505                 510

Tyr Ala Gly Lys Leu Leu Ile Ser Leu Ser Glu Glu Arg Ile Ser Ala
        515                 520                 525

His His Val Pro Asn Met Val Ala Thr Glu Cys Gly Cys Arg
530                 535                 540

<210> SEQ ID NO 4
```

<211> LENGTH: 535
<212> TYPE: PRT
<213> ORGANISM: artificial sequence
<220> FEATURE:
<223> OTHER INFORMATION: polypeptide

<400> SEQUENCE: 4

```
Arg Ala Glu Glu Pro Ala Val Gly Thr Ser Gly Leu Ile Phe Arg Glu
1               5                   10                  15

Asp Leu Asp Trp Pro Pro Gly Ser Pro Gln Glu Pro Leu Cys Leu Val
            20                  25                  30

Ala Leu Gly Gly Asp Ser Asn Gly Ser Ser Pro Leu Arg Val Val
        35                  40                  45

Gly Ala Leu Ser Ala Tyr Glu Gln Ala Phe Leu Gly Ala Val Gln Arg
50                  55                  60

Ala Arg Trp Gly Pro Arg Asp Leu Ala Thr Phe Gly Val Cys Asn Thr
65                  70                  75                  80

Gly Asp Arg Gln Ala Ala Leu Pro Ser Leu Arg Arg Leu Gly Ala Trp
                85                  90                  95

Leu Arg Asp Pro Gly Gly Gln Arg Leu Val Val Leu His Leu Glu Glu
            100                 105                 110

Val Thr Trp Glu Pro Thr Pro Ser Leu Arg Phe Gln Glu Pro Pro Pro
        115                 120                 125

Gly Gly Ala Gly Pro Pro Glu Leu Ala Leu Leu Val Leu Tyr Pro Gly
130                 135                 140

Pro Gly Pro Glu Val Thr Val Thr Arg Ala Gly Leu Pro Gly Ala Gln
145                 150                 155                 160

Ser Leu Cys Pro Ser Arg Asp Thr Arg Tyr Leu Val Leu Ala Val Asp
                165                 170                 175

Arg Pro Ala Gly Ala Trp Arg Gly Ser Gly Leu Ala Leu Thr Leu Gln
            180                 185                 190

Pro Arg Gly Glu Asp Ser Arg Leu Ser Thr Ala Arg Leu Gln Ala Leu
        195                 200                 205

Leu Phe Gly Asp Asp His Arg Cys Phe Thr Arg Met Thr Pro Ala Leu
210                 215                 220

Leu Leu Leu Pro Arg Ser Glu Pro Ala Pro Leu Pro Ala His Gly Gln
225                 230                 235                 240

Leu Asp Thr Val Pro Phe Pro Pro Arg Pro Ser Ala Glu Leu Glu
                245                 250                 255

Glu Ser Pro Pro Ser Ala Asp Pro Phe Leu Glu Thr Leu Thr Arg Leu
            260                 265                 270

Val Arg Ala Leu Arg Val Pro Pro Ala Arg Ala Ser Ala Pro Arg Leu
        275                 280                 285

Ala Leu Asp Pro Asp Ala Leu Ala Gly Phe Pro Gln Gly Leu Val Asn
290                 295                 300

Leu Ser Asp Pro Ala Ala Leu Glu Arg Leu Leu Asp Gly Glu Glu Pro
305                 310                 315                 320

Leu Leu Leu Leu Leu Arg Pro Thr Ala Ala Thr Thr Gly Asp Pro Ala
                325                 330                 335

Pro Leu His Asp Pro Thr Ser Ala Pro Trp Ala Thr Ala Leu Ala Arg
            340                 345                 350

Arg Val Ala Ala Glu Leu Gln Ala Ala Ala Glu Leu Arg Ser Leu
        355                 360                 365

Pro Gly Leu Pro Pro Ala Thr Ala Pro Leu Leu Ala Arg Leu Leu Ala
370                 375                 380
```

Leu Cys Pro Gly Gly Pro Gly Gly Leu Gly Asp Pro Leu Arg Ala Leu
385                 390                 395                 400

Leu Leu Leu Lys Ala Leu Gln Gly Leu Arg Val Glu Trp Arg Gly Arg
            405                 410                 415

Asp Pro Arg Gly Pro Gly Arg Ala Gln Arg Ser Ala Gly Ala Thr Ala
        420                 425                 430

Ala Asp Gly Pro Cys Ala Leu Arg Glu Leu Ser Val Asp Leu Arg Ala
        435                 440                 445

Glu Arg Ser Val Leu Ile Pro Glu Thr Tyr Gln Ala Asn Asn Cys Gln
    450                 455                 460

Gly Val Cys Gly Trp Pro Gln Ser Asp Arg Asn Pro Arg Tyr Gly Asn
465                 470                 475                 480

His Val Val Leu Leu Lys Met Gln Val Arg Gly Ala Ala Leu Ala
            485                 490                 495

Arg Pro Pro Cys Cys Val Pro Thr Ala Tyr Ala Gly Lys Leu Leu Ile
            500                 505                 510

Ser Leu Ser Glu Glu Arg Ile Ser Ala His His Val Pro Asn Met Val
    515                 520                 525

Ala Thr Glu Cys Gly Cys Arg
    530                 535

<210> SEQ ID NO 5
<211> LENGTH: 451
<212> TYPE: PRT
<213> ORGANISM: artificial sequence
<220> FEATURE:
<223> OTHER INFORMATION: polypeptide

<400> SEQUENCE: 5

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
            85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
            115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

```
Gly Ser Gly Leu Ala Leu Thr Leu Gln Pro Arg Gly Glu Asp Ser Arg
        210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser Glu
                245                 250                 255

Pro Ala Pro Leu Pro Ala His Gly Gln Leu Asp Thr Val Pro Phe Pro
                260                 265                 270

Pro Pro Arg Pro Ser Ala Glu Leu Glu Ser Pro Pro Ser Ala Asp
                275                 280                 285

Pro Phe Leu Glu Thr Leu Thr Arg Leu Val Arg Ala Leu Arg Val Pro
                290                 295                 300

Pro Ala Arg Ala Ser Ala Pro Arg Leu Ala Leu Asp Pro Asp Ala Leu
305                 310                 315                 320

Ala Gly Phe Pro Gln Gly Leu Val Asn Leu Ser Asp Pro Ala Ala Leu
                325                 330                 335

Glu Arg Leu Leu Asp Gly Glu Glu Pro Leu Leu Leu Leu Arg Pro
                340                 345                 350

Thr Ala Ala Thr Thr Gly Asp Pro Ala Pro Leu His Asp Pro Thr Ser
                355                 360                 365

Ala Pro Trp Ala Thr Ala Leu Ala Arg Arg Val Ala Ala Glu Leu Gln
                370                 375                 380

Ala Ala Ala Ala Glu Leu Arg Ser Leu Pro Gly Leu Pro Pro Ala Thr
385                 390                 395                 400

Ala Pro Leu Leu Ala Arg Leu Leu Ala Leu Cys Pro Gly Gly Pro Gly
                405                 410                 415

Gly Leu Gly Asp Pro Leu Arg Ala Leu Leu Leu Lys Ala Leu Gln
                420                 425                 430

Gly Leu Arg Val Glu Trp Arg Gly Arg Asp Pro Arg Gly Pro Gly Arg
                435                 440                 445

Ala Gln Arg
        450

<210> SEQ ID NO 6
<211> LENGTH: 433
<212> TYPE: PRT
<213> ORGANISM: artificial sequence
<220> FEATURE:
<223> OTHER INFORMATION: polypeptide

<400> SEQUENCE: 6

Leu Leu Gly Thr Glu Ala Leu Arg Ala Glu Glu Pro Ala Val Gly Thr
1               5                   10                  15

Ser Gly Leu Ile Phe Arg Glu Asp Leu Asp Trp Pro Pro Gly Ser Pro
                20                  25                  30

Gln Glu Pro Leu Cys Leu Val Ala Leu Gly Gly Asp Ser Asn Gly Ser
                35                  40                  45

Ser Ser Pro Leu Arg Val Val Gly Ala Leu Ser Ala Tyr Glu Gln Ala
50                  55                  60

Phe Leu Gly Ala Val Gln Arg Ala Arg Trp Gly Pro Arg Asp Leu Ala
65                  70                  75                  80

Thr Phe Gly Val Cys Asn Thr Gly Asp Arg Gln Ala Ala Leu Pro Ser
                85                  90                  95

Leu Arg Arg Leu Gly Ala Trp Leu Arg Asp Pro Gly Gly Gln Arg Leu
                100                 105                 110
```

Val Val Leu His Leu Glu Glu Val Thr Trp Glu Pro Thr Pro Ser Leu
        115                 120                 125

Arg Phe Gln Glu Pro Pro Gly Gly Ala Gly Pro Pro Glu Leu Ala
130                 135                 140

Leu Leu Val Leu Tyr Pro Gly Pro Gly Pro Glu Val Thr Val Thr Arg
145                 150                 155                 160

Ala Gly Leu Pro Gly Ala Gln Ser Leu Cys Pro Ser Arg Asp Thr Arg
                165                 170                 175

Tyr Leu Val Leu Ala Val Asp Arg Pro Ala Gly Ala Trp Arg Gly Ser
                180                 185                 190

Gly Leu Ala Leu Thr Leu Gln Pro Arg Gly Glu Asp Ser Arg Leu Ser
                195                 200                 205

Thr Ala Arg Leu Gln Ala Leu Leu Phe Gly Asp Asp His Arg Cys Phe
210                 215                 220

Thr Arg Met Thr Pro Ala Leu Leu Leu Pro Arg Ser Glu Pro Ala
225                 230                 235                 240

Pro Leu Pro Ala His Gly Gln Leu Asp Thr Val Pro Phe Pro Pro Pro
                245                 250                 255

Arg Pro Ser Ala Glu Leu Glu Glu Ser Pro Ser Ala Asp Pro Phe
            260                 265                 270

Leu Glu Thr Leu Thr Arg Leu Val Arg Ala Leu Arg Val Pro Pro Ala
            275                 280                 285

Arg Ala Ser Ala Pro Arg Leu Ala Leu Asp Pro Asp Ala Leu Ala Gly
            290                 295                 300

Phe Pro Gln Gly Leu Val Asn Leu Ser Asp Pro Ala Ala Leu Glu Arg
305                 310                 315                 320

Leu Leu Asp Gly Glu Glu Pro Leu Leu Leu Leu Arg Pro Thr Ala
                325                 330                 335

Ala Thr Thr Gly Asp Pro Ala Pro Leu His Asp Pro Thr Ser Ala Pro
            340                 345                 350

Trp Ala Thr Ala Leu Ala Arg Arg Val Ala Ala Glu Leu Gln Ala Ala
            355                 360                 365

Ala Ala Glu Leu Arg Ser Leu Pro Gly Leu Pro Pro Ala Thr Ala Pro
370                 375                 380

Leu Leu Ala Arg Leu Leu Ala Leu Cys Pro Gly Gly Pro Gly Gly Leu
385                 390                 395                 400

Gly Asp Pro Leu Arg Ala Leu Leu Leu Lys Ala Leu Gln Gly Leu
                405                 410                 415

Arg Val Glu Trp Arg Gly Arg Asp Pro Arg Gly Pro Gly Arg Ala Gln
                420                 425                 430

Arg

<210> SEQ ID NO 7
<211> LENGTH: 426
<212> TYPE: PRT
<213> ORGANISM: artificial sequence
<220> FEATURE:
<223> OTHER INFORMATION: polypeptide

<400> SEQUENCE: 7

Arg Ala Glu Glu Pro Ala Val Gly Thr Ser Gly Leu Ile Phe Arg Glu
1               5                   10                  15

Asp Leu Asp Trp Pro Pro Gly Ser Pro Gln Glu Pro Leu Cys Leu Val
            20                  25                  30

Ala Leu Gly Gly Asp Ser Asn Gly Ser Ser Pro Leu Arg Val Val
            35                  40                  45

Gly Ala Leu Ser Ala Tyr Glu Gln Ala Phe Leu Gly Ala Val Gln Arg
 50                  55                  60

Ala Arg Trp Gly Pro Arg Asp Leu Ala Thr Phe Gly Val Cys Asn Thr
 65                  70                  75                  80

Gly Asp Arg Gln Ala Ala Leu Pro Ser Leu Arg Arg Leu Gly Ala Trp
                 85                  90                  95

Leu Arg Asp Pro Gly Gly Gln Arg Leu Val Val Leu His Leu Glu Glu
                100                 105                 110

Val Thr Trp Glu Pro Thr Pro Ser Leu Arg Phe Gln Glu Pro Pro Pro
            115                 120                 125

Gly Gly Ala Gly Pro Pro Glu Leu Ala Leu Leu Val Leu Tyr Pro Gly
130                 135                 140

Pro Gly Pro Glu Val Thr Val Thr Arg Ala Gly Leu Pro Gly Ala Gln
145                 150                 155                 160

Ser Leu Cys Pro Ser Arg Asp Thr Arg Tyr Leu Val Leu Ala Val Asp
                165                 170                 175

Arg Pro Ala Gly Ala Trp Arg Gly Ser Gly Leu Ala Leu Thr Leu Gln
            180                 185                 190

Pro Arg Gly Glu Asp Ser Arg Leu Ser Thr Ala Arg Leu Gln Ala Leu
        195                 200                 205

Leu Phe Gly Asp Asp His Arg Cys Phe Thr Arg Met Thr Pro Ala Leu
210                 215                 220

Leu Leu Pro Arg Ser Glu Pro Ala Pro Leu Pro Ala His Gly Gln
225                 230                 235                 240

Leu Asp Thr Val Pro Phe Pro Pro Arg Pro Ser Ala Glu Leu Glu
                245                 250                 255

Glu Ser Pro Pro Ser Ala Asp Pro Phe Leu Glu Thr Leu Thr Arg Leu
            260                 265                 270

Val Arg Ala Leu Arg Val Pro Ala Arg Ala Ser Ala Pro Arg Leu
            275                 280                 285

Ala Leu Asp Pro Asp Ala Leu Ala Gly Phe Pro Gln Gly Leu Val Asn
290                 295                 300

Leu Ser Asp Pro Ala Ala Leu Glu Arg Leu Leu Asp Gly Glu Glu Pro
305                 310                 315                 320

Leu Leu Leu Leu Leu Arg Pro Thr Ala Ala Thr Thr Gly Asp Pro Ala
                325                 330                 335

Pro Leu His Asp Pro Thr Ser Ala Pro Trp Ala Thr Ala Leu Ala Arg
            340                 345                 350

Arg Val Ala Ala Glu Leu Gln Ala Ala Ala Glu Leu Arg Ser Leu
            355                 360                 365

Pro Gly Leu Pro Pro Ala Thr Ala Pro Leu Leu Ala Arg Leu Leu Ala
370                 375                 380

Leu Cys Pro Gly Gly Pro Gly Leu Gly Asp Pro Leu Arg Ala Leu
385                 390                 395                 400

Leu Leu Leu Lys Ala Leu Gln Gly Leu Arg Val Glu Trp Arg Gly Arg
                405                 410                 415

Asp Pro Arg Gly Pro Gly Arg Ala Gln Arg
            420                 425

<210> SEQ ID NO 8
<211> LENGTH: 255
<212> TYPE: PRT

<213> ORGANISM: artificial sequence
<220> FEATURE:
<223> OTHER INFORMATION: polypeptide

<400> SEQUENCE: 8

```
Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
            20                  25                  30

Gly Thr Ser Gly Leu Ile Phe Arg Glu Asp Leu Asp Trp Pro Pro Gly
        35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
    130                 135                 140

Ser Leu Arg Phe Gln Glu Pro Pro Gly Gly Ala Gly Pro Pro Glu
145                 150                 155                 160

Leu Ala Leu Leu Val Leu Tyr Pro Gly Pro Gly Pro Glu Val Thr Val
                165                 170                 175

Thr Arg Ala Gly Leu Pro Gly Ala Gln Ser Leu Cys Pro Ser Arg Asp
            180                 185                 190

Thr Arg Tyr Leu Val Leu Ala Val Asp Arg Pro Ala Gly Ala Trp Arg
        195                 200                 205

Gly Ser Gly Leu Ala Leu Thr Leu Gln Pro Arg Gly Glu Asp Ser Arg
    210                 215                 220

Leu Ser Thr Ala Arg Leu Gln Ala Leu Leu Phe Gly Asp Asp His Arg
225                 230                 235                 240

Cys Phe Thr Arg Met Thr Pro Ala Leu Leu Leu Pro Arg Ser
                245                 250                 255
```

<210> SEQ ID NO 9
<211> LENGTH: 237
<212> TYPE: PRT
<213> ORGANISM: artificial sequence
<220> FEATURE:
<223> OTHER INFORMATION: polypeptide

<400> SEQUENCE: 9

```
Leu Leu Gly Thr Glu Ala Leu Arg Ala Glu Glu Pro Ala Val Gly Thr
1               5                   10                  15

Ser Gly Leu Ile Phe Arg Glu Asp Leu Asp Trp Pro Pro Gly Ser Pro
            20                  25                  30

Gln Glu Pro Leu Cys Leu Val Ala Leu Gly Gly Asp Ser Asn Gly Ser
        35                  40                  45

Ser Ser Pro Leu Arg Val Val Gly Ala Leu Ser Ala Tyr Glu Gln Ala
    50                  55                  60

Phe Leu Gly Ala Val Gln Arg Ala Arg Trp Gly Pro Arg Asp Leu Ala
65                  70                  75                  80
```

Thr Phe Gly Val Cys Asn Thr Gly Asp Arg Gln Ala Ala Leu Pro Ser
            85                  90                  95

Leu Arg Arg Leu Gly Ala Trp Leu Arg Asp Pro Gly Gly Gln Arg Leu
        100                 105                 110

Val Val Leu His Leu Glu Glu Val Thr Trp Glu Pro Thr Pro Ser Leu
        115                 120                 125

Arg Phe Gln Glu Pro Pro Gly Gly Ala Gly Pro Pro Glu Leu Ala
        130                 135                 140

Leu Leu Val Leu Tyr Pro Gly Pro Gly Pro Glu Val Thr Val Thr Arg
145                 150                 155                 160

Ala Gly Leu Pro Gly Ala Gln Ser Leu Cys Pro Ser Arg Asp Thr Arg
                165                 170                 175

Tyr Leu Val Leu Ala Val Asp Arg Pro Ala Gly Ala Trp Arg Gly Ser
                180                 185                 190

Gly Leu Ala Leu Thr Leu Gln Pro Arg Gly Glu Asp Ser Arg Leu Ser
                195                 200                 205

Thr Ala Arg Leu Gln Ala Leu Leu Phe Gly Asp Asp His Arg Cys Phe
        210                 215                 220

Thr Arg Met Thr Pro Ala Leu Leu Leu Leu Pro Arg Ser
225                 230                 235

<210> SEQ ID NO 10
<211> LENGTH: 230
<212> TYPE: PRT
<213> ORGANISM: artificial sequence
<220> FEATURE:
<223> OTHER INFORMATION: polypeptide

<400> SEQUENCE: 10

Arg Ala Glu Glu Pro Ala Val Gly Thr Ser Gly Leu Ile Phe Arg Glu
1               5                   10                  15

Asp Leu Asp Trp Pro Pro Gly Ser Pro Gln Glu Pro Leu Cys Leu Val
            20                  25                  30

Ala Leu Gly Gly Asp Ser Asn Gly Ser Ser Ser Pro Leu Arg Val Val
        35                  40                  45

Gly Ala Leu Ser Ala Tyr Glu Gln Ala Phe Leu Gly Ala Val Gln Arg
50                  55                  60

Ala Arg Trp Gly Pro Arg Asp Leu Ala Thr Phe Gly Val Cys Asn Thr
65                  70                  75                  80

Gly Asp Arg Gln Ala Ala Leu Pro Ser Leu Arg Arg Leu Gly Ala Trp
                85                  90                  95

Leu Arg Asp Pro Gly Gly Gln Arg Leu Val Val Leu His Leu Glu Glu
            100                 105                 110

Val Thr Trp Glu Pro Thr Pro Ser Leu Arg Phe Gln Glu Pro Pro
        115                 120                 125

Gly Gly Ala Gly Pro Pro Glu Leu Ala Leu Leu Val Leu Tyr Pro Gly
        130                 135                 140

Pro Gly Pro Glu Val Thr Val Thr Arg Ala Gly Leu Pro Gly Ala Gln
145                 150                 155                 160

Ser Leu Cys Pro Ser Arg Asp Thr Arg Tyr Leu Val Leu Ala Val Asp
                165                 170                 175

Arg Pro Ala Gly Ala Trp Arg Gly Ser Gly Leu Ala Leu Thr Leu Gln
            180                 185                 190

Pro Arg Gly Glu Asp Ser Arg Leu Ser Thr Ala Arg Leu Gln Ala Leu
        195                 200                 205

```
Leu Phe Gly Asp Asp His Arg Cys Phe Thr Arg Met Thr Pro Ala Leu
        210                 215                 220

Leu Leu Leu Pro Arg Ser
225                 230

<210> SEQ ID NO 11
<211> LENGTH: 156
<212> TYPE: PRT
<213> ORGANISM: artificial sequence
<220> FEATURE:
<223> OTHER INFORMATION: polypeptide

<400> SEQUENCE: 11

Met Arg Asp Leu Pro Leu Thr Ser Leu Ala Leu Val Leu Ser Ala Leu
1               5                   10                  15

Gly Ala Leu Leu Gly Thr Glu Ala Leu Arg Ala Glu Glu Pro Ala Val
                20                  25                  30

Gly Thr Ser Gly Leu Ile Phe Arg Glu Asp Leu Asp Trp Pro Pro Gly
            35                  40                  45

Ser Pro Gln Glu Pro Leu Cys Leu Val Ala Leu Gly Gly Asp Ser Asn
    50                  55                  60

Gly Ser Ser Ser Pro Leu Arg Val Val Gly Ala Leu Ser Ala Tyr Glu
65                  70                  75                  80

Gln Ala Phe Leu Gly Ala Val Gln Arg Ala Arg Trp Gly Pro Arg Asp
                85                  90                  95

Leu Ala Thr Phe Gly Val Cys Asn Thr Gly Asp Arg Gln Ala Ala Leu
            100                 105                 110

Pro Ser Leu Arg Arg Leu Gly Ala Trp Leu Arg Asp Pro Gly Gly Gln
        115                 120                 125

Arg Leu Val Val Leu His Leu Glu Glu Val Thr Trp Glu Pro Thr Pro
130                 135                 140

Ser Leu Arg Phe Gln Glu Pro Pro Gly Gly Ala
145                 150                 155

<210> SEQ ID NO 12
<211> LENGTH: 138
<212> TYPE: PRT
<213> ORGANISM: artificial sequence
<220> FEATURE:
<223> OTHER INFORMATION: polypeptide

<400> SEQUENCE: 12

Leu Leu Gly Thr Glu Ala Leu Arg Ala Glu Glu Pro Ala Val Gly Thr
1               5                   10                  15

Ser Gly Leu Ile Phe Arg Glu Asp Leu Asp Trp Pro Pro Gly Ser Pro
                20                  25                  30

Gln Glu Pro Leu Cys Leu Val Ala Leu Gly Gly Asp Ser Asn Gly Ser
            35                  40                  45

Ser Ser Pro Leu Arg Val Val Gly Ala Leu Ser Ala Tyr Glu Gln Ala
        50                  55                  60

Phe Leu Gly Ala Val Gln Arg Ala Arg Trp Gly Pro Arg Asp Leu Ala
65                  70                  75                  80

Thr Phe Gly Val Cys Asn Thr Gly Asp Arg Gln Ala Ala Leu Pro Ser
                85                  90                  95

Leu Arg Arg Leu Gly Ala Trp Leu Arg Asp Pro Gly Gly Gln Arg Leu
            100                 105                 110

Val Val Leu His Leu Glu Glu Val Thr Trp Glu Pro Thr Pro Ser Leu
        115                 120                 125
```

```
Arg Phe Gln Glu Pro Pro Pro Gly Gly Ala
        130                 135
```

<210> SEQ ID NO 13
<211> LENGTH: 131
<212> TYPE: PRT
<213> ORGANISM: artificial sequence
<220> FEATURE:
<223> OTHER INFORMATION: polypeptide

<400> SEQUENCE: 13

```
Arg Ala Glu Glu Pro Ala Val Gly Thr Ser Gly Leu Ile Phe Arg Glu
1               5                   10                  15

Asp Leu Asp Trp Pro Pro Gly Ser Pro Gln Glu Pro Leu Cys Leu Val
            20                  25                  30

Ala Leu Gly Gly Asp Ser Asn Gly Ser Ser Pro Leu Arg Val Val
        35                  40                  45

Gly Ala Leu Ser Ala Tyr Glu Gln Ala Phe Leu Gly Ala Val Gln Arg
    50                  55                  60

Ala Arg Trp Gly Pro Arg Asp Leu Ala Thr Phe Gly Val Cys Asn Thr
65                  70                  75                  80

Gly Asp Arg Gln Ala Ala Leu Pro Ser Leu Arg Arg Leu Gly Ala Trp
                85                  90                  95

Leu Arg Asp Pro Gly Gly Gln Arg Leu Val Val Leu His Leu Glu Glu
            100                 105                 110

Val Thr Trp Glu Pro Thr Pro Ser Leu Arg Phe Gln Glu Pro Pro Pro
        115                 120                 125

Gly Gly Ala
    130
```

<210> SEQ ID NO 14
<211> LENGTH: 99
<212> TYPE: PRT
<213> ORGANISM: artificial sequence
<220> FEATURE:
<223> OTHER INFORMATION: polypeptide

<400> SEQUENCE: 14

```
Asn Pro Leu Glu Pro Ala Leu Leu Val Leu Tyr Ala Gly Pro Gly Pro
1               5                   10                  15

Glu Val Thr Val Thr Gly Ala Gly Leu Pro Gly Ala Gln Ser Leu Cys
            20                  25                  30

Pro Ser Pro Asp Thr Arg Tyr Leu Ala Leu Ala Val Asp His Pro Ala
        35                  40                  45

Arg Ala Trp Arg His Pro Gly Leu Ile Leu Thr Leu Gln Pro Arg Gly
    50                  55                  60

Asp Gly Ala Pro Leu Ser Thr Ala Gln Leu Gln Thr Leu Leu Phe Gly
65                  70                  75                  80

Ala Asp Pro Arg Cys Phe Thr Arg Met Thr Pro Ala Leu Phe Leu Leu
                85                  90                  95

Gln Arg Pro
```

<210> SEQ ID NO 15
<211> LENGTH: 573
<212> TYPE: PRT
<213> ORGANISM: Equus caballus

<400> SEQUENCE: 15

```
Met Arg Ala Pro Ser Leu Ser Trp Leu Ala Leu Val Leu Ser Ala Val
1               5                   10                  15

Gly Ala Leu Leu Arg Ala Gly Thr Pro Gly Glu Glu Val Ser Ser Thr
            20                  25                  30

Pro Ala Leu Pro Gly Glu Pro Ala Thr Gly Thr Gly Gly Leu Ile Phe
            35                  40                  45

His Gln Asp Trp Asp Trp Pro Pro Gly Ser Pro Gln Glu Pro Leu Gly
    50                  55                  60

Cys Leu Val Thr Leu Asp Glu Gly Gly Asn Gln Ser Ser Ala Pro Leu
65                  70                  75                  80

Arg Val Ala Gly Ala Leu Ser Gly Tyr Glu Gln Ala Phe Leu Glu Ala
                85                  90                  95

Val Gln Arg Thr His Trp Ser Pro Arg Asp Leu Pro Thr Phe Gly Val
            100                 105                 110

Cys Ser Pro Ala Asp Arg Gln Ala Ala Val Pro Ser Leu Gln Arg Leu
            115                 120                 125

Gln Ala Trp Leu Gly Ala Pro Trp Gly Gln Arg Leu Val Val Leu His
    130                 135                 140

Leu Glu Glu Val Met Trp Glu Pro Thr Pro Ser Leu Arg Phe Gln Glu
145                 150                 155                 160

Pro Pro Ser Gly Gly Ala Asn Pro Leu Glu Pro Ala Leu Leu Val Leu
                165                 170                 175

Tyr Ala Gly Pro Gly Pro Glu Val Thr Val Thr Gly Ala Gly Leu Pro
            180                 185                 190

Gly Ala Gln Ser Leu Cys Pro Ser Pro Asp Thr Arg Tyr Leu Ala Leu
            195                 200                 205

Ala Val Asp His Pro Ala Arg Ala Trp Arg His Pro Gly Leu Ile Leu
    210                 215                 220

Thr Leu Gln Pro Arg Gly Asp Gly Ala Pro Leu Ser Thr Ala Gln Leu
225                 230                 235                 240

Gln Thr Leu Leu Phe Gly Ala Asp Pro Arg Cys Phe Thr Arg Met Thr
                245                 250                 255

Pro Ala Leu Phe Leu Leu Gln Arg Pro Gly Pro Ala Pro Met Pro Ala
            260                 265                 270

His Gly Arg Leu Asp Thr Val Pro Phe Pro Pro Ala Arg Pro Ser Pro
            275                 280                 285

Glu Pro Glu Glu Pro Arg Pro Ser Ala Asp Pro Phe Leu Glu Thr Leu
    290                 295                 300

Thr Arg Leu Val Arg Ala Leu Arg Gly Pro Pro Thr Pro Ala Ser Pro
305                 310                 315                 320

Pro Arg Leu Ala Leu Asp Pro Gly Ala Leu Ala Ser Phe Pro Gln Gly
                325                 330                 335

Leu Val Asn Leu Ser Asp Pro Ala Ala Leu Glu Arg Leu Leu Asp Gly
            340                 345                 350

Glu Glu Pro Leu Leu Leu Leu Pro Thr Ala Ala Ala Gly
            355                 360                 365

Asp Pro Ala Pro Leu Pro Asp Pro Ala Ser Ala Pro Trp Ala Ala Gly
    370                 375                 380

Leu Ala Arg Arg Val Ala Glu Leu Gln Ala Ala Ala Glu Leu
385                 390                 395                 400

Arg Ser Leu Pro Gly Leu Pro Ala Ala Glu Pro Leu Leu Ala Arg
                405                 410                 415

Leu Leu Ala Leu Cys Pro Gly Asp Ala Glu Asp Gln Gly Gly Pro Gly
```

```
                420             425             430
Gly Pro Leu Arg Ala Leu Leu Leu Lys Ala Leu Gln Gly Leu Arg
            435                 440                 445
Ala Glu Trp Arg Gly Arg Glu Arg Ser Gly Pro Gly Arg Ala Gln Arg
            450                 455                 460
Asn Ala Gly Ala Gly Ala Ala Asp Gly Pro Cys Ala Leu Arg Glu Leu
465                 470                 475                 480
Arg Val Asp Leu Arg Ala Glu Arg Ser Val Leu Ile Pro Glu Thr Tyr
                485                 490                 495
Gln Ala Asn Asn Cys Gln Gly Ala Cys Gly Trp Pro Gln Ser Asp Arg
                500                 505                 510
Asn Pro Arg Tyr Gly Asn His Val Val Leu Leu Lys Met Gln Ala
            515                 520                 525
Arg Gly Ala Ala Leu Ala Arg Ala Pro Cys Cys Val Pro Thr Ala Tyr
            530                 535                 540
Ala Gly Lys Leu Leu Ile Ser Leu Ser Glu Glu Arg Ile Ser Ala His
545                 550                 555                 560
His Val Pro Asn Met Val Ala Thr Glu Cys Gly Cys Arg
                565                 570

<210> SEQ ID NO 16
<211> LENGTH: 551
<212> TYPE: PRT
<213> ORGANISM: artificial sequence
<220> FEATURE:
<223> OTHER INFORMATION: polypeptide

<400> SEQUENCE: 16

Gly Thr Pro Gly Glu Glu Val Ser Ser Thr Pro Ala Leu Pro Gly Glu
1               5                   10                  15
Pro Ala Thr Gly Thr Gly Gly Leu Ile Phe His Gln Asp Trp Asp Trp
                20                  25                  30
Pro Pro Gly Ser Pro Gln Glu Pro Leu Gly Cys Leu Val Thr Leu Asp
            35                  40                  45
Glu Gly Gly Asn Gln Ser Ser Ala Pro Leu Arg Val Ala Gly Ala Leu
        50                  55                  60
Ser Gly Tyr Glu Gln Ala Phe Leu Glu Ala Val Gln Arg Thr His Trp
65                  70                  75                  80
Ser Pro Arg Asp Leu Pro Thr Phe Gly Val Cys Ser Pro Ala Asp Arg
                85                  90                  95
Gln Ala Ala Val Pro Ser Leu Gln Arg Leu Gln Ala Trp Leu Gly Ala
                100                 105                 110
Pro Trp Gly Gln Arg Leu Val Val Leu His Leu Glu Glu Val Met Trp
            115                 120                 125
Glu Pro Thr Pro Ser Leu Arg Phe Gln Glu Pro Pro Ser Gly Gly Ala
        130                 135                 140
Asn Pro Leu Glu Pro Ala Leu Leu Val Leu Tyr Ala Gly Pro Gly Pro
145                 150                 155                 160
Glu Val Thr Val Thr Gly Ala Gly Leu Pro Gly Ala Gln Ser Leu Cys
                165                 170                 175
Pro Ser Pro Asp Thr Arg Tyr Leu Ala Leu Ala Val Asp His Pro Ala
                180                 185                 190
Arg Ala Trp Arg His Pro Gly Leu Ile Leu Thr Leu Gln Pro Arg Gly
            195                 200                 205
Asp Gly Ala Pro Leu Ser Thr Ala Gln Leu Gln Thr Leu Leu Phe Gly
```

```
            210                 215                 220
Ala Asp Pro Arg Cys Phe Thr Arg Met Thr Pro Ala Leu Phe Leu Leu
225                 230                 235                 240

Gln Arg Pro Gly Pro Ala Pro Met Pro Ala His Gly Arg Leu Asp Thr
                245                 250                 255

Val Pro Phe Pro Pro Ala Arg Pro Ser Pro Glu Pro Glu Glu Pro Arg
                260                 265                 270

Pro Ser Ala Asp Pro Phe Leu Glu Thr Leu Thr Arg Leu Val Arg Ala
                275                 280                 285

Leu Arg Gly Pro Pro Thr Pro Ala Ser Pro Pro Arg Leu Ala Leu Asp
        290                 295                 300

Pro Gly Ala Leu Ala Ser Phe Pro Gln Gly Leu Val Asn Leu Ser Asp
305                 310                 315                 320

Pro Ala Ala Leu Glu Arg Leu Leu Asp Gly Glu Glu Pro Leu Leu Leu
                325                 330                 335

Leu Leu Pro Pro Thr Ala Ala Ala Gly Asp Pro Ala Pro Leu Pro
                340                 345                 350

Asp Pro Ala Ser Ala Pro Trp Ala Ala Gly Leu Ala Arg Arg Val Ala
                355                 360                 365

Ala Glu Leu Gln Ala Ala Ala Glu Leu Arg Ser Leu Pro Gly Leu
370                 375                 380

Pro Pro Ala Ala Glu Pro Leu Leu Ala Arg Leu Leu Ala Leu Cys Pro
385                 390                 395                 400

Gly Asp Ala Glu Asp Gln Gly Pro Gly Gly Pro Leu Arg Ala Leu
                405                 410                 415

Leu Leu Leu Lys Ala Leu Gln Gly Leu Arg Ala Glu Trp Arg Gly Arg
                420                 425                 430

Glu Arg Ser Gly Pro Gly Arg Ala Gln Arg Asn Ala Gly Ala Gly Ala
                435                 440                 445

Ala Asp Gly Pro Cys Ala Leu Arg Glu Leu Arg Val Asp Leu Arg Ala
450                 455                 460

Glu Arg Ser Val Leu Ile Pro Glu Thr Tyr Gln Ala Asn Asn Cys Gln
465                 470                 475                 480

Gly Ala Cys Gly Trp Pro Gln Ser Asp Arg Asn Pro Arg Tyr Gly Asn
                485                 490                 495

His Val Val Leu Leu Leu Lys Met Gln Ala Arg Gly Ala Ala Leu Ala
                500                 505                 510

Arg Ala Pro Cys Cys Val Pro Thr Ala Tyr Ala Gly Lys Leu Leu Ile
                515                 520                 525

Ser Leu Ser Glu Glu Arg Ile Ser Ala His His Val Pro Asn Met Val
530                 535                 540

Ala Thr Glu Cys Gly Cys Arg
545                 550

<210> SEQ ID NO 17
<211> LENGTH: 464
<212> TYPE: PRT
<213> ORGANISM: artificial sequence
<220> FEATURE:
<223> OTHER INFORMATION: polypeptide

<400> SEQUENCE: 17

Met Arg Ala Pro Ser Leu Ser Trp Leu Ala Leu Val Leu Ser Ala Val
1               5                   10                  15

Gly Ala Leu Leu Arg Ala Gly Thr Pro Gly Glu Glu Val Ser Ser Thr
```

```
                20                  25                  30
Pro Ala Leu Pro Gly Glu Pro Ala Thr Gly Thr Gly Gly Leu Ile Phe
            35                  40                  45
His Gln Asp Trp Asp Trp Pro Pro Gly Ser Pro Gln Glu Pro Leu Gly
        50                  55                  60
Cys Leu Val Thr Leu Asp Glu Gly Gly Asn Gln Ser Ser Ala Pro Leu
65                  70                  75                  80
Arg Val Ala Gly Ala Leu Ser Gly Tyr Glu Gln Ala Phe Leu Glu Ala
                85                  90                  95
Val Gln Arg Thr His Trp Ser Pro Arg Asp Leu Pro Thr Phe Gly Val
            100                 105                 110
Cys Ser Pro Ala Asp Arg Gln Ala Val Pro Ser Leu Gln Arg Leu
        115                 120                 125
Gln Ala Trp Leu Gly Ala Pro Trp Gly Gln Arg Leu Val Val Leu His
            130                 135                 140
Leu Glu Glu Val Met Trp Glu Pro Thr Pro Ser Leu Arg Phe Gln Glu
145                 150                 155                 160
Pro Pro Ser Gly Gly Ala Asn Pro Leu Glu Pro Ala Leu Leu Val Leu
                165                 170                 175
Tyr Ala Gly Pro Gly Pro Glu Val Thr Val Thr Gly Ala Gly Leu Pro
            180                 185                 190
Gly Ala Gln Ser Leu Cys Pro Ser Pro Asp Thr Arg Tyr Leu Ala Leu
            195                 200                 205
Ala Val Asp His Pro Ala Arg Ala Trp Arg His Pro Gly Leu Ile Leu
        210                 215                 220
Thr Leu Gln Pro Arg Gly Asp Gly Ala Pro Leu Ser Thr Ala Gln Leu
225                 230                 235                 240
Gln Thr Leu Leu Phe Gly Ala Asp Pro Arg Cys Phe Thr Arg Met Thr
                245                 250                 255
Pro Ala Leu Phe Leu Leu Gln Arg Pro Gly Pro Ala Pro Met Pro Ala
            260                 265                 270
His Gly Arg Leu Asp Thr Val Pro Phe Pro Pro Ala Arg Pro Ser Pro
        275                 280                 285
Glu Pro Glu Glu Pro Arg Pro Ser Ala Asp Pro Phe Leu Glu Thr Leu
    290                 295                 300
Thr Arg Leu Val Arg Ala Leu Arg Gly Pro Pro Thr Pro Ala Ser Pro
305                 310                 315                 320
Pro Arg Leu Ala Leu Asp Pro Gly Ala Leu Ala Ser Phe Pro Gln Gly
                325                 330                 335
Leu Val Asn Leu Ser Asp Pro Ala Ala Leu Glu Arg Leu Leu Asp Gly
            340                 345                 350
Glu Glu Pro Leu Leu Leu Leu Pro Pro Thr Ala Ala Ala Ala Gly
        355                 360                 365
Asp Pro Ala Pro Leu Pro Asp Pro Ala Ser Ala Pro Trp Ala Ala Gly
    370                 375                 380
Leu Ala Arg Arg Val Ala Ala Glu Leu Gln Ala Ala Ala Glu Leu
385                 390                 395                 400
Arg Ser Leu Pro Gly Leu Pro Ala Ala Glu Pro Leu Leu Ala Arg
                405                 410                 415
Leu Leu Ala Leu Cys Pro Gly Asp Ala Glu Asp Gln Gly Gly Pro Gly
            420                 425                 430
Gly Pro Leu Arg Ala Leu Leu Leu Lys Ala Leu Gln Gly Leu Arg
        435                 440                 445
```

```
Ala Glu Trp Arg Gly Arg Glu Arg Ser Gly Pro Gly Arg Ala Gln Arg
    450                 455                 460
```

<210> SEQ ID NO 18
<211> LENGTH: 442
<212> TYPE: PRT
<213> ORGANISM: artificial sequence
<220> FEATURE:
<223> OTHER INFORMATION: polypeptide

<400> SEQUENCE: 18

```
Gly Thr Pro Gly Glu Val Ser Ser Thr Pro Ala Leu Pro Gly Glu
1               5                   10                  15

Pro Ala Thr Gly Thr Gly Leu Ile Phe His Gln Asp Trp Asp Trp
                20                  25                  30

Pro Pro Gly Ser Pro Gln Glu Pro Leu Gly Cys Leu Val Thr Leu Asp
            35                  40                  45

Glu Gly Gly Asn Gln Ser Ser Ala Pro Leu Arg Val Ala Gly Ala Leu
50                  55                  60

Ser Gly Tyr Glu Gln Ala Phe Leu Glu Ala Val Gln Arg Thr His Trp
65                  70                  75                  80

Ser Pro Arg Asp Leu Pro Thr Phe Gly Val Cys Ser Pro Ala Asp Arg
                85                  90                  95

Gln Ala Ala Val Pro Ser Leu Gln Arg Leu Gln Ala Trp Leu Gly Ala
            100                 105                 110

Pro Trp Gly Gln Arg Leu Val Val Leu His Leu Glu Glu Val Met Trp
        115                 120                 125

Glu Pro Thr Pro Ser Leu Arg Phe Gln Glu Pro Pro Ser Gly Gly Ala
130                 135                 140

Asn Pro Leu Glu Pro Ala Leu Leu Val Leu Tyr Ala Gly Pro Gly Pro
145                 150                 155                 160

Glu Val Thr Val Thr Gly Ala Gly Leu Pro Gly Ala Gln Ser Leu Cys
                165                 170                 175

Pro Ser Pro Asp Thr Arg Tyr Leu Ala Leu Ala Val Asp His Pro Ala
            180                 185                 190

Arg Ala Trp Arg His Pro Gly Leu Ile Leu Thr Leu Gln Pro Arg Gly
        195                 200                 205

Asp Gly Ala Pro Leu Ser Thr Ala Gln Leu Gln Thr Leu Leu Phe Gly
210                 215                 220

Ala Asp Pro Arg Cys Phe Thr Arg Met Thr Pro Ala Leu Phe Leu Leu
225                 230                 235                 240

Gln Arg Pro Gly Pro Ala Pro Met Pro Ala His Gly Arg Leu Asp Thr
                245                 250                 255

Val Pro Phe Pro Pro Ala Arg Pro Ser Pro Glu Pro Glu Glu Pro Arg
            260                 265                 270

Pro Ser Ala Asp Pro Phe Leu Glu Thr Leu Thr Arg Leu Val Arg Ala
        275                 280                 285

Leu Arg Gly Pro Pro Thr Pro Ala Ser Pro Pro Arg Leu Ala Leu Asp
290                 295                 300

Pro Gly Ala Leu Ala Ser Phe Pro Gln Gly Leu Val Asn Leu Ser Asp
305                 310                 315                 320

Pro Ala Ala Leu Glu Arg Leu Leu Asp Gly Glu Glu Pro Leu Leu Leu
                325                 330                 335

Leu Leu Pro Pro Thr Ala Ala Ala Gly Asp Pro Ala Pro Leu Pro
            340                 345                 350
```

Asp Pro Ala Ser Ala Pro Trp Ala Gly Leu Ala Arg Arg Val Ala
        355                 360                 365

Ala Glu Leu Gln Ala Ala Ala Glu Leu Arg Ser Leu Pro Gly Leu
    370                 375                 380

Pro Pro Ala Ala Glu Pro Leu Leu Ala Arg Leu Leu Ala Leu Cys Pro
385                 390                 395                 400

Gly Asp Ala Glu Asp Gln Gly Gly Pro Gly Pro Leu Arg Ala Leu
            405                 410                 415

Leu Leu Leu Lys Ala Leu Gln Gly Leu Arg Ala Glu Trp Arg Gly Arg
            420                 425                 430

Glu Arg Ser Gly Pro Gly Arg Ala Gln Arg
        435                 440

<210> SEQ ID NO 19
<211> LENGTH: 265
<212> TYPE: PRT
<213> ORGANISM: artificial sequence
<220> FEATURE:
<223> OTHER INFORMATION: polypeptide

<400> SEQUENCE: 19

Met Arg Ala Pro Ser Leu Ser Trp Leu Ala Leu Val Leu Ser Ala Val
1               5                   10                  15

Gly Ala Leu Leu Arg Ala Gly Thr Pro Gly Glu Glu Val Ser Ser Thr
            20                  25                  30

Pro Ala Leu Pro Gly Glu Pro Ala Thr Gly Thr Gly Gly Leu Ile Phe
        35                  40                  45

His Gln Asp Trp Asp Trp Pro Pro Gly Ser Pro Gln Glu Pro Leu Gly
    50                  55                  60

Cys Leu Val Thr Leu Asp Glu Gly Gly Asn Gln Ser Ser Ala Pro Leu
65                  70                  75                  80

Arg Val Ala Gly Ala Leu Ser Gly Tyr Glu Gln Ala Phe Leu Glu Ala
                85                  90                  95

Val Gln Arg Thr His Trp Ser Pro Arg Asp Leu Pro Thr Phe Gly Val
            100                 105                 110

Cys Ser Pro Ala Asp Arg Gln Ala Ala Val Pro Ser Leu Gln Arg Leu
        115                 120                 125

Gln Ala Trp Leu Gly Ala Pro Trp Gly Gln Arg Leu Val Val Leu His
    130                 135                 140

Leu Glu Glu Val Met Trp Glu Pro Thr Pro Ser Leu Arg Phe Gln Glu
145                 150                 155                 160

Pro Pro Ser Gly Gly Ala Asn Pro Leu Glu Pro Ala Leu Leu Val Leu
                165                 170                 175

Tyr Ala Gly Pro Gly Pro Glu Val Thr Val Thr Gly Ala Gly Leu Pro
            180                 185                 190

Gly Ala Gln Ser Leu Cys Pro Ser Pro Asp Thr Arg Tyr Leu Ala Leu
        195                 200                 205

Ala Val Asp His Pro Ala Arg Ala Trp Arg His Pro Gly Leu Ile Leu
    210                 215                 220

Thr Leu Gln Pro Arg Gly Asp Gly Ala Pro Leu Ser Thr Ala Gln Leu
225                 230                 235                 240

Gln Thr Leu Leu Phe Gly Ala Asp Pro Arg Cys Phe Thr Arg Met Thr
                245                 250                 255

Pro Ala Leu Phe Leu Leu Gln Arg Pro
            260                 265

<210> SEQ ID NO 20
<211> LENGTH: 243
<212> TYPE: PRT
<213> ORGANISM: artificial sequence
<220> FEATURE:
<223> OTHER INFORMATION: polypeptide

<400> SEQUENCE: 20

Gly Thr Pro Gly Glu Val Ser Ser Thr Pro Ala Leu Pro Gly Glu
1               5                   10                  15

Pro Ala Thr Gly Thr Gly Gly Leu Ile Phe His Gln Asp Trp Asp Trp
            20                  25                  30

Pro Pro Gly Ser Pro Gln Glu Pro Leu Gly Cys Leu Val Thr Leu Asp
        35                  40                  45

Glu Gly Gly Asn Gln Ser Ser Ala Pro Leu Arg Val Ala Gly Ala Leu
    50                  55                  60

Ser Gly Tyr Glu Gln Ala Phe Leu Glu Ala Val Gln Arg Thr His Trp
65                  70                  75                  80

Ser Pro Arg Asp Leu Pro Thr Phe Gly Val Cys Ser Pro Ala Asp Arg
                85                  90                  95

Gln Ala Ala Val Pro Ser Leu Gln Arg Leu Gln Ala Trp Leu Gly Ala
            100                 105                 110

Pro Trp Gly Gln Arg Leu Val Val Leu His Leu Glu Glu Val Met Trp
        115                 120                 125

Glu Pro Thr Pro Ser Leu Arg Phe Gln Glu Pro Pro Ser Gly Gly Ala
    130                 135                 140

Asn Pro Leu Glu Pro Ala Leu Leu Val Leu Tyr Ala Gly Pro Gly Pro
145                 150                 155                 160

Glu Val Thr Val Thr Gly Ala Gly Leu Pro Gly Ala Gln Ser Leu Cys
                165                 170                 175

Pro Ser Pro Asp Thr Arg Tyr Leu Ala Leu Ala Val Asp His Pro Ala
            180                 185                 190

Arg Ala Trp Arg His Pro Gly Leu Ile Leu Thr Leu Gln Pro Arg Gly
        195                 200                 205

Asp Gly Ala Pro Leu Ser Thr Ala Gln Leu Gln Thr Leu Leu Phe Gly
    210                 215                 220

Ala Asp Pro Arg Cys Phe Thr Arg Met Thr Pro Ala Leu Phe Leu Leu
225                 230                 235                 240

Gln Arg Pro

<210> SEQ ID NO 21
<211> LENGTH: 166
<212> TYPE: PRT
<213> ORGANISM: artificial sequence
<220> FEATURE:
<223> OTHER INFORMATION: polypeptide

<400> SEQUENCE: 21

Met Arg Ala Pro Ser Leu Ser Trp Leu Ala Leu Val Leu Ser Ala Val
1               5                   10                  15

Gly Ala Leu Leu Arg Ala Gly Thr Pro Gly Glu Glu Val Ser Ser Thr
            20                  25                  30

Pro Ala Leu Pro Gly Glu Pro Ala Thr Gly Thr Gly Gly Leu Ile Phe
        35                  40                  45

His Gln Asp Trp Asp Trp Pro Pro Gly Ser Pro Gln Glu Pro Leu Gly
    50                  55                  60

Cys Leu Val Thr Leu Asp Glu Gly Gly Asn Gln Ser Ala Pro Leu
 65                  70                  75                  80

Arg Val Ala Gly Ala Leu Ser Gly Tyr Glu Gln Ala Phe Leu Glu Ala
                 85                  90                  95

Val Gln Arg Thr His Trp Ser Pro Arg Asp Leu Pro Thr Phe Gly Val
            100                 105                 110

Cys Ser Pro Ala Asp Arg Gln Ala Ala Val Pro Ser Leu Gln Arg Leu
            115                 120                 125

Gln Ala Trp Leu Gly Ala Pro Trp Gly Gln Arg Leu Val Leu His
    130                 135                 140

Leu Glu Glu Val Met Trp Glu Pro Thr Pro Ser Leu Arg Phe Gln Glu
145                 150                 155                 160

Pro Pro Ser Gly Gly Ala
            165

<210> SEQ ID NO 22
<211> LENGTH: 144
<212> TYPE: PRT
<213> ORGANISM: artificial sequence
<220> FEATURE:
<223> OTHER INFORMATION: polypeptide

<400> SEQUENCE: 22

Gly Thr Pro Gly Glu Glu Val Ser Ser Thr Pro Ala Leu Pro Gly Glu
1               5                   10                  15

Pro Ala Thr Gly Thr Gly Gly Leu Ile Phe His Gln Asp Trp Asp Trp
            20                  25                  30

Pro Pro Gly Ser Pro Gln Glu Pro Leu Gly Cys Leu Val Thr Leu Asp
        35                  40                  45

Glu Gly Gly Asn Gln Ser Ser Ala Pro Leu Arg Val Ala Gly Ala Leu
    50                  55                  60

Ser Gly Tyr Glu Gln Ala Phe Leu Glu Ala Val Gln Arg Thr His Trp
65                  70                  75                  80

Ser Pro Arg Asp Leu Pro Thr Phe Gly Val Cys Ser Pro Ala Asp Arg
                85                  90                  95

Gln Ala Ala Val Pro Ser Leu Gln Arg Leu Gln Ala Trp Leu Gly Ala
            100                 105                 110

Pro Trp Gly Gln Arg Leu Val Leu His Leu Glu Glu Val Met Trp
        115                 120                 125

Glu Pro Thr Pro Ser Leu Arg Phe Gln Glu Pro Pro Ser Gly Gly Ala
    130                 135                 140

<210> SEQ ID NO 23
<211> LENGTH: 99
<212> TYPE: PRT
<213> ORGANISM: artificial sequence
<220> FEATURE:
<223> OTHER INFORMATION: polypeptide

<400> SEQUENCE: 23

Ser Pro Leu Glu Leu Ala Leu Leu Val Leu Tyr Pro Gly Pro Gly Pro
1               5                   10                  15

Glu Val Ala Val Thr Gly Ala Gly Leu Pro Gly Thr Gln Asn Leu Cys
            20                  25                  30

Arg Ser Arg Asn Thr Arg Tyr Leu Val Leu Ala Leu Asp His Pro Val
        35                  40                  45

Gly Ala Trp His Ser Pro Arg Val Thr Leu Thr Val His Ala Arg Gly

```
                50                  55                  60
Asp Gly Ala Pro Leu Ser Thr Pro Gln Leu Gln Glu Leu Leu Phe Gly
 65                  70                  75                  80

Pro Asp Ala Arg Cys Phe Thr Arg Met Thr Pro Ala Leu Leu Val Leu
                 85                  90                  95

Arg Leu Pro

<210> SEQ ID NO 24
<211> LENGTH: 572
<212> TYPE: PRT
<213> ORGANISM: Canis familiaris

<400> SEQUENCE: 24

Met Gly Ala Leu Ala Leu Trp Pro Leu Ala Leu Ala Leu Ser Gly Met
 1               5                  10                  15

Gly Pro Leu Leu Gly Ala Glu Ala Pro Gly Gly Glu Val Ser Gly Thr
                20                  25                  30

Pro Ala Ser Pro Gly Glu Pro Ala Thr Gly Thr Gly Gly Leu Leu Phe
             35                  40                  45

Gln Pro Asp Trp Asp Trp Pro Ser Ala Pro Gln Asp Pro Leu Cys
         50                  55                  60

Leu Val Thr Leu Asp Lys Gly Gly Asn Gly Ser Ser Pro Pro Leu Arg
 65                  70                  75                  80

Val Ala Gly Ala Leu Arg Gly Tyr Glu His Thr Phe Leu Glu Ala Val
                 85                  90                  95

Arg Arg Ala Arg Trp Gly Pro His Asp Leu Ala Thr Phe Gly Ala Cys
            100                 105                 110

Ala Ala Ser Asp Gly Arg Thr Thr Gln Leu Ser Leu Arg Gln Leu Gln
        115                 120                 125

Ala Trp Leu Gly Ala Pro Gly Gly Arg Arg Leu Val Val Leu His Leu
130                 135                 140

Glu Glu Val Thr Trp Glu Pro Ala Leu Ser Leu Lys Phe Gln Glu Pro
145                 150                 155                 160

Pro Pro Gly Gly Ala Ser Pro Leu Glu Leu Ala Leu Leu Val Leu Tyr
                165                 170                 175

Pro Gly Pro Gly Pro Glu Val Ala Val Thr Gly Ala Gly Leu Pro Gly
            180                 185                 190

Thr Gln Asn Leu Cys Arg Ser Arg Asn Thr Arg Tyr Leu Val Leu Ala
        195                 200                 205

Leu Asp His Pro Val Gly Ala Trp His Ser Pro Arg Val Thr Leu Thr
    210                 215                 220

Val His Ala Arg Gly Asp Gly Ala Pro Leu Ser Thr Pro Gln Leu Gln
225                 230                 235                 240

Glu Leu Leu Phe Gly Pro Asp Ala Arg Cys Phe Thr Arg Met Thr Pro
                245                 250                 255

Ala Leu Leu Val Leu Arg Leu Pro Gly Pro Thr Ala Val Pro Ala Arg
            260                 265                 270

Gly Leu Leu Asp Leu Val Pro Phe Pro Pro Arg Pro Ser Arg Glu
        275                 280                 285

Pro Ala Glu Pro Pro Ser Ala Asp Pro Phe Leu Glu Thr Leu Thr
    290                 295                 300

Arg Leu Val Arg Ala Leu Arg Gly Pro Pro Thr Pro Ala Ser Pro Pro
305                 310                 315                 320

Arg Leu Ala Leu Asp Pro Gly Ala Leu Ala Gly Phe Pro Gln Gly Leu
```

```
                325                 330                 335
Leu Asn Leu Ser Asp Pro Ala Thr Gln Glu Arg Leu Leu Gly Gly Glu
            340                 345                 350

Glu Pro Leu Leu Leu Leu Pro Pro Thr Ala Ala Gly Pro
        355                 360                 365

Pro Ala Pro Pro Arg Pro Ala Ser Ala Pro Trp Ala Ala Gly Leu
370                 375                 380

Ala Leu Arg Val Ala Ala Glu Leu Arg Ala Ala Ala Glu Leu Arg
385                 390                 395                 400

Gly Leu Pro Gly Leu Pro Pro Ala Ala Pro Leu Leu Glu Arg Leu
                405                 410                 415

Leu Ala Leu Cys Pro Gly Gly Ser Gly Ser Gly Ser Gly Asp
                420                 425                 430

Pro Leu Arg Ala Leu Leu Leu Lys Ala Leu Gln Gly Leu Arg Ala
                435                 440                 445

Glu Trp Arg Gly Arg Glu Arg Gly Pro Arg Ala Gln Arg Ser
450                 455                 460

Ala Gly Ala Gly Ala Ala Asp Gly Pro Cys Ala Leu Arg Glu Leu Ser
465                 470                 475                 480

Val Asp Leu Arg Ala Glu Arg Ser Val Leu Ile Pro Glu Thr Tyr Gln
                485                 490                 495

Ala Asn Asn Cys Gln Gly Ala Cys Gly Trp Pro Gln Ser Asp Arg Asn
                500                 505                 510

Pro Arg Tyr Gly Asn His Val Val Leu Leu Leu Lys Met Gln Ala Arg
            515                 520                 525

Gly Ala Ala Leu Ala Arg Pro Pro Cys Cys Val Pro Thr Ala Tyr Gly
        530                 535                 540

Gly Lys Leu Leu Ile Ser Leu Ser Glu Glu Arg Ile Ser Ala His His
545                 550                 555                 560

Val Pro Asn Met Val Ala Thr Glu Cys Gly Cys Arg
                565                 570

<210> SEQ ID NO 25
<211> LENGTH: 551
<212> TYPE: PRT
<213> ORGANISM: artificial sequence
<220> FEATURE:
<223> OTHER INFORMATION: polypeptide

<400> SEQUENCE: 25

Ala Glu Ala Pro Gly Gly Glu Val Ser Gly Thr Pro Ala Ser Pro Gly
1               5                   10                  15

Glu Pro Ala Thr Gly Thr Gly Gly Leu Leu Phe Gln Pro Asp Trp Asp
                20                  25                  30

Trp Pro Pro Ser Ala Pro Gln Asp Pro Leu Cys Leu Val Thr Leu Asp
            35                  40                  45

Lys Gly Gly Asn Gly Ser Ser Pro Pro Leu Arg Val Ala Gly Ala Leu
        50                  55                  60

Arg Gly Tyr Glu His Thr Phe Leu Glu Ala Val Arg Arg Ala Arg Trp
65                  70                  75                  80

Gly Pro His Asp Leu Ala Thr Phe Gly Ala Cys Ala Ala Ser Asp Gly
                85                  90                  95

Arg Thr Thr Gln Leu Ser Leu Arg Gln Leu Gln Ala Trp Leu Gly Ala
                100                 105                 110

Pro Gly Gly Arg Arg Leu Val Val Leu His Leu Glu Glu Val Thr Trp
```

```
            115                 120                 125
Glu Pro Ala Leu Ser Leu Lys Phe Gln Glu Pro Pro Gly Gly Ala
        130                 135                 140

Ser Pro Leu Glu Leu Ala Leu Leu Val Leu Tyr Pro Gly Pro Gly Pro
145                 150                 155                 160

Glu Val Ala Val Thr Gly Ala Gly Leu Pro Gly Thr Gln Asn Leu Cys
                165                 170                 175

Arg Ser Arg Asn Thr Arg Tyr Leu Val Leu Ala Leu Asp His Pro Val
                180                 185                 190

Gly Ala Trp His Ser Pro Arg Val Thr Leu Thr Val His Ala Arg Gly
                195                 200                 205

Asp Gly Ala Pro Leu Ser Thr Pro Gln Leu Gln Glu Leu Leu Phe Gly
        210                 215                 220

Pro Asp Ala Arg Cys Phe Thr Arg Met Thr Pro Ala Leu Leu Val Leu
225                 230                 235                 240

Arg Leu Pro Gly Pro Thr Ala Val Pro Ala Arg Gly Leu Leu Asp Leu
                245                 250                 255

Val Pro Phe Pro Pro Arg Pro Ser Arg Glu Pro Ala Glu Pro Pro
        260                 265                 270

Pro Ser Ala Asp Pro Phe Leu Glu Thr Leu Thr Arg Leu Val Arg Ala
        275                 280                 285

Leu Arg Gly Pro Pro Thr Pro Ala Ser Pro Pro Arg Leu Ala Leu Asp
        290                 295                 300

Pro Gly Ala Leu Ala Gly Phe Pro Gln Gly Leu Leu Asn Leu Ser Asp
305                 310                 315                 320

Pro Ala Thr Gln Glu Arg Leu Leu Gly Gly Glu Pro Leu Leu Leu
                325                 330                 335

Leu Leu Pro Pro Pro Thr Ala Ala Gly Pro Ala Pro Pro
                340                 345                 350

Arg Pro Ala Ser Ala Pro Trp Ala Ala Gly Leu Ala Leu Arg Val Ala
                355                 360                 365

Ala Glu Leu Arg Ala Ala Ala Glu Leu Arg Gly Leu Pro Gly Leu
        370                 375                 380

Pro Pro Ala Ala Ala Pro Leu Leu Glu Arg Leu Leu Ala Leu Cys Pro
385                 390                 395                 400

Gly Gly Ser Gly Gly Ser Gly Gly Ser Gly Asp Pro Leu Arg Ala Leu
                405                 410                 415

Leu Leu Leu Lys Ala Leu Gln Gly Leu Arg Ala Glu Trp Arg Gly Arg
                420                 425                 430

Glu Arg Gly Gly Pro Pro Arg Ala Gln Arg Ser Ala Gly Ala Gly Ala
        435                 440                 445

Ala Asp Gly Pro Cys Ala Leu Arg Glu Leu Ser Val Asp Leu Arg Ala
        450                 455                 460

Glu Arg Ser Val Leu Ile Pro Glu Thr Tyr Gln Ala Asn Asn Cys Gln
465                 470                 475                 480

Gly Ala Cys Gly Trp Pro Gln Ser Asp Arg Asn Pro Arg Tyr Gly Asn
                485                 490                 495

His Val Val Leu Leu Leu Lys Met Gln Ala Arg Gly Ala Ala Leu Ala
                500                 505                 510

Arg Pro Pro Cys Cys Val Pro Thr Ala Tyr Gly Gly Lys Leu Leu Ile
                515                 520                 525

Ser Leu Ser Glu Glu Arg Ile Ser Ala His His Val Pro Asn Met Val
        530                 535                 540
```

```
Ala Thr Glu Cys Gly Cys Arg
545                 550

<210> SEQ ID NO 26
<211> LENGTH: 463
<212> TYPE: PRT
<213> ORGANISM: artificial sequence
<220> FEATURE:
<223> OTHER INFORMATION: polypeptide

<400> SEQUENCE: 26

Met Gly Ala Leu Ala Leu Trp Pro Leu Ala Leu Ala Leu Ser Gly Met
1               5                   10                  15

Gly Pro Leu Leu Gly Ala Glu Ala Pro Gly Gly Glu Val Ser Gly Thr
            20                  25                  30

Pro Ala Ser Pro Gly Glu Pro Ala Thr Gly Thr Gly Gly Leu Leu Phe
        35                  40                  45

Gln Pro Asp Trp Asp Trp Pro Ser Ala Pro Gln Asp Pro Leu Cys
50                  55                  60

Leu Val Thr Leu Asp Lys Gly Asn Gly Ser Ser Pro Pro Leu Arg
65                  70                  75                  80

Val Ala Gly Ala Leu Arg Gly Tyr Glu His Thr Phe Leu Glu Ala Val
                85                  90                  95

Arg Arg Ala Arg Trp Gly Pro His Asp Leu Ala Thr Phe Gly Ala Cys
            100                 105                 110

Ala Ala Ser Asp Gly Arg Thr Thr Gln Leu Ser Leu Arg Gln Leu Gln
        115                 120                 125

Ala Trp Leu Gly Ala Pro Gly Gly Arg Arg Leu Val Val Leu His Leu
130                 135                 140

Glu Glu Val Thr Trp Glu Pro Ala Leu Ser Leu Lys Phe Gln Glu Pro
145                 150                 155                 160

Pro Pro Gly Gly Ala Ser Pro Leu Glu Leu Ala Leu Leu Val Leu Tyr
                165                 170                 175

Pro Gly Pro Gly Pro Glu Val Ala Val Thr Gly Ala Gly Leu Pro Gly
            180                 185                 190

Thr Gln Asn Leu Cys Arg Ser Arg Asn Thr Arg Tyr Leu Val Leu Ala
        195                 200                 205

Leu Asp His Pro Val Gly Ala Trp His Ser Pro Arg Val Thr Leu Thr
210                 215                 220

Val His Ala Arg Gly Asp Gly Ala Pro Leu Ser Thr Pro Gln Leu Gln
225                 230                 235                 240

Glu Leu Leu Phe Gly Pro Asp Ala Arg Cys Phe Thr Arg Met Thr Pro
                245                 250                 255

Ala Leu Leu Val Leu Arg Leu Pro Gly Pro Thr Ala Val Pro Ala Arg
            260                 265                 270

Gly Leu Leu Asp Leu Val Pro Phe Pro Pro Arg Pro Ser Arg Glu
        275                 280                 285

Pro Ala Glu Pro Pro Pro Ser Ala Asp Pro Phe Leu Glu Thr Leu Thr
290                 295                 300

Arg Leu Val Arg Ala Leu Arg Gly Pro Thr Pro Ala Ser Pro Pro
305                 310                 315                 320

Arg Leu Ala Leu Asp Pro Gly Ala Leu Ala Gly Phe Pro Gln Gly Leu
                325                 330                 335

Leu Asn Leu Ser Asp Pro Ala Thr Gln Glu Arg Leu Leu Gly Gly Glu
            340                 345                 350
```

Glu Pro Leu Leu Leu Leu Pro Pro Thr Ala Ala Ala Gly Pro
            355                 360                 365

Pro Ala Pro Pro Arg Pro Ala Ser Ala Pro Trp Ala Ala Gly Leu
    370                 375                 380

Ala Leu Arg Val Ala Ala Glu Leu Arg Ala Ala Ala Glu Leu Arg
385                 390                 395                 400

Gly Leu Pro Gly Leu Pro Pro Ala Ala Ala Pro Leu Leu Glu Arg Leu
                405                 410                 415

Leu Ala Leu Cys Pro Gly Gly Ser Gly Ser Gly Gly Ser Gly Asp
                420                 425                 430

Pro Leu Arg Ala Leu Leu Leu Lys Ala Leu Gln Gly Leu Arg Ala
            435                 440                 445

Glu Trp Arg Gly Arg Glu Arg Gly Gly Pro Arg Ala Gln Arg
            450                 455                 460

<210> SEQ ID NO 27
<211> LENGTH: 442
<212> TYPE: PRT
<213> ORGANISM: artificial sequence
<220> FEATURE:
<223> OTHER INFORMATION: polypeptide

<400> SEQUENCE: 27

Ala Glu Ala Pro Gly Gly Glu Val Ser Gly Thr Pro Ala Ser Pro Gly
1               5                   10                  15

Glu Pro Ala Thr Gly Thr Gly Gly Leu Leu Phe Gln Pro Asp Trp Asp
                20                  25                  30

Trp Pro Pro Ser Ala Pro Gln Asp Pro Leu Cys Leu Val Thr Leu Asp
            35                  40                  45

Lys Gly Gly Asn Gly Ser Ser Pro Pro Leu Arg Val Ala Gly Ala Leu
        50                  55                  60

Arg Gly Tyr Glu His Thr Phe Leu Glu Ala Val Arg Arg Ala Arg Trp
65                  70                  75                  80

Gly Pro His Asp Leu Ala Thr Phe Gly Ala Cys Ala Ala Ser Asp Gly
                85                  90                  95

Arg Thr Thr Gln Leu Ser Leu Arg Gln Leu Gln Ala Trp Leu Gly Ala
                100                 105                 110

Pro Gly Gly Arg Arg Leu Val Val Leu His Leu Glu Glu Val Thr Trp
            115                 120                 125

Glu Pro Ala Leu Ser Leu Lys Phe Gln Glu Pro Pro Gly Gly Ala
130                 135                 140

Ser Pro Leu Glu Leu Ala Leu Leu Val Leu Tyr Pro Gly Pro Gly Pro
145                 150                 155                 160

Glu Val Ala Val Thr Gly Ala Gly Leu Pro Gly Thr Gln Asn Leu Cys
                165                 170                 175

Arg Ser Arg Asn Thr Arg Tyr Leu Val Leu Ala Leu Asp His Pro Val
                180                 185                 190

Gly Ala Trp His Ser Pro Arg Val Thr Leu Thr Val His Ala Arg Gly
            195                 200                 205

Asp Gly Ala Pro Leu Ser Thr Pro Gln Leu Gln Glu Leu Leu Phe Gly
        210                 215                 220

Pro Asp Ala Arg Cys Phe Thr Arg Met Thr Pro Ala Leu Leu Val Leu
225                 230                 235                 240

Arg Leu Pro Gly Pro Thr Ala Val Pro Ala Arg Gly Leu Leu Asp Leu
                245                 250                 255

Val Pro Phe Pro Pro Arg Pro Ser Arg Glu Pro Ala Glu Pro Pro
            260                 265                 270

Pro Ser Ala Asp Pro Phe Leu Glu Thr Leu Thr Arg Leu Val Arg Ala
        275                 280                 285

Leu Arg Gly Pro Pro Thr Pro Ala Ser Pro Pro Arg Leu Ala Leu Asp
    290                 295                 300

Pro Gly Ala Leu Ala Gly Phe Pro Gln Gly Leu Leu Asn Leu Ser Asp
305                 310                 315                 320

Pro Ala Thr Gln Glu Arg Leu Leu Gly Glu Pro Leu Leu Leu
            325                 330                 335

Leu Leu Pro Pro Pro Thr Ala Ala Gly Pro Ala Pro Pro
            340                 345                 350

Arg Pro Ala Ser Ala Pro Trp Ala Ala Gly Leu Ala Leu Arg Val Ala
            355                 360                 365

Ala Glu Leu Arg Ala Ala Ala Glu Leu Arg Gly Leu Pro Gly Leu
        370                 375                 380

Pro Pro Ala Ala Ala Pro Leu Leu Glu Arg Leu Leu Ala Leu Cys Pro
385                 390                 395                 400

Gly Gly Ser Gly Gly Ser Gly Gly Ser Gly Asp Pro Leu Arg Ala Leu
            405                 410                 415

Leu Leu Leu Lys Ala Leu Gln Gly Leu Arg Ala Glu Trp Arg Gly Arg
            420                 425                 430

Glu Arg Gly Gly Pro Pro Arg Ala Gln Arg
            435                 440

<210> SEQ ID NO 28
<211> LENGTH: 264
<212> TYPE: PRT
<213> ORGANISM: artificial sequence
<220> FEATURE:
<223> OTHER INFORMATION: polypeptide

<400> SEQUENCE: 28

Met Gly Ala Leu Ala Leu Trp Pro Leu Ala Leu Ala Leu Ser Gly Met
1               5                   10                  15

Gly Pro Leu Leu Gly Ala Glu Ala Pro Gly Gly Glu Val Ser Gly Thr
            20                  25                  30

Pro Ala Ser Pro Gly Glu Pro Ala Thr Gly Thr Gly Gly Leu Leu Phe
        35                  40                  45

Gln Pro Asp Trp Asp Trp Pro Ser Ala Pro Gln Asp Pro Leu Cys
    50                  55                  60

Leu Val Thr Leu Asp Lys Gly Gly Asn Gly Ser Ser Pro Pro Leu Arg
65                  70                  75                  80

Val Ala Gly Ala Leu Arg Gly Tyr Glu His Thr Phe Leu Glu Ala Val
                85                  90                  95

Arg Arg Ala Arg Trp Gly Pro His Asp Leu Ala Thr Phe Gly Ala Cys
            100                 105                 110

Ala Ala Ser Asp Gly Arg Thr Thr Gln Leu Ser Leu Arg Gln Leu Gln
        115                 120                 125

Ala Trp Leu Gly Ala Pro Gly Arg Arg Leu Val Val Leu His Leu
    130                 135                 140

Glu Glu Val Thr Trp Glu Pro Ala Leu Ser Leu Lys Phe Gln Glu Pro
145                 150                 155                 160

Pro Pro Gly Gly Ala Ser Pro Leu Glu Leu Ala Leu Leu Val Leu Tyr
                165                 170                 175

```
Pro Gly Pro Gly Pro Glu Val Ala Val Thr Gly Ala Gly Leu Pro Gly
            180                 185                 190

Thr Gln Asn Leu Cys Arg Ser Arg Asn Thr Arg Tyr Leu Val Leu Ala
        195                 200                 205

Leu Asp His Pro Val Gly Ala Trp His Ser Pro Arg Val Thr Leu Thr
210                 215                 220

Val His Ala Arg Gly Asp Gly Ala Pro Leu Ser Thr Pro Gln Leu Gln
225                 230                 235                 240

Glu Leu Leu Phe Gly Pro Asp Ala Arg Cys Phe Thr Arg Met Thr Pro
            245                 250                 255

Ala Leu Leu Val Leu Arg Leu Pro
            260

<210> SEQ ID NO 29
<211> LENGTH: 243
<212> TYPE: PRT
<213> ORGANISM: artificial sequence
<220> FEATURE:
<223> OTHER INFORMATION: polypeptide

<400> SEQUENCE: 29

Ala Glu Ala Pro Gly Gly Glu Val Ser Gly Thr Pro Ala Ser Pro Gly
1               5                   10                  15

Glu Pro Ala Thr Gly Thr Gly Gly Leu Leu Phe Gln Pro Asp Trp Asp
            20                  25                  30

Trp Pro Pro Ser Ala Pro Gln Asp Pro Leu Cys Leu Val Thr Leu Asp
            35                  40                  45

Lys Gly Gly Asn Gly Ser Ser Pro Pro Leu Arg Val Ala Gly Ala Leu
    50                  55                  60

Arg Gly Tyr Glu His Thr Phe Leu Glu Ala Val Arg Arg Ala Arg Trp
65                  70                  75                  80

Gly Pro His Asp Leu Ala Thr Phe Gly Ala Cys Ala Ala Ser Asp Gly
                85                  90                  95

Arg Thr Thr Gln Leu Ser Leu Arg Gln Leu Gln Ala Trp Leu Gly Ala
            100                 105                 110

Pro Gly Gly Arg Arg Leu Val Val Leu His Leu Glu Glu Val Thr Trp
            115                 120                 125

Glu Pro Ala Leu Ser Leu Lys Phe Gln Glu Pro Pro Gly Gly Ala
        130                 135                 140

Ser Pro Leu Glu Leu Ala Leu Leu Val Leu Tyr Pro Gly Pro Gly Pro
145                 150                 155                 160

Glu Val Ala Val Thr Gly Ala Gly Leu Pro Gly Thr Gln Asn Leu Cys
                165                 170                 175

Arg Ser Arg Asn Thr Arg Tyr Leu Val Leu Ala Leu Asp His Pro Val
            180                 185                 190

Gly Ala Trp His Ser Pro Arg Val Thr Leu Thr Val His Ala Arg Gly
            195                 200                 205

Asp Gly Ala Pro Leu Ser Thr Pro Gln Leu Gln Glu Leu Leu Phe Gly
        210                 215                 220

Pro Asp Ala Arg Cys Phe Thr Arg Met Thr Pro Ala Leu Leu Val Leu
225                 230                 235                 240

Arg Leu Pro

<210> SEQ ID NO 30
<211> LENGTH: 165
```

```
<212> TYPE: PRT
<213> ORGANISM: artificial sequence
<220> FEATURE:
<223> OTHER INFORMATION: polypeptide

<400> SEQUENCE: 30

Met Gly Ala Leu Ala Leu Trp Pro Leu Ala Leu Ser Gly Met
1               5                   10                  15

Gly Pro Leu Leu Gly Ala Glu Ala Pro Gly Gly Glu Val Ser Gly Thr
                20                  25                  30

Pro Ala Ser Pro Gly Glu Pro Ala Thr Gly Thr Gly Gly Leu Leu Phe
            35                  40                  45

Gln Pro Asp Trp Asp Trp Pro Ser Ala Pro Gln Asp Pro Leu Cys
        50                  55                  60

Leu Val Thr Leu Asp Lys Gly Asn Gly Ser Ser Pro Pro Leu Arg
65                  70                  75                  80

Val Ala Gly Ala Leu Arg Gly Tyr Glu His Thr Phe Leu Glu Ala Val
                85                  90                  95

Arg Arg Ala Arg Trp Gly Pro His Asp Leu Ala Thr Phe Gly Ala Cys
                100                 105                 110

Ala Ala Ser Asp Gly Arg Thr Thr Gln Leu Ser Leu Arg Gln Leu Gln
                115                 120                 125

Ala Trp Leu Gly Ala Pro Gly Gly Arg Arg Leu Val Val Leu His Leu
            130                 135                 140

Glu Glu Val Thr Trp Glu Pro Ala Leu Ser Leu Lys Phe Gln Glu Pro
145                 150                 155                 160

Pro Pro Gly Gly Ala
                165

<210> SEQ ID NO 31
<211> LENGTH: 144
<212> TYPE: PRT
<213> ORGANISM: artificial sequence
<220> FEATURE:
<223> OTHER INFORMATION: polypeptide

<400> SEQUENCE: 31

Ala Glu Ala Pro Gly Gly Glu Val Ser Gly Thr Pro Ala Ser Pro Gly
1               5                   10                  15

Glu Pro Ala Thr Gly Thr Gly Gly Leu Leu Phe Gln Pro Asp Trp Asp
                20                  25                  30

Trp Pro Pro Ser Ala Pro Gln Asp Pro Leu Cys Leu Val Thr Leu Asp
            35                  40                  45

Lys Gly Asn Gly Ser Ser Pro Pro Leu Arg Val Ala Gly Ala Leu
50                  55                  60

Arg Gly Tyr Glu His Thr Phe Leu Glu Ala Val Arg Arg Ala Arg Trp
65                  70                  75                  80

Gly Pro His Asp Leu Ala Thr Phe Gly Ala Cys Ala Ala Ser Asp Gly
                85                  90                  95

Arg Thr Thr Gln Leu Ser Leu Arg Gln Leu Gln Ala Trp Leu Gly Ala
                100                 105                 110

Pro Gly Gly Arg Arg Leu Val Val Leu His Leu Glu Glu Val Thr Trp
            115                 120                 125

Glu Pro Ala Leu Ser Leu Lys Phe Gln Glu Pro Pro Pro Gly Gly Ala
130                 135                 140

<210> SEQ ID NO 32
```

```
<211> LENGTH: 100
<212> TYPE: PRT
<213> ORGANISM: artificial sequence
<220> FEATURE:
<223> OTHER INFORMATION: polypeptide

<400> SEQUENCE: 32

Ser Pro Pro Glu Leu Ala Leu Leu Val Val Tyr Pro Gly Pro Gly Leu
1               5                   10                  15

Glu Val Thr Val Thr Gly Ala Gly Leu Pro Gly Thr Gln Ser Leu Cys
            20                  25                  30

Leu Thr Ala Asp Ser Asp Phe Leu Ala Leu Val Val Asp His Pro Glu
        35                  40                  45

Gly Ala Trp Arg Arg Pro Gly Leu Ala Leu Thr Leu Arg Arg Arg Gly
50                  55                  60

Asn Gly Ala Leu Leu Ser Thr Ala Gln Leu Gln Ala Leu Leu Phe Gly
65                  70                  75                  80

Ala Asp Ser Arg Cys Phe Thr Arg Lys Thr Pro Ala Leu Leu Leu Leu
                85                  90                  95

Leu Pro Ala Arg
            100

<210> SEQ ID NO 33
<211> LENGTH: 575
<212> TYPE: PRT
<213> ORGANISM: Bos taurus

<400> SEQUENCE: 33

Met Pro Gly Pro Ser Leu Ser Leu Ala Leu Val Leu Ser Ala Met Gly
1               5                   10                  15

Ala Leu Leu Arg Pro Gly Thr Pro Arg Glu Glu Val Phe Ser Thr Ser
            20                  25                  30

Ala Leu Pro Arg Glu Gln Ala Thr Gly Ser Gly Ala Leu Ile Phe Gln
        35                  40                  45

Gln Ala Trp Asp Trp Pro Leu Ser Ser Leu Trp Leu Pro Gly Ser Pro
50                  55                  60

Leu Asp Pro Leu Cys Leu Val Thr Leu His Gly Ser Gly Asn Gly Ser
65                  70                  75                  80

Arg Ala Pro Leu Arg Val Val Gly Val Leu Ser Ser Tyr Glu Gln Ala
                85                  90                  95

Phe Leu Glu Ala Val Arg Arg Thr His Trp Gly Leu Ser Asp Leu Thr
            100                 105                 110

Thr Phe Ala Val Cys Pro Ala Gly Asn Gly Gln Pro Val Leu Pro His
        115                 120                 125

Leu Gln Arg Leu Gln Ala Trp Leu Gly Glu Pro Gly Gly Arg Trp Leu
130                 135                 140

Val Val Leu His Leu Glu Glu Val Thr Trp Glu Pro Thr Pro Leu Leu
145                 150                 155                 160

Arg Phe Gln Glu Pro Pro Gly Gly Ala Ser Pro Pro Glu Leu Ala
                165                 170                 175

Leu Leu Val Val Tyr Pro Gly Pro Gly Leu Glu Val Thr Val Thr Gly
            180                 185                 190

Ala Gly Leu Pro Gly Thr Gln Ser Leu Cys Leu Thr Ala Asp Ser Asp
        195                 200                 205

Phe Leu Ala Leu Val Val Asp His Pro Glu Gly Ala Trp Arg Arg Pro
210                 215                 220
```

```
Gly Leu Ala Leu Thr Leu Arg Arg Arg Gly Asn Gly Ala Leu Leu Ser
225                 230                 235                 240

Thr Ala Gln Leu Gln Ala Leu Leu Phe Gly Ala Asp Ser Arg Cys Phe
            245                 250                 255

Thr Arg Lys Thr Pro Ala Leu Leu Leu Leu Pro Ala Arg Ser Ser
            260                 265                 270

Ala Pro Met Pro Ala His Gly Arg Leu Asp Leu Val Pro Phe Pro Gln
        275                 280                 285

Pro Arg Ala Ser Pro Glu Pro Glu Glu Ala Pro Ser Ala Asp Pro
    290                 295                 300

Phe Leu Glu Thr Leu Thr Arg Leu Val Arg Ala Leu Ala Gly Pro Pro
305                 310                 315                 320

Ala Arg Ala Ser Pro Pro Arg Leu Ala Leu Asp Pro Gly Ala Leu Ala
            325                 330                 335

Gly Phe Pro Gln Gly Gln Val Asn Leu Ser Asp Pro Ala Ala Leu Glu
            340                 345                 350

Arg Leu Leu Asp Gly Glu Glu Pro Leu Leu Leu Leu Pro Pro Thr
    355                 360                 365

Ala Ala Thr Thr Gly Val Pro Ala Thr Pro Gln Gly Pro Lys Ser Pro
            370                 375                 380

Leu Trp Ala Ala Gly Leu Ala Arg Arg Val Ala Ala Glu Leu Gln Ala
385                 390                 395                 400

Val Ala Ala Glu Leu Arg Ala Leu Pro Gly Leu Pro Ala Ala Pro
                405                 410                 415

Pro Leu Leu Ala Arg Leu Leu Ala Leu Cys Pro Gly Asn Pro Asp Ser
                420                 425                 430

Pro Gly Gly Pro Leu Arg Ala Leu Leu Leu Lys Ala Leu Gln Gly
            435                 440                 445

Leu Arg Ala Glu Trp Arg Gly Arg Glu Arg Ser Gly Ser Ala Arg Ala
    450                 455                 460

Gln Arg Ser Ala Gly Ala Ala Ala Asp Gly Pro Cys Ala Leu Arg
465                 470                 475                 480

Glu Leu Ser Val Asp Leu Arg Ala Glu Arg Ser Val Leu Ile Pro Glu
                485                 490                 495

Thr Tyr Gln Ala Asn Asn Cys Gln Gly Ala Cys Gly Trp Pro Gln Ser
            500                 505                 510

Asp Arg Asn Pro Arg Tyr Gly Asn His Val Val Leu Leu Leu Lys Met
    515                 520                 525

Gln Ala Arg Gly Ala Thr Leu Ala Arg Pro Pro Cys Cys Val Pro Thr
    530                 535                 540

Ala Tyr Thr Gly Lys Leu Leu Ile Ser Leu Ser Glu Glu Arg Ile Ser
545                 550                 555                 560

Ala His His Val Pro Asn Met Val Ala Thr Glu Cys Gly Cys Arg
                565                 570                 575

<210> SEQ ID NO 34
<211> LENGTH: 558
<212> TYPE: PRT
<213> ORGANISM: artificial sequence
<220> FEATURE:
<223> OTHER INFORMATION: polypeptide

<400> SEQUENCE: 34

Leu Leu Arg Pro Gly Thr Pro Arg Glu Glu Val Phe Thr Ser Ala
1               5                   10                  15
```

```
Leu Pro Arg Glu Gln Ala Thr Gly Ser Gly Ala Leu Ile Phe Gln Gln
            20                  25                  30

Ala Trp Asp Trp Pro Leu Ser Ser Leu Trp Leu Pro Gly Ser Pro Leu
        35                  40                  45

Asp Pro Leu Cys Leu Val Thr Leu His Gly Ser Gly Asn Gly Ser Arg
50                      55                  60

Ala Pro Leu Arg Val Val Gly Val Leu Ser Ser Tyr Glu Gln Ala Phe
65                  70                  75                  80

Leu Glu Ala Val Arg Arg Thr His Trp Gly Leu Ser Asp Leu Thr Thr
                85                  90                  95

Phe Ala Val Cys Pro Ala Gly Asn Gly Gln Pro Val Leu Pro His Leu
            100                 105                 110

Gln Arg Leu Gln Ala Trp Leu Gly Glu Pro Gly Gly Arg Trp Leu Val
        115                 120                 125

Val Leu His Leu Glu Glu Val Thr Trp Glu Pro Thr Pro Leu Leu Arg
    130                 135                 140

Phe Gln Glu Pro Pro Gly Gly Ala Ser Pro Pro Glu Leu Ala Leu
145                 150                 155                 160

Leu Val Val Tyr Pro Gly Pro Gly Leu Glu Val Thr Val Thr Gly Ala
                165                 170                 175

Gly Leu Pro Gly Thr Gln Ser Leu Cys Leu Thr Ala Asp Ser Asp Phe
            180                 185                 190

Leu Ala Leu Val Val Asp His Pro Glu Gly Ala Trp Arg Arg Pro Gly
        195                 200                 205

Leu Ala Leu Thr Leu Arg Arg Gly Asn Gly Ala Leu Leu Ser Thr
    210                 215                 220

Ala Gln Leu Gln Ala Leu Leu Phe Gly Ala Asp Ser Arg Cys Phe Thr
225                 230                 235                 240

Arg Lys Thr Pro Ala Leu Leu Leu Leu Pro Ala Arg Ser Ser Ala
                245                 250                 255

Pro Met Pro Ala His Gly Arg Leu Asp Leu Val Pro Phe Pro Gln Pro
            260                 265                 270

Arg Ala Ser Pro Glu Pro Glu Glu Ala Pro Ser Ala Asp Pro Phe
        275                 280                 285

Leu Glu Thr Leu Thr Arg Leu Val Arg Ala Leu Ala Gly Pro Pro Ala
    290                 295                 300

Arg Ala Ser Pro Pro Arg Leu Ala Leu Asp Pro Gly Ala Leu Ala Gly
305                 310                 315                 320

Phe Pro Gln Gly Gln Val Asn Leu Ser Asp Pro Ala Ala Leu Glu Arg
                325                 330                 335

Leu Leu Asp Gly Glu Glu Pro Leu Leu Leu Leu Pro Pro Thr Ala
            340                 345                 350

Ala Thr Thr Gly Val Pro Ala Thr Pro Gln Gly Pro Lys Ser Pro Leu
        355                 360                 365

Trp Ala Ala Gly Leu Ala Arg Arg Val Ala Ala Glu Leu Gln Ala Val
    370                 375                 380

Ala Ala Glu Leu Arg Ala Leu Pro Gly Leu Pro Pro Ala Ala Pro Pro
385                 390                 395                 400

Leu Leu Ala Arg Leu Ala Leu Cys Pro Gly Asn Pro Asp Ser Pro
                405                 410                 415

Gly Gly Pro Leu Arg Ala Leu Leu Leu Lys Ala Leu Gln Gly Leu
            420                 425                 430

Arg Ala Glu Trp Arg Gly Arg Glu Arg Ser Gly Ser Ala Arg Ala Gln
```

```
                435                 440                 445
Arg Ser Ala Gly Ala Ala Ala Asp Gly Pro Cys Ala Leu Arg Glu
    450                 455                 460

Leu Ser Val Asp Leu Arg Ala Glu Arg Ser Val Leu Ile Pro Glu Thr
465                 470                 475                 480

Tyr Gln Ala Asn Asn Cys Gln Gly Ala Cys Gly Trp Pro Gln Ser Asp
                485                 490                 495

Arg Asn Pro Arg Tyr Gly Asn His Val Val Leu Leu Lys Met Gln
                500                 505                 510

Ala Arg Gly Ala Thr Leu Ala Arg Pro Pro Cys Cys Val Pro Thr Ala
                515                 520                 525

Tyr Thr Gly Lys Leu Leu Ile Ser Leu Ser Glu Glu Arg Ile Ser Ala
                530                 535                 540

His His Val Pro Asn Met Val Ala Thr Glu Cys Gly Cys Arg
545                 550                 555

<210> SEQ ID NO 35
<211> LENGTH: 551
<212> TYPE: PRT
<213> ORGANISM: artificial sequence
<220> FEATURE:
<223> OTHER INFORMATION: polypeptide

<400> SEQUENCE: 35

Arg Glu Glu Val Phe Ser Thr Ser Ala Leu Pro Arg Glu Gln Ala Thr
1               5                   10                  15

Gly Ser Gly Ala Leu Ile Phe Gln Gln Ala Trp Asp Trp Pro Leu Ser
                20                  25                  30

Ser Leu Trp Leu Pro Gly Ser Pro Leu Asp Pro Leu Cys Leu Val Thr
            35                  40                  45

Leu His Gly Ser Gly Asn Gly Ser Arg Ala Pro Leu Arg Val Val Gly
    50                  55                  60

Val Leu Ser Ser Tyr Glu Gln Ala Phe Leu Glu Ala Val Arg Arg Thr
65                  70                  75                  80

His Trp Gly Leu Ser Asp Leu Thr Thr Phe Ala Val Cys Pro Ala Gly
                85                  90                  95

Asn Gly Gln Pro Val Leu Pro His Leu Gln Arg Leu Gln Ala Trp Leu
                100                 105                 110

Gly Glu Pro Gly Gly Arg Trp Leu Val Val Leu His Leu Glu Glu Val
            115                 120                 125

Thr Trp Glu Pro Thr Pro Leu Leu Arg Phe Gln Glu Pro Pro Pro Gly
    130                 135                 140

Gly Ala Ser Pro Pro Glu Leu Ala Leu Leu Val Val Tyr Pro Gly Pro
145                 150                 155                 160

Gly Leu Glu Val Thr Val Thr Gly Ala Gly Leu Pro Gly Thr Gln Ser
                165                 170                 175

Leu Cys Leu Thr Ala Asp Ser Asp Phe Leu Ala Leu Val Val Asp His
                180                 185                 190

Pro Glu Gly Ala Trp Arg Arg Pro Gly Leu Ala Leu Thr Leu Arg Arg
            195                 200                 205

Arg Gly Asn Gly Ala Leu Leu Ser Thr Ala Gln Leu Gln Ala Leu Leu
    210                 215                 220

Phe Gly Ala Asp Ser Arg Cys Phe Thr Arg Lys Thr Pro Ala Leu Leu
225                 230                 235                 240

Leu Leu Leu Pro Ala Arg Ser Ser Ala Pro Met Pro Ala His Gly Arg
```

```
                245                 250                 255
Leu Asp Leu Val Pro Phe Pro Gln Pro Arg Ala Ser Pro Glu Pro Glu
            260                 265                 270

Glu Ala Pro Pro Ser Ala Asp Pro Phe Leu Glu Thr Leu Thr Arg Leu
            275                 280                 285

Val Arg Ala Leu Ala Gly Pro Pro Ala Arg Ala Ser Pro Pro Arg Leu
        290                 295                 300

Ala Leu Asp Pro Gly Ala Leu Ala Gly Phe Pro Gln Gly Gln Val Asn
305                 310                 315                 320

Leu Ser Asp Pro Ala Ala Leu Glu Arg Leu Leu Asp Gly Glu Glu Pro
            325                 330                 335

Leu Leu Leu Leu Leu Pro Pro Thr Ala Ala Thr Thr Gly Val Pro Ala
            340                 345                 350

Thr Pro Gln Gly Pro Lys Ser Pro Leu Trp Ala Ala Gly Leu Ala Arg
            355                 360                 365

Arg Val Ala Ala Glu Leu Gln Ala Val Ala Ala Glu Leu Arg Ala Leu
        370                 375                 380

Pro Gly Leu Pro Pro Ala Ala Pro Pro Leu Leu Ala Arg Leu Leu Ala
385                 390                 395                 400

Leu Cys Pro Gly Asn Pro Asp Ser Pro Gly Gly Pro Leu Arg Ala Leu
                405                 410                 415

Leu Leu Leu Lys Ala Leu Gln Gly Leu Arg Ala Glu Trp Arg Gly Arg
            420                 425                 430

Glu Arg Ser Gly Ser Ala Arg Ala Gln Arg Ser Ala Gly Ala Ala Ala
            435                 440                 445

Ala Asp Gly Pro Cys Ala Leu Arg Glu Leu Ser Val Asp Leu Arg Ala
450                 455                 460

Glu Arg Ser Val Leu Ile Pro Glu Thr Tyr Gln Ala Asn Asn Cys Gln
465                 470                 475                 480

Gly Ala Cys Gly Trp Pro Gln Ser Asp Arg Asn Pro Arg Tyr Gly Asn
                485                 490                 495

His Val Val Leu Leu Leu Lys Met Gln Ala Arg Gly Ala Thr Leu Ala
            500                 505                 510

Arg Pro Pro Cys Cys Val Pro Thr Ala Tyr Thr Gly Lys Leu Leu Ile
            515                 520                 525

Ser Leu Ser Glu Glu Arg Ile Ser Ala His His Val Pro Asn Met Val
            530                 535                 540

Ala Thr Glu Cys Gly Cys Arg
545                 550

<210> SEQ ID NO 36
<211> LENGTH: 466
<212> TYPE: PRT
<213> ORGANISM: artificial sequence
<220> FEATURE:
<223> OTHER INFORMATION: polypeptide

<400> SEQUENCE: 36

Met Pro Gly Pro Ser Leu Ser Leu Ala Leu Val Leu Ser Ala Met Gly
1               5                   10                  15

Ala Leu Leu Arg Pro Gly Thr Pro Arg Glu Glu Val Phe Ser Thr Ser
            20                  25                  30

Ala Leu Pro Arg Glu Gln Ala Thr Gly Ser Gly Ala Leu Ile Phe Gln
            35                  40                  45

Gln Ala Trp Asp Trp Pro Leu Ser Ser Leu Trp Leu Pro Gly Ser Pro
```

```
            50                  55                  60
Leu Asp Pro Leu Cys Leu Val Thr Leu His Gly Ser Gly Asn Gly Ser
 65                  70                  75                  80

Arg Ala Pro Leu Arg Val Val Gly Val Leu Ser Ser Tyr Glu Gln Ala
                     85                  90                  95

Phe Leu Glu Ala Val Arg Arg Thr His Trp Gly Leu Ser Asp Leu Thr
                100                 105                 110

Thr Phe Ala Val Cys Pro Ala Gly Asn Gly Gln Pro Val Leu Pro His
                115                 120                 125

Leu Gln Arg Leu Gln Ala Trp Leu Gly Glu Pro Gly Gly Arg Trp Leu
            130                 135                 140

Val Val Leu His Leu Glu Glu Val Thr Trp Glu Pro Thr Pro Leu Leu
145                 150                 155                 160

Arg Phe Gln Glu Pro Pro Gly Gly Ala Ser Pro Pro Glu Leu Ala
                165                 170                 175

Leu Leu Val Val Tyr Pro Gly Pro Gly Leu Glu Val Thr Val Thr Gly
                180                 185                 190

Ala Gly Leu Pro Gly Thr Gln Ser Leu Cys Leu Thr Ala Asp Ser Asp
            195                 200                 205

Phe Leu Ala Leu Val Val Asp His Pro Glu Gly Ala Trp Arg Arg Pro
210                 215                 220

Gly Leu Ala Leu Thr Leu Arg Arg Gly Asn Gly Ala Leu Leu Ser
225                 230                 235                 240

Thr Ala Gln Leu Gln Ala Leu Leu Phe Gly Ala Asp Ser Arg Cys Phe
                245                 250                 255

Thr Arg Lys Thr Pro Ala Leu Leu Leu Leu Pro Ala Arg Ser Ser
            260                 265                 270

Ala Pro Met Pro Ala His Gly Arg Leu Asp Leu Val Pro Phe Pro Gln
            275                 280                 285

Pro Arg Ala Ser Pro Glu Pro Glu Ala Pro Pro Ser Ala Asp Pro
            290                 295                 300

Phe Leu Glu Thr Leu Thr Arg Leu Val Arg Ala Leu Ala Gly Pro Pro
305                 310                 315                 320

Ala Arg Ala Ser Pro Pro Arg Leu Ala Leu Asp Pro Gly Ala Leu Ala
                325                 330                 335

Gly Phe Pro Gln Gly Gln Val Asn Leu Ser Asp Pro Ala Ala Leu Glu
                340                 345                 350

Arg Leu Leu Asp Gly Glu Glu Pro Leu Leu Leu Leu Pro Pro Thr
            355                 360                 365

Ala Ala Thr Thr Gly Val Pro Ala Thr Pro Gln Gly Pro Lys Ser Pro
            370                 375                 380

Leu Trp Ala Ala Gly Leu Ala Arg Arg Val Ala Glu Leu Gln Ala
385                 390                 395                 400

Val Ala Ala Glu Leu Arg Ala Leu Pro Gly Leu Pro Pro Ala Ala Pro
                405                 410                 415

Pro Leu Leu Ala Arg Leu Leu Ala Leu Cys Pro Gly Asn Pro Asp Ser
                420                 425                 430

Pro Gly Gly Pro Leu Arg Ala Leu Leu Leu Lys Ala Leu Gln Gly
            435                 440                 445

Leu Arg Ala Glu Trp Arg Gly Arg Glu Arg Ser Gly Ser Ala Arg Ala
    450                 455                 460

Gln Arg
465
```

<210> SEQ ID NO 37
<211> LENGTH: 449
<212> TYPE: PRT
<213> ORGANISM: artificial sequence
<220> FEATURE:
<223> OTHER INFORMATION: polypeptide

<400> SEQUENCE: 37

```
Leu Leu Arg Pro Gly Thr Pro Arg Glu Val Phe Ser Thr Ser Ala
1               5                   10                  15

Leu Pro Arg Glu Gln Ala Thr Gly Ser Gly Ala Leu Ile Phe Gln Gln
                20                  25                  30

Ala Trp Asp Trp Pro Leu Ser Ser Leu Trp Leu Pro Gly Ser Pro Leu
            35                  40                  45

Asp Pro Leu Cys Leu Val Thr Leu His Gly Ser Gly Asn Gly Ser Arg
        50                  55                  60

Ala Pro Leu Arg Val Val Gly Val Leu Ser Ser Tyr Glu Gln Ala Phe
65                  70                  75                  80

Leu Glu Ala Val Arg Arg Thr His Trp Gly Leu Ser Asp Leu Thr Thr
                85                  90                  95

Phe Ala Val Cys Pro Ala Gly Asn Gly Gln Pro Val Leu Pro His Leu
            100                 105                 110

Gln Arg Leu Gln Ala Trp Leu Gly Glu Pro Gly Gly Arg Trp Leu Val
        115                 120                 125

Val Leu His Leu Glu Glu Val Thr Trp Glu Pro Thr Pro Leu Leu Arg
130                 135                 140

Phe Gln Glu Pro Pro Gly Gly Ala Ser Pro Pro Glu Leu Ala Leu
145                 150                 155                 160

Leu Val Val Tyr Pro Gly Pro Gly Leu Glu Val Thr Val Thr Gly Ala
                165                 170                 175

Gly Leu Pro Gly Thr Gln Ser Leu Cys Leu Thr Ala Asp Ser Asp Phe
            180                 185                 190

Leu Ala Leu Val Val Asp His Pro Glu Gly Ala Trp Arg Arg Pro Gly
        195                 200                 205

Leu Ala Leu Thr Leu Arg Arg Arg Gly Asn Gly Ala Leu Leu Ser Thr
    210                 215                 220

Ala Gln Leu Gln Ala Leu Leu Phe Gly Ala Asp Ser Arg Cys Phe Thr
225                 230                 235                 240

Arg Lys Thr Pro Ala Leu Leu Leu Leu Pro Ala Arg Ser Ser Ala
                245                 250                 255

Pro Met Pro Ala His Gly Arg Leu Asp Leu Val Pro Phe Pro Gln Pro
            260                 265                 270

Arg Ala Ser Pro Glu Pro Glu Leu Ala Pro Ser Ala Asp Pro Phe
        275                 280                 285

Leu Glu Thr Leu Thr Arg Leu Val Arg Ala Leu Ala Gly Pro Pro Ala
    290                 295                 300

Arg Ala Ser Pro Pro Arg Leu Ala Leu Asp Pro Gly Ala Leu Ala Gly
305                 310                 315                 320

Phe Pro Gln Gly Gln Val Asn Leu Ser Asp Pro Ala Ala Leu Glu Arg
                325                 330                 335

Leu Leu Asp Gly Glu Glu Pro Leu Leu Leu Leu Pro Pro Thr Ala
            340                 345                 350

Ala Thr Thr Gly Val Pro Ala Thr Pro Gln Gly Pro Lys Ser Pro Leu
        355                 360                 365
```

```
Trp Ala Ala Gly Leu Ala Arg Arg Val Ala Ala Glu Leu Gln Ala Val
        370                 375                 380

Ala Ala Glu Leu Arg Ala Leu Pro Gly Leu Pro Pro Ala Ala Pro Pro
385                 390                 395                 400

Leu Leu Ala Arg Leu Leu Ala Leu Cys Pro Gly Asn Pro Asp Ser Pro
                405                 410                 415

Gly Gly Pro Leu Arg Ala Leu Leu Leu Lys Ala Leu Gln Gly Leu
                420                 425                 430

Arg Ala Glu Trp Arg Gly Arg Glu Arg Ser Gly Ser Ala Arg Ala Gln
        435                 440                 445

Arg

<210> SEQ ID NO 38
<211> LENGTH: 442
<212> TYPE: PRT
<213> ORGANISM: artificial sequence
<220> FEATURE:
<223> OTHER INFORMATION: polypeptide

<400> SEQUENCE: 38

Arg Glu Glu Val Phe Ser Thr Ser Ala Leu Pro Arg Glu Gln Ala Thr
1               5                   10                  15

Gly Ser Gly Ala Leu Ile Phe Gln Gln Ala Trp Asp Trp Pro Leu Ser
            20                  25                  30

Ser Leu Trp Leu Pro Gly Ser Pro Leu Asp Pro Leu Cys Leu Val Thr
        35                  40                  45

Leu His Gly Ser Gly Asn Gly Ser Arg Ala Pro Leu Arg Val Val Gly
    50                  55                  60

Val Leu Ser Ser Tyr Glu Gln Ala Phe Leu Glu Ala Val Arg Arg Thr
65                  70                  75                  80

His Trp Gly Leu Ser Asp Leu Thr Thr Phe Ala Val Cys Pro Ala Gly
                85                  90                  95

Asn Gly Gln Pro Val Leu Pro His Leu Gln Arg Leu Gln Ala Trp Leu
            100                 105                 110

Gly Glu Pro Gly Gly Arg Trp Leu Val Val Leu His Leu Glu Glu Val
        115                 120                 125

Thr Trp Glu Pro Thr Pro Leu Leu Arg Phe Gln Glu Pro Pro Pro Gly
130                 135                 140

Gly Ala Ser Pro Pro Glu Leu Ala Leu Leu Val Val Tyr Pro Gly Pro
145                 150                 155                 160

Gly Leu Glu Val Thr Val Thr Gly Ala Gly Leu Pro Gly Thr Gln Ser
                165                 170                 175

Leu Cys Leu Thr Ala Asp Ser Asp Phe Leu Ala Leu Val Val Asp His
            180                 185                 190

Pro Glu Gly Ala Trp Arg Arg Pro Gly Leu Ala Leu Thr Leu Arg Arg
        195                 200                 205

Arg Gly Asn Gly Ala Leu Leu Ser Thr Ala Gln Leu Gln Ala Leu Leu
    210                 215                 220

Phe Gly Ala Asp Ser Arg Cys Phe Thr Arg Lys Thr Pro Ala Leu Leu
225                 230                 235                 240

Leu Leu Leu Pro Ala Arg Ser Ser Ala Pro Met Pro Ala His Gly Arg
                245                 250                 255

Leu Asp Leu Val Pro Phe Pro Gln Pro Arg Ala Ser Pro Glu Pro Glu
            260                 265                 270
```

```
Glu Ala Pro Pro Ser Ala Asp Pro Phe Leu Glu Thr Leu Thr Arg Leu
            275                 280                 285

Val Arg Ala Leu Ala Gly Pro Pro Ala Arg Ala Ser Pro Pro Arg Leu
    290                 295                 300

Ala Leu Asp Pro Gly Ala Leu Ala Gly Phe Pro Gln Gly Gln Val Asn
305                 310                 315                 320

Leu Ser Asp Pro Ala Ala Leu Glu Arg Leu Leu Asp Gly Glu Glu Pro
                325                 330                 335

Leu Leu Leu Leu Leu Pro Pro Thr Ala Ala Thr Thr Gly Val Pro Ala
            340                 345                 350

Thr Pro Gln Gly Pro Lys Ser Pro Leu Trp Ala Ala Gly Leu Ala Arg
    355                 360                 365

Arg Val Ala Ala Glu Leu Gln Ala Val Ala Ala Glu Leu Arg Ala Leu
    370                 375                 380

Pro Gly Leu Pro Pro Ala Ala Pro Pro Leu Leu Ala Arg Leu Leu Ala
385                 390                 395                 400

Leu Cys Pro Gly Asn Pro Asp Ser Pro Gly Gly Pro Leu Arg Ala Leu
                405                 410                 415

Leu Leu Leu Lys Ala Leu Gln Gly Leu Arg Ala Glu Trp Arg Gly Arg
            420                 425                 430

Glu Arg Ser Gly Ser Ala Arg Ala Gln Arg
        435                 440
```

<210> SEQ ID NO 39
<211> LENGTH: 270
<212> TYPE: PRT
<213> ORGANISM: artificial sequence
<220> FEATURE:
<223> OTHER INFORMATION: polypeptide

<400> SEQUENCE: 39

```
Met Pro Gly Pro Ser Leu Ser Leu Ala Leu Val Leu Ser Ala Met Gly
1               5                   10                  15

Ala Leu Leu Arg Pro Gly Thr Pro Arg Glu Glu Val Phe Ser Thr Ser
            20                  25                  30

Ala Leu Pro Arg Glu Gln Ala Thr Gly Ser Gly Ala Leu Ile Phe Gln
        35                  40                  45

Gln Ala Trp Asp Trp Pro Leu Ser Ser Leu Trp Leu Pro Gly Ser Pro
    50                  55                  60

Leu Asp Pro Leu Cys Leu Val Thr Leu His Gly Ser Gly Asn Gly Ser
65                  70                  75                  80

Arg Ala Pro Leu Arg Val Val Gly Val Leu Ser Ser Tyr Glu Gln Ala
                85                  90                  95

Phe Leu Glu Ala Val Arg Arg Thr His Trp Gly Leu Ser Asp Leu Thr
            100                 105                 110

Thr Phe Ala Val Cys Pro Ala Gly Asn Gly Gln Pro Val Leu Pro His
        115                 120                 125

Leu Gln Arg Leu Gln Ala Trp Leu Gly Glu Pro Gly Gly Arg Trp Leu
    130                 135                 140

Val Val Leu His Leu Glu Glu Val Thr Trp Glu Pro Thr Pro Leu Leu
145                 150                 155                 160

Arg Phe Gln Glu Pro Pro Gly Gly Ala Ser Pro Pro Glu Leu Ala
                165                 170                 175

Leu Leu Val Val Tyr Pro Gly Pro Gly Leu Glu Val Thr Val Thr Gly
            180                 185                 190
```

```
Ala Gly Leu Pro Gly Thr Gln Ser Leu Cys Leu Thr Ala Asp Ser Asp
            195                 200                 205

Phe Leu Ala Leu Val Val Asp His Pro Glu Gly Ala Trp Arg Arg Pro
210                 215                 220

Gly Leu Ala Leu Thr Leu Arg Arg Arg Gly Asn Gly Ala Leu Leu Ser
225                 230                 235                 240

Thr Ala Gln Leu Gln Ala Leu Leu Phe Gly Ala Asp Ser Arg Cys Phe
            245                 250                 255

Thr Arg Lys Thr Pro Ala Leu Leu Leu Leu Pro Ala Arg
            260                 265                 270

<210> SEQ ID NO 40
<211> LENGTH: 253
<212> TYPE: PRT
<213> ORGANISM: artificial sequence
<220> FEATURE:
<223> OTHER INFORMATION: polypeptide

<400> SEQUENCE: 40

Leu Leu Arg Pro Gly Thr Pro Arg Glu Glu Val Phe Ser Thr Ser Ala
1               5                   10                  15

Leu Pro Arg Glu Gln Ala Thr Gly Ser Gly Ala Leu Ile Phe Gln Gln
            20                  25                  30

Ala Trp Asp Trp Pro Leu Ser Ser Leu Trp Leu Pro Gly Ser Pro Leu
        35                  40                  45

Asp Pro Leu Cys Leu Val Thr Leu His Gly Ser Gly Asn Gly Ser Arg
    50                  55                  60

Ala Pro Leu Arg Val Val Gly Val Leu Ser Ser Tyr Glu Gln Ala Phe
65                  70                  75                  80

Leu Glu Ala Val Arg Arg Thr His Trp Gly Leu Ser Asp Leu Thr Thr
                85                  90                  95

Phe Ala Val Cys Pro Ala Gly Asn Gly Gln Pro Val Leu Pro His Leu
            100                 105                 110

Gln Arg Leu Gln Ala Trp Leu Gly Glu Pro Gly Gly Arg Trp Leu Val
        115                 120                 125

Val Leu His Leu Glu Glu Val Thr Trp Glu Pro Thr Pro Leu Leu Arg
    130                 135                 140

Phe Gln Glu Pro Pro Gly Gly Ala Ser Pro Pro Glu Leu Ala Leu
145                 150                 155                 160

Leu Val Val Tyr Pro Gly Pro Gly Leu Glu Val Thr Val Thr Gly Ala
                165                 170                 175

Gly Leu Pro Gly Thr Gln Ser Leu Cys Leu Thr Ala Asp Ser Asp Phe
            180                 185                 190

Leu Ala Leu Val Val Asp His Pro Glu Gly Ala Trp Arg Arg Pro Gly
        195                 200                 205

Leu Ala Leu Thr Leu Arg Arg Arg Gly Asn Gly Ala Leu Leu Ser Thr
    210                 215                 220

Ala Gln Leu Gln Ala Leu Leu Phe Gly Ala Asp Ser Arg Cys Phe Thr
225                 230                 235                 240

Arg Lys Thr Pro Ala Leu Leu Leu Leu Pro Ala Arg
                245                 250

<210> SEQ ID NO 41
<211> LENGTH: 246
<212> TYPE: PRT
<213> ORGANISM: artificial sequence
<220> FEATURE:
```

<223> OTHER INFORMATION: polypeptide

<400> SEQUENCE: 41

Arg Glu Glu Val Phe Ser Thr Ser Ala Leu Pro Arg Glu Gln Ala Thr
1               5                   10                  15

Gly Ser Gly Ala Leu Ile Phe Gln Gln Ala Trp Asp Trp Pro Leu Ser
            20                  25                  30

Ser Leu Trp Leu Pro Gly Ser Pro Leu Asp Pro Leu Cys Leu Val Thr
        35                  40                  45

Leu His Gly Ser Gly Asn Gly Ser Arg Ala Pro Leu Arg Val Val Gly
    50                  55                  60

Val Leu Ser Ser Tyr Glu Gln Ala Phe Leu Glu Ala Val Arg Arg Thr
65                  70                  75                  80

His Trp Gly Leu Ser Asp Leu Thr Thr Phe Ala Val Cys Pro Ala Gly
                85                  90                  95

Asn Gly Gln Pro Val Leu Pro His Leu Gln Arg Leu Gln Ala Trp Leu
            100                 105                 110

Gly Glu Pro Gly Gly Arg Trp Leu Val Val Leu His Leu Glu Glu Val
        115                 120                 125

Thr Trp Glu Pro Thr Pro Leu Leu Arg Phe Gln Glu Pro Pro Pro Gly
    130                 135                 140

Gly Ala Ser Pro Pro Glu Leu Ala Leu Leu Val Val Tyr Pro Gly Pro
145                 150                 155                 160

Gly Leu Glu Val Thr Val Thr Gly Ala Gly Leu Pro Gly Thr Gln Ser
                165                 170                 175

Leu Cys Leu Thr Ala Asp Ser Asp Phe Leu Ala Leu Val Val Asp His
            180                 185                 190

Pro Glu Gly Ala Trp Arg Arg Pro Gly Leu Ala Leu Thr Leu Arg Arg
        195                 200                 205

Arg Gly Asn Gly Ala Leu Leu Ser Thr Ala Gln Leu Gln Ala Leu Leu
    210                 215                 220

Phe Gly Ala Asp Ser Arg Cys Phe Thr Arg Lys Thr Pro Ala Leu Leu
225                 230                 235                 240

Leu Leu Leu Pro Ala Arg
                245

<210> SEQ ID NO 42
<211> LENGTH: 170
<212> TYPE: PRT
<213> ORGANISM: artificial sequence
<220> FEATURE:
<223> OTHER INFORMATION: polypeptide

<400> SEQUENCE: 42

Met Pro Gly Pro Ser Leu Ser Leu Ala Leu Val Leu Ser Ala Met Gly
1               5                   10                  15

Ala Leu Leu Arg Pro Gly Thr Pro Arg Glu Glu Val Phe Ser Thr Ser
            20                  25                  30

Ala Leu Pro Arg Glu Gln Ala Thr Gly Ser Gly Ala Leu Ile Phe Gln
        35                  40                  45

Gln Ala Trp Asp Trp Pro Leu Ser Ser Leu Trp Leu Pro Gly Ser Pro
    50                  55                  60

Leu Asp Pro Leu Cys Leu Val Thr Leu His Gly Ser Gly Asn Gly Ser
65                  70                  75                  80

Arg Ala Pro Leu Arg Val Val Gly Val Leu Ser Ser Tyr Glu Gln Ala
                85                  90                  95

Phe Leu Glu Ala Val Arg Arg Thr His Trp Gly Leu Ser Asp Leu Thr
                100                 105                 110

Thr Phe Ala Val Cys Pro Ala Gly Asn Gly Gln Pro Val Leu Pro His
            115                 120                 125

Leu Gln Arg Leu Gln Ala Trp Leu Gly Glu Pro Gly Gly Arg Trp Leu
        130                 135                 140

Val Val Leu His Leu Glu Glu Val Thr Trp Glu Pro Thr Pro Leu Leu
145                 150                 155                 160

Arg Phe Gln Glu Pro Pro Gly Gly Ala
                165                 170

<210> SEQ ID NO 43
<211> LENGTH: 153
<212> TYPE: PRT
<213> ORGANISM: artificial sequence
<220> FEATURE:
<223> OTHER INFORMATION: polypeptide

<400> SEQUENCE: 43

Leu Leu Arg Pro Gly Thr Pro Arg Glu Glu Val Phe Ser Thr Ser Ala
1               5                   10                  15

Leu Pro Arg Glu Gln Ala Thr Gly Ser Gly Ala Leu Ile Phe Gln Gln
            20                  25                  30

Ala Trp Asp Trp Pro Leu Ser Ser Leu Trp Leu Pro Gly Ser Pro Leu
        35                  40                  45

Asp Pro Leu Cys Leu Val Thr Leu His Gly Ser Gly Asn Gly Ser Arg
    50                  55                  60

Ala Pro Leu Arg Val Val Gly Val Leu Ser Ser Tyr Glu Gln Ala Phe
65                  70                  75                  80

Leu Glu Ala Val Arg Arg Thr His Trp Gly Leu Ser Asp Leu Thr Thr
                85                  90                  95

Phe Ala Val Cys Pro Ala Gly Asn Gly Gln Pro Val Leu Pro His Leu
            100                 105                 110

Gln Arg Leu Gln Ala Trp Leu Gly Glu Pro Gly Gly Arg Trp Leu Val
        115                 120                 125

Val Leu His Leu Glu Glu Val Thr Trp Glu Pro Thr Pro Leu Leu Arg
    130                 135                 140

Phe Gln Glu Pro Pro Gly Gly Ala
145                 150

<210> SEQ ID NO 44
<211> LENGTH: 146
<212> TYPE: PRT
<213> ORGANISM: artificial sequence
<220> FEATURE:
<223> OTHER INFORMATION: polypeptide

<400> SEQUENCE: 44

Arg Glu Glu Val Phe Ser Thr Ser Ala Leu Pro Arg Glu Gln Ala Thr
1               5                   10                  15

Gly Ser Gly Ala Leu Ile Phe Gln Gln Ala Trp Asp Trp Pro Leu Ser
            20                  25                  30

Ser Leu Trp Leu Pro Gly Ser Pro Leu Asp Pro Leu Cys Leu Val Thr
        35                  40                  45

Leu His Gly Ser Gly Asn Gly Ser Arg Ala Pro Leu Arg Val Val Gly
    50                  55                  60

Val Leu Ser Ser Tyr Glu Gln Ala Phe Leu Glu Ala Val Arg Arg Thr

His Trp Gly Leu Ser Asp Leu Thr Thr Phe Ala Val Cys Pro Ala Gly
             85                  90                  95

Asn Gly Gln Pro Val Leu Pro His Leu Gln Arg Leu Gln Ala Trp Leu
        100                 105                 110

Gly Glu Pro Gly Gly Arg Trp Leu Val Val Leu His Leu Glu Glu Val
        115                 120                 125

Thr Trp Glu Pro Thr Pro Leu Leu Arg Phe Gln Glu Pro Pro Pro Gly
    130                 135                 140

Gly Ala
145

<210> SEQ ID NO 45
<211> LENGTH: 12
<212> TYPE: PRT
<213> ORGANISM: artificial sequence
<220> FEATURE:
<223> OTHER INFORMATION: epitope

<400> SEQUENCE: 45

Val Leu Ala Val Asp Arg Pro Ala Gly Ala Trp Arg
1               5                   10

<210> SEQ ID NO 46
<211> LENGTH: 12
<212> TYPE: PRT
<213> ORGANISM: artificial sequence
<220> FEATURE:
<223> OTHER INFORMATION: epitope

<400> SEQUENCE: 46

Pro Arg Gly Glu Asp Ser Arg Leu Ser Thr Ala Arg
1               5                   10

<210> SEQ ID NO 47
<211> LENGTH: 12
<212> TYPE: PRT
<213> ORGANISM: artificial sequence
<220> FEATURE:
<223> OTHER INFORMATION: epitope

<400> SEQUENCE: 47

His Arg Cys Phe Thr Arg Met Thr Pro Ala Leu Leu
1               5                   10

<210> SEQ ID NO 48
<211> LENGTH: 12
<212> TYPE: PRT
<213> ORGANISM: artificial sequence
<220> FEATURE:
<223> OTHER INFORMATION: epitope

<400> SEQUENCE: 48

Ala Leu Ala Val Asp His Pro Ala Arg Ala Trp Arg
1               5                   10

<210> SEQ ID NO 49
<211> LENGTH: 12
<212> TYPE: PRT
<213> ORGANISM: artificial sequence
<220> FEATURE:
<223> OTHER INFORMATION: epitope

<400> SEQUENCE: 49

Pro Arg Gly Asp Gly Ala Pro Leu Ser Thr Ala Gln
1               5                   10

<210> SEQ ID NO 50
<211> LENGTH: 12
<212> TYPE: PRT
<213> ORGANISM: artificial sequence
<220> FEATURE:
<223> OTHER INFORMATION: epitope

<400> SEQUENCE: 50

Pro Arg Cys Phe Thr Arg Met Thr Pro Ala Leu Phe
1               5                   10

<210> SEQ ID NO 51
<211> LENGTH: 12
<212> TYPE: PRT
<213> ORGANISM: artificial sequence
<220> FEATURE:
<223> OTHER INFORMATION: epitope

<400> SEQUENCE: 51

Val Leu Ala Leu Asp His Pro Val Gly Ala Trp His
1               5                   10

<210> SEQ ID NO 52
<211> LENGTH: 12
<212> TYPE: PRT
<213> ORGANISM: artificial sequence
<220> FEATURE:
<223> OTHER INFORMATION: epitope

<400> SEQUENCE: 52

Ala Arg Gly Asp Gly Ala Pro Leu Ser Thr Pro Gln
1               5                   10

<210> SEQ ID NO 53
<211> LENGTH: 12
<212> TYPE: PRT
<213> ORGANISM: artificial sequence
<220> FEATURE:
<223> OTHER INFORMATION: epitope

<400> SEQUENCE: 53

Ala Arg Cys Phe Thr Arg Met Thr Pro Ala Leu Leu
1               5                   10

<210> SEQ ID NO 54
<211> LENGTH: 12
<212> TYPE: PRT
<213> ORGANISM: artificial sequence
<220> FEATURE:
<223> OTHER INFORMATION: epitope

<400> SEQUENCE: 54

Ala Leu Val Val Asp His Pro Glu Gly Ala Trp Arg
1               5                   10

<210> SEQ ID NO 55
<211> LENGTH: 12
<212> TYPE: PRT
<213> ORGANISM: artificial sequence
<220> FEATURE:
<223> OTHER INFORMATION: epitope

<400> SEQUENCE: 55

Arg Arg Gly Asn Gly Ala Leu Leu Ser Thr Ala Gln

```
<210> SEQ ID NO 56
<211> LENGTH: 12
<212> TYPE: PRT
<213> ORGANISM: artificial sequence
<220> FEATURE:
<223> OTHER INFORMATION: epitope

<400> SEQUENCE: 56

Ser Arg Cys Phe Thr Arg Lys Thr Pro Ala Leu Leu
1               5                   10

<210> SEQ ID NO 57
<211> LENGTH: 196
<212> TYPE: PRT
<213> ORGANISM: artificial sequence
<220> FEATURE:
<223> OTHER INFORMATION: polypeptide

<400> SEQUENCE: 57

Glu Pro Ala Pro Leu Pro Ala His Gly Gln Leu Asp Thr Val Pro Phe
1               5                   10                  15

Pro Pro Pro Arg Pro Ser Ala Glu Leu Glu Glu Ser Pro Pro Ser Ala
            20                  25                  30

Asp Pro Phe Leu Glu Thr Leu Thr Arg Leu Val Arg Ala Leu Arg Val
        35                  40                  45

Pro Pro Ala Arg Ala Ser Ala Pro Arg Leu Ala Leu Asp Pro Asp Ala
    50                  55                  60

Leu Ala Gly Phe Pro Gln Gly Leu Val Asn Leu Ser Asp Pro Ala Ala
65                  70                  75                  80

Leu Glu Arg Leu Leu Asp Gly Glu Pro Leu Leu Leu Leu Leu Leu Arg
                85                  90                  95

Pro Thr Ala Ala Thr Thr Gly Asp Pro Ala Pro Leu His Asp Pro Thr
            100                 105                 110

Ser Ala Pro Trp Ala Thr Ala Leu Ala Arg Arg Val Ala Ala Glu Leu
        115                 120                 125

Gln Ala Ala Ala Ala Glu Leu Arg Ser Leu Pro Gly Leu Pro Pro Ala
    130                 135                 140

Thr Ala Pro Leu Leu Ala Arg Leu Leu Ala Leu Cys Pro Gly Gly Pro
145                 150                 155                 160

Gly Gly Leu Gly Asp Pro Leu Arg Ala Leu Leu Leu Lys Ala Leu
                165                 170                 175

Gln Gly Leu Arg Val Glu Trp Arg Gly Arg Asp Pro Arg Gly Pro Gly
            180                 185                 190

Arg Ala Gln Arg
        195

<210> SEQ ID NO 58
<211> LENGTH: 199
<212> TYPE: PRT
<213> ORGANISM: artificial sequence
<220> FEATURE:
<223> OTHER INFORMATION: polypeptide

<400> SEQUENCE: 58

Gly Pro Ala Pro Met Pro Ala His Gly Arg Leu Asp Thr Val Pro Phe
1               5                   10                  15

Pro Pro Ala Arg Pro Ser Pro Glu Pro Glu Glu Pro Arg Pro Ser Ala
            20                  25                  30
```

```
Asp Pro Phe Leu Glu Thr Leu Thr Arg Leu Val Arg Ala Leu Arg Gly
            35                  40                  45

Pro Pro Thr Pro Ala Ser Pro Pro Arg Leu Ala Leu Asp Pro Gly Ala
 50                  55                  60

Leu Ala Ser Phe Pro Gln Gly Leu Val Asn Leu Ser Asp Pro Ala Ala
 65                  70                  75                  80

Leu Glu Arg Leu Leu Asp Gly Glu Pro Leu Leu Leu Leu Leu Leu Pro
                85                  90                  95

Pro Thr Ala Ala Ala Gly Asp Pro Ala Pro Leu Pro Asp Pro Ala
                 100                 105                 110

Ser Ala Pro Trp Ala Ala Gly Leu Ala Arg Arg Val Ala Ala Glu Leu
                 115                 120                 125

Gln Ala Ala Ala Glu Leu Arg Ser Leu Pro Gly Leu Pro Pro Ala
                 130                 135                 140

Ala Glu Pro Leu Leu Ala Arg Leu Leu Ala Leu Cys Pro Gly Asp Ala
145                 150                 155                 160

Glu Asp Gln Gly Gly Pro Gly Gly Pro Leu Arg Ala Leu Leu Leu Leu
                 165                 170                 175

Lys Ala Leu Gln Gly Leu Arg Ala Glu Trp Arg Gly Arg Glu Arg Ser
                 180                 185                 190

Gly Pro Gly Arg Ala Gln Arg
                 195

<210> SEQ ID NO 59
<211> LENGTH: 199
<212> TYPE: PRT
<213> ORGANISM: artificial sequence
<220> FEATURE:
<223> OTHER INFORMATION: polypeptide

<400> SEQUENCE: 59

Gly Pro Thr Ala Val Pro Ala Arg Gly Leu Leu Asp Leu Val Pro Phe
 1               5                  10                  15

Pro Pro Pro Arg Pro Ser Arg Glu Pro Ala Glu Pro Pro Ser Ala
                 20                  25                  30

Asp Pro Phe Leu Glu Thr Leu Thr Arg Leu Val Arg Ala Leu Arg Gly
            35                  40                  45

Pro Pro Thr Pro Ala Ser Pro Pro Arg Leu Ala Leu Asp Pro Gly Ala
 50                  55                  60

Leu Ala Gly Phe Pro Gln Gly Leu Leu Asn Leu Ser Asp Pro Ala Thr
 65                  70                  75                  80

Gln Glu Arg Leu Leu Gly Gly Glu Glu Pro Leu Leu Leu Leu Leu Pro
                85                  90                  95

Pro Pro Thr Ala Ala Ala Gly Pro Ala Pro Pro Arg Pro Ala
                 100                 105                 110

Ser Ala Pro Trp Ala Ala Gly Leu Ala Leu Arg Val Ala Ala Glu Leu
                 115                 120                 125

Arg Ala Ala Ala Glu Leu Arg Gly Leu Pro Gly Leu Pro Pro Ala
                 130                 135                 140

Ala Ala Pro Leu Leu Glu Arg Leu Leu Ala Leu Cys Pro Gly Gly Ser
145                 150                 155                 160

Gly Gly Ser Gly Gly Ser Gly Asp Pro Leu Arg Ala Leu Leu Leu Leu
                 165                 170                 175

Lys Ala Leu Gln Gly Leu Arg Ala Glu Trp Arg Gly Arg Glu Arg Gly
                 180                 185                 190
```

```
Gly Pro Pro Arg Ala Gln Arg
            195

<210> SEQ ID NO 60
<211> LENGTH: 196
<212> TYPE: PRT
<213> ORGANISM: artificial sequence
<220> FEATURE:
<223> OTHER INFORMATION: polypeptide

<400> SEQUENCE: 60

Ser Ser Ala Pro Met Pro Ala His Gly Arg Leu Asp Leu Val Pro Phe
1               5                   10                  15

Pro Gln Pro Arg Ala Ser Pro Glu Pro Glu Ala Pro Pro Ser Ala
            20                  25                  30

Asp Pro Phe Leu Glu Thr Leu Thr Arg Leu Val Arg Ala Leu Ala Gly
            35                  40                  45

Pro Pro Ala Arg Ala Ser Pro Pro Arg Leu Ala Leu Asp Pro Gly Ala
        50                  55                  60

Leu Ala Gly Phe Pro Gln Gly Gln Val Asn Leu Ser Asp Pro Ala Ala
65                  70                  75                  80

Leu Glu Arg Leu Leu Asp Gly Glu Glu Pro Leu Leu Leu Leu Leu Pro
                85                  90                  95

Pro Thr Ala Ala Thr Thr Gly Val Pro Ala Thr Pro Gln Gly Pro Lys
            100                 105                 110

Ser Pro Leu Trp Ala Ala Gly Leu Ala Arg Arg Val Ala Ala Glu Leu
            115                 120                 125

Gln Ala Val Ala Ala Glu Leu Arg Ala Leu Pro Gly Leu Pro Pro Ala
    130                 135                 140

Ala Pro Pro Leu Leu Ala Arg Leu Leu Ala Leu Cys Pro Gly Asn Pro
145                 150                 155                 160

Asp Ser Pro Gly Gly Pro Leu Arg Ala Leu Leu Leu Lys Ala Leu
                165                 170                 175

Gln Gly Leu Arg Ala Glu Trp Arg Gly Arg Glu Arg Ser Gly Ser Ala
                180                 185                 190

Arg Ala Gln Arg
            195

<210> SEQ ID NO 61
<211> LENGTH: 12
<212> TYPE: PRT
<213> ORGANISM: artificial sequence
<220> FEATURE:
<223> OTHER INFORMATION: epitope

<400> SEQUENCE: 61

Leu Pro Ala His Gly Gln Leu Asp Thr Val Pro Phe
1               5                   10

<210> SEQ ID NO 62
<211> LENGTH: 12
<212> TYPE: PRT
<213> ORGANISM: artificial sequence
<220> FEATURE:
<223> OTHER INFORMATION: epitope

<400> SEQUENCE: 62

Leu Ser Asp Pro Ala Ala Leu Glu Arg Leu Leu Asp
1               5                   10
```

```
<210> SEQ ID NO 63
<211> LENGTH: 12
<212> TYPE: PRT
<213> ORGANISM: artificial sequence
<220> FEATURE:
<223> OTHER INFORMATION: epitope

<400> SEQUENCE: 63

Glu Arg Leu Leu Asp Gly Glu Glu Pro Leu Leu Leu
1               5                   10

<210> SEQ ID NO 64
<211> LENGTH: 12
<212> TYPE: PRT
<213> ORGANISM: artificial sequence
<220> FEATURE:
<223> OTHER INFORMATION: epitope

<400> SEQUENCE: 64

Glu Pro Leu Leu Leu Leu Leu Arg Pro Thr Ala Ala
1               5                   10

<210> SEQ ID NO 65
<211> LENGTH: 12
<212> TYPE: PRT
<213> ORGANISM: artificial sequence
<220> FEATURE:
<223> OTHER INFORMATION: epitope

<400> SEQUENCE: 65

Gly Asp Pro Ala Pro Leu His Asp Pro Thr Ser Ala
1               5                   10

<210> SEQ ID NO 66
<211> LENGTH: 12
<212> TYPE: PRT
<213> ORGANISM: artificial sequence
<220> FEATURE:
<223> OTHER INFORMATION: epitope

<400> SEQUENCE: 66

Asp Pro Thr Ser Ala Pro Trp Ala Thr Ala Leu Ala
1               5                   10

<210> SEQ ID NO 67
<211> LENGTH: 12
<212> TYPE: PRT
<213> ORGANISM: artificial sequence
<220> FEATURE:
<223> OTHER INFORMATION: epitope

<400> SEQUENCE: 67

Leu Lys Ala Leu Gln Gly Leu Arg Val Glu Trp Arg
1               5                   10

<210> SEQ ID NO 68
<211> LENGTH: 12
<212> TYPE: PRT
<213> ORGANISM: artificial sequence
<220> FEATURE:
<223> OTHER INFORMATION: epitope

<400> SEQUENCE: 68

Arg Val Glu Trp Arg Gly Arg Asp Pro Arg Gly Pro
1               5                   10
```

```
<210> SEQ ID NO 69
<211> LENGTH: 12
<212> TYPE: PRT
<213> ORGANISM: artificial sequence
<220> FEATURE:
<223> OTHER INFORMATION: epitope

<400> SEQUENCE: 69

Met Pro Ala His Gly Arg Leu Asp Thr Val Pro Phe
1               5                   10

<210> SEQ ID NO 70
<211> LENGTH: 12
<212> TYPE: PRT
<213> ORGANISM: artificial sequence
<220> FEATURE:
<223> OTHER INFORMATION: epitope

<400> SEQUENCE: 70

Glu Pro Leu Leu Leu Leu Pro Pro Thr Ala Ala
1               5                   10

<210> SEQ ID NO 71
<211> LENGTH: 12
<212> TYPE: PRT
<213> ORGANISM: artificial sequence
<220> FEATURE:
<223> OTHER INFORMATION: epitope

<400> SEQUENCE: 71

Gly Asp Pro Ala Pro Leu Pro Asp Pro Ala Ser Ala
1               5                   10

<210> SEQ ID NO 72
<211> LENGTH: 12
<212> TYPE: PRT
<213> ORGANISM: artificial sequence
<220> FEATURE:
<223> OTHER INFORMATION: epitope

<400> SEQUENCE: 72

Asp Pro Ala Ser Ala Pro Trp Ala Ala Gly Leu Ala
1               5                   10

<210> SEQ ID NO 73
<211> LENGTH: 12
<212> TYPE: PRT
<213> ORGANISM: artificial sequence
<220> FEATURE:
<223> OTHER INFORMATION: epitope

<400> SEQUENCE: 73

Leu Lys Ala Leu Gln Gly Leu Arg Ala Glu Trp Arg
1               5                   10

<210> SEQ ID NO 74
<211> LENGTH: 12
<212> TYPE: PRT
<213> ORGANISM: artificial sequence
<220> FEATURE:
<223> OTHER INFORMATION: epitope

<400> SEQUENCE: 74

Arg Ala Glu Trp Arg Gly Arg Glu Arg Ser Gly Pro
1               5                   10

<210> SEQ ID NO 75
```

```
<211> LENGTH: 12
<212> TYPE: PRT
<213> ORGANISM: artificial sequence
<220> FEATURE:
<223> OTHER INFORMATION: epitope

<400> SEQUENCE: 75

Val Pro Ala Arg Gly Leu Leu Asp Leu Val Pro Phe
1               5                   10

<210> SEQ ID NO 76
<211> LENGTH: 12
<212> TYPE: PRT
<213> ORGANISM: artificial sequence
<220> FEATURE:
<223> OTHER INFORMATION: epitope

<400> SEQUENCE: 76

Leu Ser Asp Pro Ala Thr Gln Glu Arg Leu Leu Gly
1               5                   10

<210> SEQ ID NO 77
<211> LENGTH: 12
<212> TYPE: PRT
<213> ORGANISM: artificial sequence
<220> FEATURE:
<223> OTHER INFORMATION: epitope

<400> SEQUENCE: 77

Glu Arg Leu Leu Gly Gly Glu Glu Pro Leu Leu Leu
1               5                   10

<210> SEQ ID NO 78
<211> LENGTH: 13
<212> TYPE: PRT
<213> ORGANISM: artificial sequence
<220> FEATURE:
<223> OTHER INFORMATION: epitope

<400> SEQUENCE: 78

Glu Pro Leu Leu Leu Leu Leu Pro Pro Pro Thr Ala Ala
1               5                   10

<210> SEQ ID NO 79
<211> LENGTH: 12
<212> TYPE: PRT
<213> ORGANISM: artificial sequence
<220> FEATURE:
<223> OTHER INFORMATION: epitope

<400> SEQUENCE: 79

Gly Pro Pro Ala Pro Pro Pro Arg Pro Ala Ser Ala
1               5                   10

<210> SEQ ID NO 80
<211> LENGTH: 12
<212> TYPE: PRT
<213> ORGANISM: artificial sequence
<220> FEATURE:
<223> OTHER INFORMATION: epitope

<400> SEQUENCE: 80

Arg Pro Ala Ser Ala Pro Trp Ala Ala Gly Leu Ala
1               5                   10

<210> SEQ ID NO 81
<211> LENGTH: 12
```

```
<212> TYPE: PRT
<213> ORGANISM: artificial sequence
<220> FEATURE:
<223> OTHER INFORMATION: epitope

<400> SEQUENCE: 81

Arg Ala Glu Trp Arg Gly Arg Glu Arg Gly Gly Pro
1               5                   10

<210> SEQ ID NO 82
<211> LENGTH: 12
<212> TYPE: PRT
<213> ORGANISM: artificial sequence
<220> FEATURE:
<223> OTHER INFORMATION: epitope

<400> SEQUENCE: 82

Met Pro Ala His Gly Arg Leu Asp Leu Val Pro Phe
1               5                   10

<210> SEQ ID NO 83
<211> LENGTH: 12
<212> TYPE: PRT
<213> ORGANISM: artificial sequence
<220> FEATURE:
<223> OTHER INFORMATION: epitope

<400> SEQUENCE: 83

Gly Val Pro Ala Thr Pro Gln Gly Pro Lys Ser Pro
1               5                   10

<210> SEQ ID NO 84
<211> LENGTH: 12
<212> TYPE: PRT
<213> ORGANISM: artificial sequence
<220> FEATURE:
<223> OTHER INFORMATION: epitope

<400> SEQUENCE: 84

Gly Pro Lys Ser Pro Leu Trp Ala Ala Gly Leu Ala
1               5                   10

<210> SEQ ID NO 85
<211> LENGTH: 12
<212> TYPE: PRT
<213> ORGANISM: artificial sequence
<220> FEATURE:
<223> OTHER INFORMATION: epitope

<400> SEQUENCE: 85

Arg Ala Glu Trp Arg Gly Arg Glu Arg Ser Gly Ser
1               5                   10

<210> SEQ ID NO 86
<211> LENGTH: 468
<212> TYPE: DNA
<213> ORGANISM: artificial sequence
<220> FEATURE:
<223> OTHER INFORMATION: polynucleotide

<400> SEQUENCE: 86
atgcgggacc tgcccctgac aagcctggct ctggtgctgt ctgctctggg agccctcctg     60
ggaacagaag ccctgagagc cgaagaacct gccgtgggca catccggcct gatcttcaga    120
gaggacctgg actggcctcc cggcagccct caggaacctc tctgtctggt cgctctgggc    180
ggcgacagca atggctctag cagccctctg agagtcgtgg gcgccctgtc tgcctacgag    240
```

| | |
|---|---|
| caggcttttc tgggagccgt gcagagggct agatggggcc ctagagatct ggccaccttc | 300 |
| ggcgtgtgca acaccggcga tagacaggcc gctctgccca gcctgagaag gctgggagct | 360 |
| tggctgagag atcctggcgg ccagagactg gtggtgctgc acctggaaga agtgacctgg | 420 |
| gagcctaccc ctagcctgcg gtttcaggaa ccacctcctg gcggagcc | 468 |

<210> SEQ ID NO 87
<211> LENGTH: 765
<212> TYPE: DNA
<213> ORGANISM: artificial sequence
<220> FEATURE:
<223> OTHER INFORMATION: polynucleotide

<400> SEQUENCE: 87

| | |
|---|---|
| atgcgggacc tgcccctgac aagcctggct ctggtgctgt ctgctctggg agccctcctg | 60 |
| ggaacagaag ccctgagagc cgaagaacct gccgtgggca catccggcct gatcttcaga | 120 |
| gaggacctgg actggcctcc cggcagccct caggaacctc tctgtctggt cgctctgggc | 180 |
| ggcgacagca atggctctag cagccctctg agagtcgtgg gcgccctgtc tgcctacgag | 240 |
| caggcttttc tgggagccgt gcagagggct agatggggcc ctagagatct ggccaccttc | 300 |
| ggcgtgtgca acaccggcga tagacaggcc gctctgccca gcctgagaag gctgggagct | 360 |
| tggctgagag atcctggcgg ccagagactg gtggtgctgc acctggaaga agtgacctgg | 420 |
| gagcctaccc ctagcctgcg gtttcaggaa ccacctcctg gcggagccgg acctcctgaa | 480 |
| ctggctctgc tggtcctgta tcctggccct ggccccgaag tgaccgtgac aagagctgga | 540 |
| ctgcctggcg cccagtccct gtgccctagc agagacacca gataccttggt gctggccgtg | 600 |
| gacagacctg ccggcgcttg gagaggaagt ggcctggcac tgaccctgca gcccagaggc | 660 |
| gaggatagca gactgagcac cgccagactg caggccctgc tgtttggcga cgaccaccgg | 720 |
| tgcttcacca gaatgacccc ctgccctgctg ctgctcccca gatct | 765 |

<210> SEQ ID NO 88
<211> LENGTH: 1353
<212> TYPE: DNA
<213> ORGANISM: artificial sequence
<220> FEATURE:
<223> OTHER INFORMATION: polynucleotide

<400> SEQUENCE: 88

| | |
|---|---|
| atgcgggacc tgcccctgac aagcctggct ctggtgctgt ctgctctggg agccctcctg | 60 |
| ggaacagaag ccctgagagc cgaagaacct gccgtgggca catccggcct gatcttcaga | 120 |
| gaggacctgg actggcctcc cggcagccct caggaacctc tctgtctggt cgctctgggc | 180 |
| ggcgacagca atggctctag cagccctctg agagtcgtgg gcgccctgtc tgcctacgag | 240 |
| caggcttttc tgggagccgt gcagagggct agatggggcc ctagagatct ggccaccttc | 300 |
| ggcgtgtgca acaccggcga tagacaggcc gctctgccca gcctgagaag gctgggagct | 360 |
| tggctgagag atcctggcgg ccagagactg gtggtgctgc acctggaaga agtgacctgg | 420 |
| gagcctaccc ctagcctgcg gtttcaggaa ccacctcctg gcggagccgg acctcctgaa | 480 |
| ctggctctgc tggtcctgta tcctggccct ggccccgaag tgaccgtgac aagagctgga | 540 |
| ctgcctggcg cccagtccct gtgccctagc agagacacca gataccttggt gctggccgtg | 600 |
| gacagacctg ccggcgcttg gagaggaagt ggcctggcac tgaccctgca gcccagaggc | 660 |
| gaggatagca gactgagcac cgccagactg caggccctgc tgtttggcga cgaccaccgg | 720 |

-continued

| | |
|---|---|
| tgcttcacca gaatgacccc tgccctgctg ctgctcccca gatctgaacc tgctcctctg | 780 |
| cctgcccacg gacagctgga taccgtgcct ttcccaccac ctagacccag cgccgagctg | 840 |
| gaagagtctc ctcctagcgc cgacccttc ctggaaaccc tgactagact cgtgcgggcc | 900 |
| ctgagggtgc caccagctag agcatctgcc cctagactgg cactggatcc cgatgccctg | 960 |
| gccggctttc ctcagggact cgtgaacctg tctgacccag ccgctctgga aagactgctg | 1020 |
| gacggcgaag aaccactcct cctgctgctc agacctaccg ccgccacaac aggcgatcct | 1080 |
| gcccctctgc atgatcccac atctgctcca tgggccaccg ccctggctag aagagtggct | 1140 |
| gctgaactgc aggctgccgc cgctgagctg agatctctgc caggactgcc tcctgccaca | 1200 |
| gccccactgc tggctagact gctcgctctg tgtccaggcg gacctggcgg actgggagat | 1260 |
| ccactgagag cactgctgct cctcaaggcc ctccagggcc tcagggtcga atggcgggga | 1320 |
| agagatccta gaggcccagg cagagcccag aga | 1353 |

<210> SEQ ID NO 89
<211> LENGTH: 1679
<212> TYPE: DNA
<213> ORGANISM: artificial sequence
<220> FEATURE:
<223> OTHER INFORMATION: polynucleotide

<400> SEQUENCE: 89

| | |
|---|---|
| atgcgggacc tgcccctgac aagcctggct ctggtgctgt ctgctctggg agccctcctg | 60 |
| ggaacagaag ccctgagagc cgaagaacct gccgtgggca catccggcct gatcttcaga | 120 |
| gaggacctgg actggcctcc cggcagccct caggaacctc tctgtctggt cgctctgggc | 180 |
| ggcgacagca atggctctag cagccctctg agagtcgtgg gcgccctgtc tgcctacgag | 240 |
| caggcttttc tgggagccgt gcagagggct agatggggcc ctagagatct ggccaccttc | 300 |
| ggcgtgtgca acaccggcga tagacaggcc gctctgccca gcctgagaag gctgggagct | 360 |
| tggctgagag atcctggcgg ccagagactg gtggtgctgc acctggaaga agtgacctgg | 420 |
| gagcctaccc ctagcctgcg gtttcaggaa ccacctcctg gcggagccgg acctcctgaa | 480 |
| ctggctctgc tggtcctgta tcctggccct ggccccgaag tgaccgtgac aagagctgga | 540 |
| ctgcctggcg cccagtccct gtgccctagc agagacacca gataccctgg gctggccgtg | 600 |
| gacagacctg ccggcgcttg gagaggaagt ggcctggcac tgaccctgca gcccagaggc | 660 |
| gaggatagca gactgagcac cgccagactg caggccctgc tgtttggcga cgaccaccgg | 720 |
| tgcttcacca gaatgacccc tgccctgctg ctgctcccca gatctgaacc tgctcctctg | 780 |
| cctgcccacg gacagctgga taccgtgcct ttcccaccac ctagacccag cgccgagctg | 840 |
| gaagagtctc ctcctagcgc cgacccttc ctggaaaccc tgactagact cgtgcgggcc | 900 |
| ctgagggtgc caccagctag agcatctgcc cctagactgg cactggatcc cgatgccctg | 960 |
| gccggctttc ctcagggact cgtgaacctg tctgacccag ccgctctgga aagactgctg | 1020 |
| gacggcgaag aaccactcct cctgctgctc agacctaccg ccgccacaac aggcgatcct | 1080 |
| gcccctctgc atgatcccac atctgctcca tgggccaccg ccctggctag aagagtggct | 1140 |
| gctgaactgc aggctgccgc cgctgagctg agatctctgc caggactgcc tcctgccaca | 1200 |
| gccccactgc tggctagact gctcgctctg tgtccaggcg gacctggcgg actgggagat | 1260 |
| ccactgagag cactgctgct cctcaaggcc ctccagggcc tcagggtcga atggcgggga | 1320 |
| agagatccta gaggcccagg cagagcccag agaagcgctg cgctacagc tgccgatgga | 1380 |
| ccttgcgctc tgcgggaact gagcgtggac ctgagggccg agagaagcgt cctgatcccc | 1440 |

```
gagacatacc aggccaacaa ctgccagggc gtgtgcggct ggcctcagag cgacagaaac   1500
cccagatacg gcaatcacgt ggtgctgctg ctgaagatgc aagtccgagg cgccgctctg   1560
gcaagacctc cttgttgtgt gcctaccgcc tacgccggca agctgctgat ctccctgagc   1620
gaggaacgga tagcgcccac cacgtgccca acatggtggc cacagagtgc ggctgccgg    1679
```

<210> SEQ ID NO 90
<211> LENGTH: 12
<212> TYPE: PRT
<213> ORGANISM: artificial sequence
<220> FEATURE:
<223> OTHER INFORMATION: peptide

<400> SEQUENCE: 90

Met Arg Asp Leu Pro Leu Thr Ser Leu Ala Leu Val
1               5                   10

<210> SEQ ID NO 91
<211> LENGTH: 12
<212> TYPE: PRT
<213> ORGANISM: artificial sequence
<220> FEATURE:
<223> OTHER INFORMATION: peptide

<400> SEQUENCE: 91

Ser Leu Ala Leu Val Leu Ser Ala Leu Gly Ala Leu
1               5                   10

<210> SEQ ID NO 92
<211> LENGTH: 12
<212> TYPE: PRT
<213> ORGANISM: artificial sequence
<220> FEATURE:
<223> OTHER INFORMATION: peptide

<400> SEQUENCE: 92

Ala Leu Gly Ala Leu Leu Gly Thr Glu Ala Leu Arg
1               5                   10

<210> SEQ ID NO 93
<211> LENGTH: 12
<212> TYPE: PRT
<213> ORGANISM: artificial sequence
<220> FEATURE:
<223> OTHER INFORMATION: peptide

<400> SEQUENCE: 93

Thr Glu Ala Leu Arg Ala Glu Glu Pro Ala Val Gly
1               5                   10

<210> SEQ ID NO 94
<211> LENGTH: 12
<212> TYPE: PRT
<213> ORGANISM: artificial sequence
<220> FEATURE:
<223> OTHER INFORMATION: peptide

<400> SEQUENCE: 94

Glu Pro Ala Val Gly Thr Ser Gly Leu Ile Phe Arg
1               5                   10

<210> SEQ ID NO 95
<211> LENGTH: 12
<212> TYPE: PRT
<213> ORGANISM: artificial sequence

```
<220> FEATURE:
<223> OTHER INFORMATION: peptide

<400> SEQUENCE: 95

Gly Leu Ile Phe Arg Glu Asp Leu Asp Trp Pro Pro
1               5                   10

<210> SEQ ID NO 96
<211> LENGTH: 12
<212> TYPE: PRT
<213> ORGANISM: artificial sequence
<220> FEATURE:
<223> OTHER INFORMATION: peptide

<400> SEQUENCE: 96

Leu Asp Trp Pro Pro Gly Ser Pro Gln Glu Pro Leu
1               5                   10

<210> SEQ ID NO 97
<211> LENGTH: 12
<212> TYPE: PRT
<213> ORGANISM: artificial sequence
<220> FEATURE:
<223> OTHER INFORMATION: peptide

<400> SEQUENCE: 97

Pro Gln Glu Pro Leu Cys Leu Val Ala Leu Gly Gly
1               5                   10

<210> SEQ ID NO 98
<211> LENGTH: 12
<212> TYPE: PRT
<213> ORGANISM: artificial sequence
<220> FEATURE:
<223> OTHER INFORMATION: peptide

<400> SEQUENCE: 98

Val Ala Leu Gly Gly Asp Ser Asn Gly Ser Ser Ser
1               5                   10

<210> SEQ ID NO 99
<211> LENGTH: 12
<212> TYPE: PRT
<213> ORGANISM: artificial sequence
<220> FEATURE:
<223> OTHER INFORMATION: peptide

<400> SEQUENCE: 99

Asn Gly Ser Ser Ser Pro Leu Arg Val Val Gly Ala
1               5                   10

<210> SEQ ID NO 100
<211> LENGTH: 12
<212> TYPE: PRT
<213> ORGANISM: artificial sequence
<220> FEATURE:
<223> OTHER INFORMATION: peptide

<400> SEQUENCE: 100

Arg Val Val Gly Ala Leu Ser Ala Tyr Glu Gln Ala
1               5                   10

<210> SEQ ID NO 101
<211> LENGTH: 12
<212> TYPE: PRT
<213> ORGANISM: artificial sequence
<220> FEATURE:
```

<223> OTHER INFORMATION: peptide

<400> SEQUENCE: 101

Ala Tyr Glu Gln Ala Phe Leu Gly Ala Val Gln Arg
1               5                   10

<210> SEQ ID NO 102
<211> LENGTH: 12
<212> TYPE: PRT
<213> ORGANISM: artificial sequence
<220> FEATURE:
<223> OTHER INFORMATION: peptide

<400> SEQUENCE: 102

Gly Ala Val Gln Arg Ala Arg Trp Gly Pro Arg Asp
1               5                   10

<210> SEQ ID NO 103
<211> LENGTH: 12
<212> TYPE: PRT
<213> ORGANISM: artificial sequence
<220> FEATURE:
<223> OTHER INFORMATION: peptide

<400> SEQUENCE: 103

Trp Gly Pro Arg Asp Leu Ala Thr Phe Gly Val Cys
1               5                   10

<210> SEQ ID NO 104
<211> LENGTH: 12
<212> TYPE: PRT
<213> ORGANISM: artificial sequence
<220> FEATURE:
<223> OTHER INFORMATION: peptide

<400> SEQUENCE: 104

Thr Phe Gly Val Cys Asn Thr Gly Asp Arg Gln Ala
1               5                   10

<210> SEQ ID NO 105
<211> LENGTH: 12
<212> TYPE: PRT
<213> ORGANISM: artificial sequence
<220> FEATURE:
<223> OTHER INFORMATION: peptide

<400> SEQUENCE: 105

Gly Asp Arg Gln Ala Ala Leu Pro Ser Leu Arg Arg
1               5                   10

<210> SEQ ID NO 106
<211> LENGTH: 12
<212> TYPE: PRT
<213> ORGANISM: artificial sequence
<220> FEATURE:
<223> OTHER INFORMATION: peptide

<400> SEQUENCE: 106

Pro Ser Leu Arg Arg Leu Gly Ala Trp Leu Arg Asp
1               5                   10

<210> SEQ ID NO 107
<211> LENGTH: 12
<212> TYPE: PRT
<213> ORGANISM: artificial sequence
<220> FEATURE:
<223> OTHER INFORMATION: peptide

```
<400> SEQUENCE: 107

Ala Trp Leu Arg Asp Pro Gly Gly Gln Arg Leu Val
1               5                   10

<210> SEQ ID NO 108
<211> LENGTH: 12
<212> TYPE: PRT
<213> ORGANISM: artificial sequence
<220> FEATURE:
<223> OTHER INFORMATION: peptide

<400> SEQUENCE: 108

Gly Gln Arg Leu Val Val Leu His Leu Glu Glu Val
1               5                   10

<210> SEQ ID NO 109
<211> LENGTH: 12
<212> TYPE: PRT
<213> ORGANISM: artificial sequence
<220> FEATURE:
<223> OTHER INFORMATION: peptide

<400> SEQUENCE: 109

His Leu Glu Glu Val Thr Trp Glu Pro Thr Pro Ser
1               5                   10

<210> SEQ ID NO 110
<211> LENGTH: 12
<212> TYPE: PRT
<213> ORGANISM: artificial sequence
<220> FEATURE:
<223> OTHER INFORMATION: peptide

<400> SEQUENCE: 110

Glu Pro Thr Pro Ser Leu Arg Phe Gln Glu Pro Pro
1               5                   10

<210> SEQ ID NO 111
<211> LENGTH: 12
<212> TYPE: PRT
<213> ORGANISM: artificial sequence
<220> FEATURE:
<223> OTHER INFORMATION: peptide

<400> SEQUENCE: 111

Phe Gln Glu Pro Pro Pro Gly Gly Ala Gly Pro Pro
1               5                   10

<210> SEQ ID NO 112
<211> LENGTH: 12
<212> TYPE: PRT
<213> ORGANISM: artificial sequence
<220> FEATURE:
<223> OTHER INFORMATION: peptide

<400> SEQUENCE: 112

Gly Ala Gly Pro Pro Glu Leu Ala Leu Leu Val Leu
1               5                   10

<210> SEQ ID NO 113
<211> LENGTH: 12
<212> TYPE: PRT
<213> ORGANISM: artificial sequence
<220> FEATURE:
<223> OTHER INFORMATION: peptide
```

<400> SEQUENCE: 113

Ala Leu Leu Val Leu Tyr Pro Gly Pro Gly Pro Glu
1               5                   10

<210> SEQ ID NO 114
<211> LENGTH: 12
<212> TYPE: PRT
<213> ORGANISM: artificial sequence
<220> FEATURE:
<223> OTHER INFORMATION: peptide

<400> SEQUENCE: 114

Gly Pro Gly Pro Glu Val Thr Val Thr Arg Ala Gly
1               5                   10

<210> SEQ ID NO 115
<211> LENGTH: 12
<212> TYPE: PRT
<213> ORGANISM: artificial sequence
<220> FEATURE:
<223> OTHER INFORMATION: peptide

<400> SEQUENCE: 115

Val Thr Arg Ala Gly Leu Pro Gly Ala Gln Ser Leu
1               5                   10

<210> SEQ ID NO 116
<211> LENGTH: 12
<212> TYPE: PRT
<213> ORGANISM: artificial sequence
<220> FEATURE:
<223> OTHER INFORMATION: peptide

<400> SEQUENCE: 116

Gly Ala Gln Ser Leu Cys Pro Ser Arg Asp Thr Arg
1               5                   10

<210> SEQ ID NO 117
<211> LENGTH: 12
<212> TYPE: PRT
<213> ORGANISM: artificial sequence
<220> FEATURE:
<223> OTHER INFORMATION: peptide

<400> SEQUENCE: 117

Ser Arg Asp Thr Arg Tyr Leu Val Leu Ala Val Asp
1               5                   10

<210> SEQ ID NO 118
<211> LENGTH: 12
<212> TYPE: PRT
<213> ORGANISM: artificial sequence
<220> FEATURE:
<223> OTHER INFORMATION: peptide

<400> SEQUENCE: 118

Ala Gly Ala Trp Arg Gly Ser Gly Leu Ala Leu Thr
1               5                   10

<210> SEQ ID NO 119
<211> LENGTH: 12
<212> TYPE: PRT
<213> ORGANISM: artificial sequence
<220> FEATURE:
<223> OTHER INFORMATION: peptide

<400> SEQUENCE: 119

```
Gly Leu Ala Leu Thr Leu Gln Pro Arg Gly Glu Asp
1               5                   10
```

<210> SEQ ID NO 120
<211> LENGTH: 12
<212> TYPE: PRT
<213> ORGANISM: artificial sequence
<220> FEATURE:
<223> OTHER INFORMATION: peptide

<400> SEQUENCE: 120

```
Leu Ser Thr Ala Arg Leu Gln Ala Leu Leu Phe Gly
1               5                   10
```

<210> SEQ ID NO 121
<211> LENGTH: 12
<212> TYPE: PRT
<213> ORGANISM: artificial sequence
<220> FEATURE:
<223> OTHER INFORMATION: peptide

<400> SEQUENCE: 121

```
Ala Leu Leu Phe Gly Asp Asp His Arg Cys Phe Thr
1               5                   10
```

<210> SEQ ID NO 122
<211> LENGTH: 12
<212> TYPE: PRT
<213> ORGANISM: artificial sequence
<220> FEATURE:
<223> OTHER INFORMATION: peptide

<400> SEQUENCE: 122

```
Thr Pro Ala Leu Leu Leu Leu Pro Arg Ser Glu Pro
1               5                   10
```

<210> SEQ ID NO 123
<211> LENGTH: 12
<212> TYPE: PRT
<213> ORGANISM: artificial sequence
<220> FEATURE:
<223> OTHER INFORMATION: peptide

<400> SEQUENCE: 123

```
Pro Arg Ser Glu Pro Ala Pro Leu Pro Ala His Gly
1               5                   10
```

<210> SEQ ID NO 124
<211> LENGTH: 12
<212> TYPE: PRT
<213> ORGANISM: artificial sequence
<220> FEATURE:
<223> OTHER INFORMATION: peptide

<400> SEQUENCE: 124

```
Asp Thr Val Pro Phe Pro Pro Pro Arg Pro Ser Ala
1               5                   10
```

<210> SEQ ID NO 125
<211> LENGTH: 12
<212> TYPE: PRT
<213> ORGANISM: artificial sequence
<220> FEATURE:
<223> OTHER INFORMATION: peptide

<400> SEQUENCE: 125

Pro Arg Pro Ser Ala Glu Leu Glu Glu Ser Pro Pro
1               5                   10

<210> SEQ ID NO 126
<211> LENGTH: 12
<212> TYPE: PRT
<213> ORGANISM: artificial sequence
<220> FEATURE:
<223> OTHER INFORMATION: peptide

<400> SEQUENCE: 126

Glu Glu Ser Pro Pro Ser Ala Asp Pro Phe Leu Glu
1               5                   10

<210> SEQ ID NO 127
<211> LENGTH: 12
<212> TYPE: PRT
<213> ORGANISM: artificial sequence
<220> FEATURE:
<223> OTHER INFORMATION: peptide

<400> SEQUENCE: 127

Asp Pro Phe Leu Glu Thr Leu Thr Arg Leu Val Arg
1               5                   10

<210> SEQ ID NO 128
<211> LENGTH: 12
<212> TYPE: PRT
<213> ORGANISM: artificial sequence
<220> FEATURE:
<223> OTHER INFORMATION: peptide

<400> SEQUENCE: 128

Thr Arg Leu Val Arg Ala Leu Arg Val Pro Pro Ala
1               5                   10

<210> SEQ ID NO 129
<211> LENGTH: 12
<212> TYPE: PRT
<213> ORGANISM: artificial sequence
<220> FEATURE:
<223> OTHER INFORMATION: peptide

<400> SEQUENCE: 129

Arg Val Pro Pro Ala Arg Ala Ser Ala Pro Arg Leu
1               5                   10

<210> SEQ ID NO 130
<211> LENGTH: 12
<212> TYPE: PRT
<213> ORGANISM: artificial sequence
<220> FEATURE:
<223> OTHER INFORMATION: peptide

<400> SEQUENCE: 130

Ser Ala Pro Arg Leu Ala Leu Asp Pro Asp Ala Leu
1               5                   10

<210> SEQ ID NO 131
<211> LENGTH: 12
<212> TYPE: PRT
<213> ORGANISM: artificial sequence
<220> FEATURE:
<223> OTHER INFORMATION: peptide

<400> SEQUENCE: 131

Asp Pro Asp Ala Leu Ala Gly Phe Pro Gln Gly Leu

```
1               5                   10
```

<210> SEQ ID NO 132
<211> LENGTH: 12
<212> TYPE: PRT
<213> ORGANISM: artificial sequence
<220> FEATURE:
<223> OTHER INFORMATION: peptide

<400> SEQUENCE: 132

```
Phe Pro Gln Gly Leu Val Asn Leu Ser Asp Pro Ala
1               5                   10
```

<210> SEQ ID NO 133
<211> LENGTH: 12
<212> TYPE: PRT
<213> ORGANISM: artificial sequence
<220> FEATURE:
<223> OTHER INFORMATION: peptide

<400> SEQUENCE: 133

```
Arg Pro Thr Ala Ala Thr Thr Gly Asp Pro Ala Pro
1               5                   10
```

<210> SEQ ID NO 134
<211> LENGTH: 12
<212> TYPE: PRT
<213> ORGANISM: artificial sequence
<220> FEATURE:
<223> OTHER INFORMATION: peptide

<400> SEQUENCE: 134

```
Ala Thr Ala Leu Ala Arg Arg Val Ala Ala Glu Leu
1               5                   10
```

<210> SEQ ID NO 135
<211> LENGTH: 12
<212> TYPE: PRT
<213> ORGANISM: artificial sequence
<220> FEATURE:
<223> OTHER INFORMATION: peptide

<400> SEQUENCE: 135

```
Val Ala Ala Glu Leu Gln Ala Ala Ala Ala Glu Leu
1               5                   10
```

<210> SEQ ID NO 136
<211> LENGTH: 12
<212> TYPE: PRT
<213> ORGANISM: artificial sequence
<220> FEATURE:
<223> OTHER INFORMATION: peptide

<400> SEQUENCE: 136

```
Ala Ala Ala Glu Leu Arg Ser Leu Pro Gly Leu Pro
1               5                   10
```

<210> SEQ ID NO 137
<211> LENGTH: 12
<212> TYPE: PRT
<213> ORGANISM: artificial sequence
<220> FEATURE:
<223> OTHER INFORMATION: peptide

<400> SEQUENCE: 137

```
Leu Pro Gly Leu Pro Pro Ala Thr Ala Pro Leu Leu
1               5                   10
```

```
<210> SEQ ID NO 138
<211> LENGTH: 12
<212> TYPE: PRT
<213> ORGANISM: artificial sequence
<220> FEATURE:
<223> OTHER INFORMATION: peptide

<400> SEQUENCE: 138

Thr Ala Pro Leu Leu Ala Arg Leu Leu Ala Leu Cys
1               5                   10

<210> SEQ ID NO 139
<211> LENGTH: 12
<212> TYPE: PRT
<213> ORGANISM: artificial sequence
<220> FEATURE:
<223> OTHER INFORMATION: peptide

<400> SEQUENCE: 139

Leu Leu Ala Leu Cys Pro Gly Gly Pro Gly Gly Leu
1               5                   10

<210> SEQ ID NO 140
<211> LENGTH: 12
<212> TYPE: PRT
<213> ORGANISM: artificial sequence
<220> FEATURE:
<223> OTHER INFORMATION: peptide

<400> SEQUENCE: 140

Gly Pro Gly Gly Leu Gly Asp Pro Leu Arg Ala Leu
1               5                   10

<210> SEQ ID NO 141
<211> LENGTH: 12
<212> TYPE: PRT
<213> ORGANISM: artificial sequence
<220> FEATURE:
<223> OTHER INFORMATION: peptide

<400> SEQUENCE: 141

Pro Leu Arg Ala Leu Leu Leu Lys Ala Leu Gln
1               5                   10

<210> SEQ ID NO 142
<211> LENGTH: 12
<212> TYPE: PRT
<213> ORGANISM: artificial sequence
<220> FEATURE:
<223> OTHER INFORMATION: peptide

<400> SEQUENCE: 142

Asp Pro Arg Gly Pro Gly Arg Ala Gln Arg Ser Ala
1               5                   10

<210> SEQ ID NO 143
<211> LENGTH: 12
<212> TYPE: PRT
<213> ORGANISM: artificial sequence
<220> FEATURE:
<223> OTHER INFORMATION: peptide

<400> SEQUENCE: 143

Ala Gln Arg Ser Ala Gly Ala Thr Ala Ala Asp Gly
1               5                   10
```

```
<210> SEQ ID NO 144
<211> LENGTH: 12
<212> TYPE: PRT
<213> ORGANISM: artificial sequence
<220> FEATURE:
<223> OTHER INFORMATION: peptide

<400> SEQUENCE: 144

Thr Ala Ala Asp Gly Pro Cys Ala Leu Arg Glu Leu
1               5                   10

<210> SEQ ID NO 145
<211> LENGTH: 12
<212> TYPE: PRT
<213> ORGANISM: artificial sequence
<220> FEATURE:
<223> OTHER INFORMATION: peptide

<400> SEQUENCE: 145

Ala Leu Arg Glu Leu Ser Val Asp Leu Arg Ala Glu
1               5                   10

<210> SEQ ID NO 146
<211> LENGTH: 12
<212> TYPE: PRT
<213> ORGANISM: artificial sequence
<220> FEATURE:
<223> OTHER INFORMATION: peptide

<400> SEQUENCE: 146

Asp Leu Arg Ala Glu Arg Ser Val Leu Ile Pro Glu
1               5                   10

<210> SEQ ID NO 147
<211> LENGTH: 12
<212> TYPE: PRT
<213> ORGANISM: artificial sequence
<220> FEATURE:
<223> OTHER INFORMATION: peptide

<400> SEQUENCE: 147

Val Leu Ile Pro Glu Thr Tyr Gln Ala Asn Asn Cys
1               5                   10

<210> SEQ ID NO 148
<211> LENGTH: 12
<212> TYPE: PRT
<213> ORGANISM: artificial sequence
<220> FEATURE:
<223> OTHER INFORMATION: peptide

<400> SEQUENCE: 148

Gln Ala Asn Asn Cys Gln Gly Val Cys Gly Trp Pro
1               5                   10

<210> SEQ ID NO 149
<211> LENGTH: 12
<212> TYPE: PRT
<213> ORGANISM: artificial sequence
<220> FEATURE:
<223> OTHER INFORMATION: peptide

<400> SEQUENCE: 149

Val Cys Gly Trp Pro Gln Ser Asp Arg Asn Pro Arg
1               5                   10
```

```
<210> SEQ ID NO 150
<211> LENGTH: 12
<212> TYPE: PRT
<213> ORGANISM: artificial sequence
<220> FEATURE:
<223> OTHER INFORMATION: peptide

<400> SEQUENCE: 150

Asp Arg Asn Pro Arg Tyr Gly Asn His Val Val Leu
1               5                   10

<210> SEQ ID NO 151
<211> LENGTH: 12
<212> TYPE: PRT
<213> ORGANISM: artificial sequence
<220> FEATURE:
<223> OTHER INFORMATION: peptide

<400> SEQUENCE: 151

Asn His Val Val Leu Leu Leu Lys Met Gln Val Arg
1               5                   10

<210> SEQ ID NO 152
<211> LENGTH: 12
<212> TYPE: PRT
<213> ORGANISM: artificial sequence
<220> FEATURE:
<223> OTHER INFORMATION: peptide

<400> SEQUENCE: 152

Lys Met Gln Val Arg Gly Ala Ala Leu Ala Arg Pro
1               5                   10

<210> SEQ ID NO 153
<211> LENGTH: 12
<212> TYPE: PRT
<213> ORGANISM: artificial sequence
<220> FEATURE:
<223> OTHER INFORMATION: peptide

<400> SEQUENCE: 153

Ala Leu Ala Arg Pro Pro Cys Cys Val Pro Thr Ala
1               5                   10

<210> SEQ ID NO 154
<211> LENGTH: 12
<212> TYPE: PRT
<213> ORGANISM: artificial sequence
<220> FEATURE:
<223> OTHER INFORMATION: peptide

<400> SEQUENCE: 154

Cys Val Pro Thr Ala Tyr Ala Gly Lys Leu Leu Ile
1               5                   10

<210> SEQ ID NO 155
<211> LENGTH: 12
<212> TYPE: PRT
<213> ORGANISM: artificial sequence
<220> FEATURE:
<223> OTHER INFORMATION: peptide

<400> SEQUENCE: 155

Gly Lys Leu Leu Ile Ser Leu Ser Glu Glu Arg Ile
1               5                   10

<210> SEQ ID NO 156
```

```
<211> LENGTH: 12
<212> TYPE: PRT
<213> ORGANISM: artificial sequence
<220> FEATURE:
<223> OTHER INFORMATION: peptide

<400> SEQUENCE: 156

Ser Glu Glu Arg Ile Ser Ala His His Val Pro Asn
1               5                   10

<210> SEQ ID NO 157
<211> LENGTH: 12
<212> TYPE: PRT
<213> ORGANISM: artificial sequence
<220> FEATURE:
<223> OTHER INFORMATION: peptide

<400> SEQUENCE: 157

His His Val Pro Asn Met Val Ala Thr Glu Cys Gly
1               5                   10

<210> SEQ ID NO 158
<211> LENGTH: 12
<212> TYPE: PRT
<213> ORGANISM: artificial sequence
<220> FEATURE:
<223> OTHER INFORMATION: peptide

<400> SEQUENCE: 158

Val Pro Asn Met Val Ala Thr Glu Cys Gly Cys Arg
1               5                   10
```